US010836734B2

(12) United States Patent
Kim et al.

(10) Patent No.: US 10,836,734 B2
(45) Date of Patent: Nov. 17, 2020

(54) SPIROQUINONE DERIVATIVE COMPOUND, PRODUCTION METHOD THEREOF, AND PHARAMACEUTICAL COMPOSITION FOR PREVENTING OR TREATING NEUROLOGICAL DISORDERS WHICH CONTAINS SAME AS ACTIVE INGREDIENT

(71) Applicants: GACHON UNIVERSITY OF INDUSTRY-ACADEMIC COOPERATION FOUNDATION, Gyeonggi-do (KR); GIL MEDICAL CENTER, Incheon (KR)

(72) Inventors: Mi-Hyun Kim, Incheon (KR); Sun Yeou Kim, Incheon (KR); Sang-Yoon Lee, Incheon (KR); Venkanna Arramshetti, Incheon (KR); Kang Kim, Incheon (KR); Kyohee Cho, Incheon (KR); Prema Dhorma Lama, Incheon (KR)

(73) Assignees: GACHON UNIVERSITY OF INDUSTRY—ACADEMIC COOPERATION FOUNDATION, Gyeonggi-Do (KR); GIL MEDICAL CENTER, Incheon (KR)

( * ) Notice: Subject to any disclaimer, the term of this patent is extended or adjusted under 35 U.S.C. 154(b) by 0 days.

(21) Appl. No.: 16/044,285

(22) Filed: Jul. 24, 2018

(65) Prior Publication Data
US 2018/0327370 A1 Nov. 15, 2018

Related U.S. Application Data

(63) Continuation-in-part of application No. PCT/KR2017/009909, filed on Sep. 8, 2017.

(30) Foreign Application Priority Data

Sep. 8, 2016 (KR) .................. 10-2016-0115468

(51) Int. Cl.
| C07D 265/22 | (2006.01) |
| C07D 265/14 | (2006.01) |
| A61K 31/537 | (2006.01) |
| C07C 317/46 | (2006.01) |
| C07C 255/57 | (2006.01) |
| A23L 33/10 | (2016.01) |
| C07C 235/38 | (2006.01) |
| C07C 235/28 | (2006.01) |
| C07C 235/16 | (2006.01) |
| A61P 25/28 | (2006.01) |
| C07D 213/75 | (2006.01) |
| C07D 413/04 | (2006.01) |
| C07D 413/06 | (2006.01) |

(52) U.S. Cl.
CPC ............ *C07D 265/22* (2013.01); *A23L 33/10* (2016.08); *A61K 31/537* (2013.01); *A61P 25/28* (2018.01); *C07C 235/16* (2013.01); *C07C 235/28* (2013.01); *C07C 235/38* (2013.01); *C07C 255/57* (2013.01); *C07C 317/46* (2013.01); *C07D 213/75* (2013.01); *C07D 265/14* (2013.01); *C07D 413/04* (2013.01); *C07D 413/06* (2013.01)

(58) Field of Classification Search
CPC .. C07D 265/22; C07D 213/75; C07D 265/14; C07D 413/04; C07D 413/06
USPC ....................................................... 514/230
See application file for complete search history.

(56) References Cited

U.S. PATENT DOCUMENTS

2010/0056613 A1    3/2010  Yokoyama et al.

FOREIGN PATENT DOCUMENTS

| CN | 102850337 A | 1/2013 |
| CN | 105085433 A | 11/2015 |
| JP | 10-268489 | * 9/1998 ............... G03C 8/10 |
| JP | 10-268489 A | 10/1998 |
| KR | 10-2002-0040160 | 5/2002 |
| WO | WO 2008/129007 A1 | 4/2007 |

OTHER PUBLICATIONS

Alvira et al. "Inhibition of Cyclin-Dependent Kinases is Neuroprotective in 1-Methyl-4-Phenylpyridinium-Induced Apoptosis in Neurons" *Neuroscience* 146:350-365 (2007).
Benakis et al. "JNK inhibition and inflammation after cerebral ischemia" *Brain, Behavior, and Immunity* 24:800-811 (2010).
Canesi et al. "Fully Sterocontrolled Total Syntheses of (−)-Cylindricine C and (−)-2-Epicylindricine C: A Departure in Sulfonamide Chemistry" *Angew. Chem. Int. Ed.* 43:4336-4338 (2004).
Dickson et al. "Rare Variants Create Synthetic Genome-Wide Associations" *PLoS Biology* 8(1):1-12 (2010).
Dohi et al. "A Chiral Hypervalent Iodine (III) Reagent for Enantioselective Dearomatization of Phenols" *Angew. Chem. Int. Ed.* 47:3787-3790 (2008).
Draczkowski et al. "Determination of affinity and efficacy of acetylcholinesterase inhibitors using isothermal titration calorimetry" *BBA—General Subjects* 1860(5):967-974 (2016).
Gonzalez-Scarano and Baltuch "Microglia as Mediators of Inflammatory and Degenerative Diseases" *Annu. Rev. Neurosci.* 22-219-240 (1999).
Johnson et al. "Inhibition of neuronal apoptosis by the cyclin-dependent kinase inhibitor GW8510: Identification of 3' substituted indolones as a scaffold for the development of neuroprotective drugs" *Journal of Neurochemistry* 93:538-548 (2005).

(Continued)

*Primary Examiner* — Rita J Desai
(74) *Attorney, Agent, or Firm* — Klarquist Sparkman, LLP

(57) ABSTRACT

The present invention relates to a novel spiroquinone derivative compound, a production method thereof, and a pharmaceutical composition for preventing or treating neurological disorders which contains the compound as an active ingredient.

13 Claims, 9 Drawing Sheets

(56) References Cited

OTHER PUBLICATIONS

Kim et al. "Death-associated protein kinase 1 has a critical role in aberrant tau protein regulation and function" *Cell Death and Disease* (2014) 5,e1237; doi:10.1038/cddis.2014.216.

Lai et al. "Excitotoxicity and stroke: Identifying novel targets for neuroprotection" *Progress in Neurobiology* 115:157-188 (2013).

Manning and Davis "Targeting JNK for Therapeutic Benefit: From Junk to Gold?" *Nature* 2:554-565 (2003).

Nijboer et al. "Mitochondrial JNK phosphorylation as a novel therapeutic target to inhibit neuroinflammation and apoptosis after neonatal ischemic brain damage" *Neurobiology of Disease* 54:432-444 (2013).

Peng et al. "Protein kinase C-α signals P115RhoGEF phosphorylation and RhoA activation in TNF-α-induced mouse brain microvascular endothelial cell barrier dysfunction" *Journal of Neuroinflammation* 8:28 (2011).

Tahtouh et al. "Selectivity, Cocrystal Structures, and Neuroprotective Properties of Leucettines, a Family of Protein Kinase Inhibitors Derived from the Marine Sponge Alkaloid Leucettamine B" *Journal of Medicinal Chemistry* 55:9312-9330 (2012).

Wang et al. "JNK signaling is the shared pathway linking neuroinflammation, blood-brain barrier disruption, and oligodendroglial apoptosis in the white matter injury of the immature brain" *Journal of Neuroinflammation* 9:175 (2012).

\* cited by examiner

SPIROQUINONE DERIVATIVE COMPOUND, PRODUCTION METHOD THEREOF, AND PHARMACEUTICAL COMPOSITION FOR PREVENTING OR TREATING NEUROLOGICAL DISORDERS WHICH CONTAINS SAME AS ACTIVE INGREDIENT

CROSS REFERENCE TO RELATED APPLICATION

This patent application is a continuation-in-part of PCT/KR2017/009909, filed Sep. 8, 2017, which claims the benefit of priority from Korean Patent Application No. 10-2016-0115468, filed on Sep. 8, 2016. The contents of both patent applications are incorporated herein by reference.

BACKGROUND OF THE INVENTION

1. Field of the Invention

The present invention relates to a novel spiroquinone derivative compound, a preparation method thereof and a pharmaceutical composition comprising the same as an active ingredient for the prevention or treatment of neurological disease.

2. Description of the Related Art

Among the astrocytes composing the central nervous system, microglia are known to perform self-defense functions such as phagocytosis to eat up degenerated neurons and foreign substances. However, when TNF (tumor necrosis factor)-α produced for defense purposes or inflammation-inducing substances such as reactive oxygen species (ROS) or nitrogen compounds are excessively secreted or the cells themselves remain activated for a long time, an undesired side effect such as neuronal damage can be caused.

Recently, it has been found that not only degenerative neurological diseases such as Alzheimer's disease and Parkinson's disease but also neuronal damage due to trauma and ischemic conditions are involved in hypersensitization of microglia. Accordingly, studies have been undergoing to develop a therapeutic agent or a treatment method to inhibit the hypersensitized microglia or to suppress the functions of inflammation inducing substances secreted by microglia (Gonzalez-Scarano F and Baltuch G, Annu. Rev. Neurosci., 1999, 22, 219-240).

It is also known that the inhibition of acetylcholine esterase provides the neuroprotective effect. However, even though acetylcholine inhibitors could be effective in preventing and treating neurological disease, there is no fundamental disease modifying drugs (DMD) to control Alzheimer's disease, yet. Such clinical drugs as donepezil, galatamine and tacrine are only effective in delaying the prognosis of a disease but cannot eliminate or resolve the cause of a disease.

In the meantime, JNK knock-out mice showed a higher dopamine level and a lower loss of dopaminergic neurons, confirming that JNK played a certain role in the development of Parkinson's disease. However, JNK still needs to be studied as a drug for neurological disease.

The libraries of conventional drugs and drug candidates and active substances and compounds are composed basically of such materials that display a structural similarity with the structure of an endogenous ligand in vivo based on the heteroaromatic ring structure. Studies have been made so far to develop drugs and industrially available materials but continuous research and development are still ongoing.

The spiroquinone structure itself is a compound used as an intermediate for total synthesis of Spirooliganones A and B, which are natural products, and is known to be used as a drug medicine such as an anticancer agent or an infectious disease drug. In the previous studies, methods of synthesizing spiroquinone compounds through an oxidative cyclization reaction using a metal reagent such as cerium (CAN) or an oxidizing agent such as hypervalent iodine have reported. The conventional spiroquinone compound shows the structure in which single or one hetero atom is contained in the ring (Carnesi S et al., Angew. Chem. Int. Ed., 2004, 43, 4336-4338; Yasuyuki K et al., Angew. Chem. Int. Ed., 2008, 47, 3787-3790).

Under these circumstances, the present inventors tried to develop a novel spiroquinone derivative compound having excellent activity in the prevention or treatment of neurological disease. As a result, the inventors developed a method of introducing an amide group, which is frequently observed in the structure of medicines, into the spiroquinone skeleton and introducing an oxygen atom into the spiro position via oxidative cyclization, so that a novel spiroquinone derivative having three heteroatoms could be efficiently synthesized. It was first confirmed that an aminal structure could be introduced into the spiroquinone skeleton.

In addition, the present inventors confirmed that the novel spiroquinone derivative above was very useful in the prevention or treatment of neurological disease by inhibiting LPS (lipid polysaccharide) induced microglial activation and by suppressing cell death. It was also confirmed that the novel spiroquinone derivative not only inhibited acetylcholine esterase, JNK1, JNK2, and JNK3 significantly but also suppressed the enzyme activity of the neurological disease related enzyme group including RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, and TLK1. Accordingly, the present inventors confirmed that the novel spiroquinone derivative compound of the present invention could be effectively used as an active ingredient for a pharmaceutical composition for the prevention or treatment of neurological disease or a health functional food composition for the prevention or improvement of neurological disease, leading to the completion of the present invention.

SUMMARY OF THE INVENTION

It is an object of the present invention to provide a novel spiroquinone derivative compound, a stereoisomer thereof, or a pharmaceutically acceptable salt thereof.

It is another object of the present invention to provide a preparation method of the novel spiroquinone derivative compound, the stereoisomer thereof, or the pharmaceutically acceptable salt thereof.

It is also an object of the present invention to provide a pharmaceutical composition comprising the novel spiroquinone derivative compound, the stereoisomer thereof, or the pharmaceutically acceptable salt thereof as an active ingredient for the prevention or treatment of neurological disease.

It is further an object of the present invention to provide a health functional food composition comprising the novel spiroquinone derivative compound, the stereoisomer thereof, or the pharmaceutically acceptable salt thereof as an active ingredient for the prevention or improvement of neurological disease.

It is also an object of the present invention to provide a method for the prevention or treatment of neurological disease comprising the step of administering a pharmaceutically effective dose of the pharmaceutical composition above to a subject in need.

It is also an object of the present invention to provide a method for the prevention or treatment of neurological disease comprising the step of administering a pharmaceutically effective dose of the novel spiroquinone derivative compound, the stereoisomer thereof, or the pharmaceutically acceptable salt thereof to a subject in need.

It is also an object of the present invention to provide a use of the novel spiroquinone derivative compound, the stereoisomer thereof, or the pharmaceutically acceptable salt thereof for the prevention or treatment of neurological disease.

To achieve the above objects, the present invention provides a compound represented by formula 1 or formula 1' below, a stereoisomer thereof, or a pharmaceutically acceptable salt thereof.

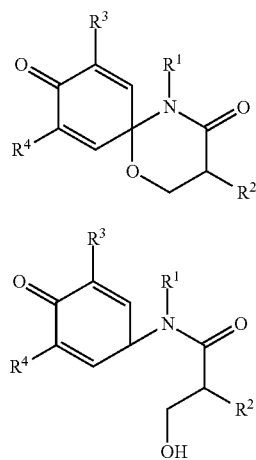

Formula 1

Formula 1'

In formula 1 or formula 1' above, $R^1$ and $R^2$ are the same or different. They are independently hydrogen, nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from the group consisting of N, O and S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from the group consisting of N, O, and S, or nonsubstituted or substituted 5-10 membered heteroaryl containing one or more heteroatoms selected from the group consisting of N, O, and S, wherein, the substituted alkyl, alkenyl, cycloalkyl, heterocycloalkyl, arylalkyl, aryl, heteroarylalkyl, or heteroaryl is independently substituted with one or more substituents selected from the group consisting of substituted or nonsubstituted $C_{6-10}$ arylsulfonyl, substituted or nonsubstituted $C_{6-10}$ arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from the group consisting of N, O and S, substituted or nonsubstituted 5-10 membered heteroarylsulfonyl $C_{1-5}$ alkyl containing one or more heteroatoms selected from the group consisting of N, O and S, substituted or nonsubstituted 5-10 membered heteroaryl containing one or more heteroatoms selected from the group consisting of N, O and S, substituted or nonsubstituted 5-10 membered heteroaryl $C_{1-5}$ alkyl containing one or more heteroatoms selected from the group consisting of N, O and S, substituted or nonsubstituted $C_{1-6}$ straight or branched alkyl, $C_{1-6}$ straight or branched alkoxy, hydroxy, halogen, amino, nitro, and cyano, wherein, the substituted $C_{6-10}$ arylsulfonyl, $C_{6-10}$ arylsulfonyl $C_{1-5}$ alkyl, $C_{6-10}$ aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from the group consisting of $C_{1-6}$ straight or branched alkyl, $C_{1-6}$ straight or branched alkoxy, hydroxy, halogen, amino, nitro, and cyano; and $R^3$ and $R^4$ are the same or different. They are independently hydrogen, nonsubstituted or substituted $C_{1-6}$ straight or branched alkyl, nonsubstituted or substituted $C_{1-6}$ straight or branched alkoxy, hydroxy, halogen, amino, nitro, and cyano, wherein, the substituted alkyl or alkoxy is independently substituted with one or more substituents selected from the group consisting of hydroxy, halogen, amino, nitro, and cyano.

The present invention also provides a preparation method of the compound represented by formula 1 comprising the step of preparing the compound represented by formula 1 from the compound represented by formula 2 (step 1), as shown in reaction formula 1 below.

Reaction Formula 1

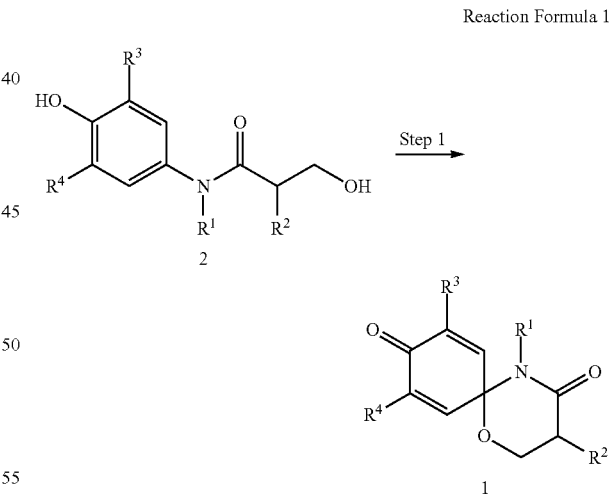

In reaction formula 1, $R^1$, $R^2$, $R^3$, and $R^4$ are as defined in formula 1 of claim 1.

The present invention also provides a pharmaceutical composition comprising the compound represented by formula 1 or formula 1', the stereoisomer thereof, or the pharmaceutically acceptable salt thereof as an active ingredient for the prevention or treatment of neurological disease.

The present invention also provides a health functional food comprising the compound represented by formula 1 or formula 1', the stereoisomer thereof, or the pharmaceutically acceptable salt thereof as an active ingredient for the prevention or improvement of neurological disease.

The present invention also provides a method for the prevention or treatment of neurological disease comprising the step of administering a therapeutically effective dose of the pharmaceutical composition to a subject in need.

In addition, the present invention provides a use of the compound represented by formula 1 or formula 1', the stereoisomer thereof, or the pharmaceutically acceptable salt thereof for the prevention or treatment of neurological disease.

Advantageous Effect

The novel spiroquinone derivative compound of the present invention, the stereoisomer thereof or the pharmaceutically acceptable salt thereof is not only excellent in inhibiting the microglial activation and the activities of acetylcholine esterase, JNK1, JNK2, and JNK3 but also displays the significant enzyme activity suppressive effect on the neurological disease related enzyme group including RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, and TLK1, in addition to the cell death suppressive effect. Therefore, the novel spiroquinone derivative compound of the present invention, the stereoisomer thereof or the pharmaceutically acceptable salt thereof can be effectively used as an active ingredient of a pharmaceutical composition for the prevention or treatment of neurological disease or as an active ingredient of a health functional food for the prevention or improvement of neurological disease.

DESCRIPTION OF THE PREFERRED EMBODIMENTS

Figure 1:
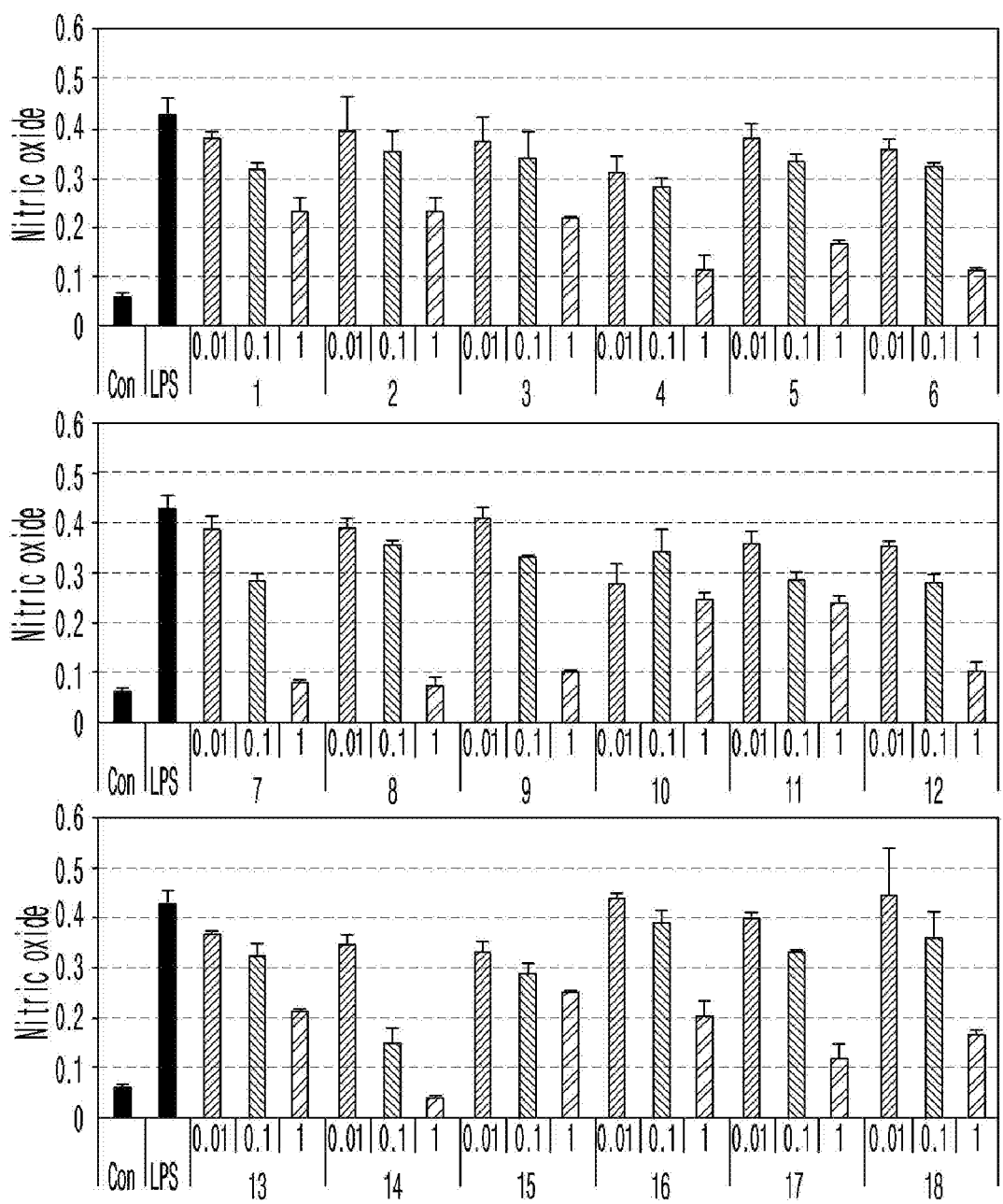
FIG. 1 is a set of graphs illustrating the nitrite generation from the comparison of nitric oxide measured in the neuronal cell line (murine microglial BV-2 cells) treated with a neurotoxicant (LPS) according to the different concentrations (0.01 μM, 0.1 μM, and 1 μM) of the compound of the present invention.

Hereinafter, the present invention is described in detail.

The present invention provides a compound represented by formula 1 or formula 1' below, a stereoisomer thereof, or a pharmaceutically acceptable salt thereof.

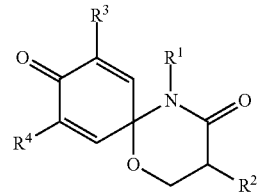

Formula 1

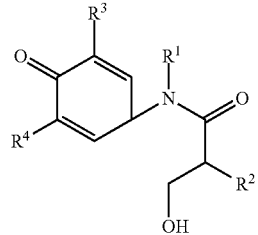

Formula 1'

In formula 1 or formula 1' above, $R^1$ and $R^2$ are the same or different. They are independently hydrogen, nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from the group consisting of N, O and S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from the group consisting of N, O, and S, or nonsubstituted or substituted 5-10 membered heteroaryl containing one or more heteroatoms selected from the group consisting of N, O, and S, wherein, the substituted alkyl, alkenyl, cycloalkyl, heterocycloalkyl, arylalkyl, aryl, heteroarylalkyl, or heteroaryl is independently substituted with one or more substituents selected from the group consisting of substituted or nonsubstituted $C_{6-10}$ arylsulfonyl, substituted or nonsubstituted $C_{6-10}$ arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from the group consisting of N, O and S, substituted or nonsubstituted 5-10 membered heteroarylsulfonyl $C_{1-5}$ alkyl containing one or more heteroatoms selected from the group consisting of N, O and S, substituted or nonsubstituted 5-10 membered heteroaryl containing one or more heteroatoms selected from the group consisting of N, O and S, substituted or nonsubstituted 5-10 membered heteroaryl $C_{1-5}$ alkyl containing one or more heteroatoms selected from the group consisting of N, O and S, substituted or nonsubstituted $C_{1-6}$ straight or branched alkyl, $C_{1-6}$ straight or branched alkoxy, hydroxy, halogen, amino, nitro, and cyano, wherein, the substituted $C_{6-10}$ arylsulfonyl, $C_{6-10}$ arylsulfonyl $C_{1-6}$ alkyl, $C_{6-10}$ aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from the group consisting of $C_{1-6}$ straight or branched alkyl, $C_{1-6}$ straight or branched alkoxy, hydroxy, halogen, amino, nitro, and cyano; and $R^3$ and $R^4$ are the same or different. They are independently hydrogen, nonsubstituted or substituted $C_{1-6}$ straight or branched alkyl, nonsubstituted or substituted $C_{1-6}$ straight or branched alkoxy, hydroxy, halogen, amino, nitro, and cyano, wherein, the substituted alkyl or alkoxy is independently substituted with one or more substituents selected from the group consisting of hydroxy, halogen, amino, nitro, and cyano.

In one aspect of the present invention, $R^1$ is nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from the group consisting of N, O and S, nonsubstituted or substituted $C_{6-10}$ aryl, or nonsubstituted or substituted 5-10 membered heteroaryl containing one or more heteroatoms selected from the group consisting of N, O, and S, wherein, the substituted alkyl, alkenyl, cycloalkyl, heterocycloalkyl, aryl, or heteroaryl is independently substituted with one or more substituents selected from the group consisting of $C_{1-6}$ straight or branched alkyl, $C_{1-6}$ straight or branched alkoxy, hydroxy, halogen, amino, nitro, and cyano.

In another aspect of the present invention, $R^2$ is hydrogen, nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from the group consisting of N, O and S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from the group consisting of N, O, and S, or nonsubstituted or substituted 5-10 membered heteroaryl containing one or more heteroatoms selected from the group consisting of N, O, and S, wherein, the substituted alkyl, alkenyl, cycloalkyl, heterocycloalkyl, arylalkyl, aryl, heteroarylalkyl, or heteroaryl is independently substituted with one or more substituents selected from the group consisting of substituted or nonsubstituted phenylsulfonyl, substituted or nonsubstituted phenylsulfonyl $C_{1-5}$ alkyl, substituted or nonsubstituted phenyl, substituted or nonsubstituted phenyl $C_{1-5}$ alkyl, substituted or nonsubstituted 5-10 membered heteroarylsulfonyl containing one or more heteroatoms selected from the group consisting of N, O and S, substituted or nonsubstituted 5-10 membered heteroarylsulfonyl $C_{1-5}$ alkyl containing one or more heteroatoms selected from the group consisting of N, O and S, substituted or nonsubstituted 5-10 membered heteroaryl containing one or more heteroatoms selected from the group consisting of N, O and S, substituted or nonsubstituted 5-10 membered heteroaryl $C_{1-5}$ alkyl containing one or more heteroatoms selected from the group consisting of N, O and S, substituted or nonsubstituted $C_{1-6}$ straight or branched alkyl, $C_{1-6}$ straight or branched alkoxy, hydroxy, halogen, amino, nitro, and cyano, wherein, the substituted $C_{6-10}$ arylsulfonyl, $C_{6-10}$ arylsulfonyl $C_{1-6}$ alkyl, $C_{6-10}$ aryl, $C_{6-10}$ aryl C alkyl, 5-10 membered heteroarylsulfonyl, 5-10 membered heteroarylsulfonyl $C_{1-6}$ alkyl, 5-10 membered heteroaryl, 5-10 membered heteroaryl alkyl, or $C_{1-6}$ straight or branched alkyl is independently substituted with one or more substituents selected from the group consisting of $C_{1-6}$ straight or branched alkyl, $C_{1-6}$ straight or branched alkoxy, hydroxy, halogen, amino, nitro, and cyano.

In another aspect of the present invention, $R^1$ is

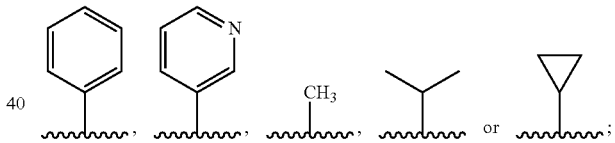

and $R^2$ is

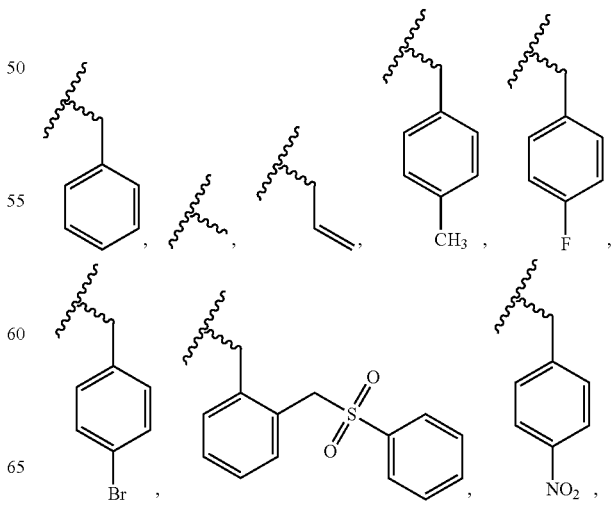

-continued

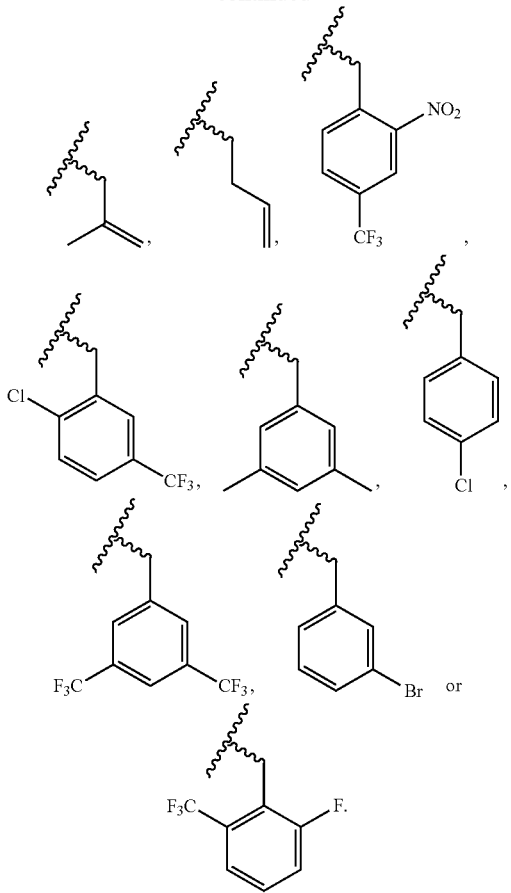

The following compounds are preferred examples of the compound represented by formula 1 or formula 1' according to the present invention.

(1) 5-phenyl-1-oxa-5-azaspiro[5,5]undeca-7,10-diene-4,9-dione;
(2) 3-methyl-5-phenyl-1-oxa-5-azaspiro[5,5]undeca-7,10-diene-4,9-dione;
(3) 3-allyl-5-phenyl-1-oxa-5-azaspiro[5,5]undeca-7,10-diene-4,9-dione;
(4) 3-(2-methyl-allyl)-5-phenyl-1-oxa-5-azaspiro[5,5]undeca-7,10-diene-4,9-dione;
(5) 3-(3-butenyl)-5-phenyl-1-oxa-5-azaspiro[5,5]undeca-7,10-diene-4,9-dione;
(6) 3-benzyl-5-phenyl-1-oxa-5-azaspiro[5,5]undeca-7,10-diene-4,9-dione;
(7) 3-(4-fluoro-benzyl)-5-phenyl-1-oxa-5-azaspiro[5,5]undeca-7,10-diene-4,9-dione;
(8) 3-(4-chloro-benzyl)-5-phenyl-1-oxa-5-azaspiro[5,5]undeca-7,10-diene-4,9-dione;
(9) 3-(3-bromo-benzyl)-5-phenyl-1-oxa-5-azaspiro[5,5]undeca-7,10-diene-4,9-dione;
(10) 3-(4-bromo-benzyl)-5-phenyl-1-oxa-5-azaspiro[5,5]undeca-7,10-diene-4,9-dione;
(11) 3-(4-trifluoromethyl-benzyl)-5-phenyl-1-oxa-5-azaspiro[5,5]undeca-7,10-diene-4,9-dione;
(12) 3-(4-nitro-benzyl)-5-phenyl-1-oxa-5-azaspiro[5,5]undeca-7,10-diene-4,9-dione;
(13) 3-(2-(phenylsulfonylmethyl)-benzyl)-5-phenyl-1-oxa-5-azaspiro[5,5]undeca-7,10-diene-4,9-dione;
(14) 3-(3,5-ditrifluoromethyl-benzyl)-5-phenyl-1-oxa-5-azaspiro[5,5]undeca-7,10-diene-4,9-dione;
(15) 3-(3,5-dimethyl-benzyl)-5-phenyl-1-oxa-5-azaspiro[5,5]undeca-7,10-diene-4,9-dione;
(16) 3-(2-nitro-4-trifluoromethyl-benzyl)-5-phenyl-1-oxa-5-azaspiro[5,5]undeca-7,10-diene-4,9-dione;
(17) 3-(2-fluoro-6-trifluoromethyl-benzyl)-5-phenyl-1-oxa-5-azaspiro[5,5]undeca-7,10-diene-4,9-dione;
(18) 3-(2-chloro-5-trifluoromethyl-benzyl)-5-phenyl-1-oxa-5-azaspiro[5,5]undeca-7,10-diene-4,9-dione;
(19) 3-benzyl-5-(pyridine-3-yl)-1-oxa-5-azaspiro[5,5]undeca-7,10-diene-4,9-dione;
(20) 3-methyl-5-(pyridine-3-yl)-1-oxa-5-azaspiro[5,5]undeca-7,10-diene-4,9-dione;
(21) 3-hydroxy-2-methyl-N-(4-oxocyclohexa-2,5-diethyl)-N-(pyridine-3-yl)propanamide;
(22) 3-methyl-8-fluoro-5-phenyl-1-oxa-5-azaspiro[5,5]undeca-7,10-diene-4,9-dione;
(23) 3-allyl-8-fluoro-5-phenyl-1-oxa-5-azaspiro[5,5]undeca-7,10-diene-4,9-dione;
(24) 3-benzyl-8-fluoro-5-phenyl-1-oxa-5-azaspiro[5,5]undeca-7,10-diene-4,9-dione;
(25) 3,8-dimethyl-5-phenyl-1-oxa-5-azaspiro[5,5]undeca-7,10-diene-4,9-dione;
(26) 3-allyl-8-methyl-5-phenyl-1-oxa-5-azaspiro[5,5]undeca-7,10-diene-4,9-dione;
(27) 3-(2-methyl-allyl)-8-methyl-5-phenyl-1-oxa-5-azaspiro[5,5]undeca-7,10-diene-4,9-dione;
(28) 3-benzyl-8-methyl-5-phenyl-1-oxa-5-azaspiro[5,5]undeca-7,10-diene-4,9-dione;
(29) 3,5-dimethyl-1-oxa-5-azaspiro[5,5]undeca-7,10-diene-4,9-dione;
(30) 3-allyl-5-methyl-1-oxa-5-azaspiro[5,5]undeca-7,10-diene-4,9-dione;
(31) 3-(3-butenyl)-5-methyl-1-oxa-5-azaspiro[5,5]undeca-7,10-diene-4,9-dione;
(32) 3-(2-methyl-allyl)-5-methyl-1-oxa-5-azaspiro[5,5]undeca-7,10-diene-4,9-dione;
(33) 3-benzyl-5-methyl-1-oxa-5-azaspiro[5,5]undeca-7,10-diene-4,9-dione;
(34) 3-(4-fluoro-benzyl)-5-methyl-1-oxa-5-azaspiro[5,5]undeca-7,10-diene-4,9-dione;
(35) 3-(4-bromo-benzyl)-5-methyl-1-oxa-5-azaspiro[5,5]undeca-7,10-diene-4,9-dione;
(36) 3-(4-cyano-benzyl)-5-methyl-1-oxa-5-azaspiro[5,5]undeca-7,10-diene-4,9-dione;
(37) 3-(2-(phenylsulfonylmethyl)-benzyl)-5-methyl-1-oxa-5-azaspiro[5,5]undeca-7,10-diene-4,9-dione;
(38) 3-allyl-5-phenyl-1-oxa-5-azaspiro[5,5]undeca-7,10-diene-4,9-dione;
(39) 3-((1-(4-methoxyphenyl)-1H-1,2,3-triazol-4-yl)methyl)-5-phenyl-1-oxa-5-azaspiro[5,5]undeca-7,10-diene-4,9-dione;
(40) 3-((1-benzyl-1H-1,2,3-triazol-4-yl)methyl)-5-phenyl-1-oxa-5-azaspiro[5,5]undeca-7,10-diene-4,9-dione;
(41) 3-methyl-5-isopropyl-1-oxa-5-azaspiro[5,5]undeca-7,10-diene-4,9-dione;
(42) 3-allyl-5-isopropyl-1-oxa-5-azaspiro[5,5]undeca-7,10-diene-4,9-dione;
(43) 3-(4-fluoro-benzyl)-5-isopropyl-1-oxa-5-azaspiro[5,5]undeca-7,10-diene-4,9-dione;
(44) 3-(4-trifluoromethyl-benzyl)-5-isopropyl-1-oxa-5-azaspiro[5,5]undeca-7,10-diene-4,9-dione;
(45) 3-(4-cyano-benzyl)-5-isopropyl-1-oxa-5-azaspiro[5,5]undeca-7,10-diene-4,9-dione;
(46) 3-(2-fluoro-6-trifluoromethyl-benzyl)-5-isopropyl-1-oxa-5-azaspiro[5,5]undeca-7,10-diene-4,9-dione;
(47) 3-((1-phenyl-1H-1,2,3-triazol-4-yl)methyl)-5-phenyl-1-oxa-5-azaspiro[5,5]undeca-7,10-diene-4,9-dione;

(48) 3-(3-bromobenzyl)-5-isopropyl-1-oxa-5-azaspiro[5,5]undeca-7,10-diene-4,9-dione; and
(49) 5-isopropyl-3-(4-nitrobenzyl)-1-oxa-5-azaspiro[5,5]undeca-7,10-diene-4,9-dione.

In one aspect of the present invention, the present invention provides a compound represented by formula 2 below, a stereoisomer thereof, or a pharmaceutically acceptable salt thereof.

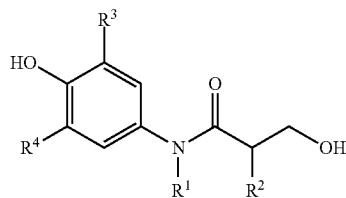

Formula 2

In reaction formula 2,
R$^1$, R$^2$, R$^3$, and R$^4$ are as defined in formula 1.

The compound represented by formula 1, formula 1', or formula 2 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 or formula 1' is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 or formula 1' but also a pharmaceutically acceptable salt thereof, and a solvate, a stereoisomer, or a hydrate possibly produced from the same.

The pharmaceutically acceptable salt of the novel spiroquinone derivative compound of the present invention is not limited as long as a candidate compound salt displays the equal preventive or therapeutic effect to the novel spiroquinone derivative compound of the invention.

The present invention also provides a preparation method of the compound represented by formula 1 comprising the step of preparing the compound represented by formula 1 from the compound represented by formula 2 (step 1), as shown in reaction formula 1 below.

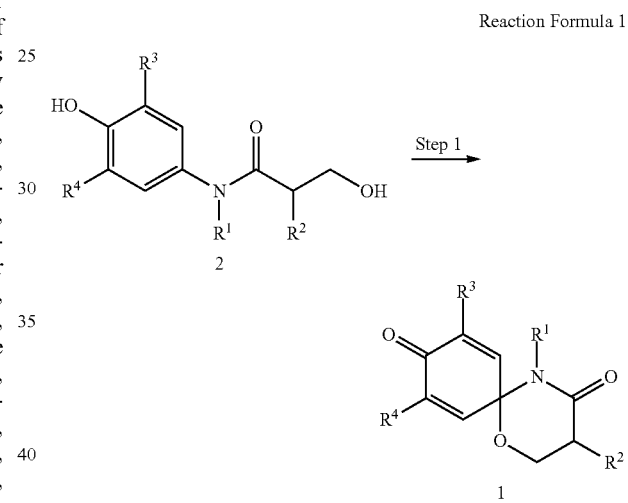

Reaction Formula 1

In reaction formula 1,
R$^1$, R$^2$, R$^3$, and R$^4$ are as defined in formula 1 of claim 1.

Hereinafter, the preparation method of the compound represented by formula 1 of the present invention is described in more detail, step by step.

In the preparation method of the compound represented by formula 1 of the present invention, step 1 of reaction formula 1 is to prepare the compound represented by formula 1 from the compound represented by formula 2.

At this time, step 1 can include any method that can produce the compound represented by formula 1 from the compound represented by formula 2, but is preferably understood as oxidative cyclization herein.

Herein, the oxidative cyclization is the reaction induced to produce 3,5-substituted oxazaspiroquinone that can performed by using a hypervalent iodine oxidizing agent.

As the hypervalent iodine oxidizing agent, BAIB (bis(acetoxy)iodobenzene) or PIFA (phenyliodinebis(trifluoroacetate)) is preferably used, but any oxidizing agent capable of performing the oxidative cyclization reaction of step 1 can be used without limitation and is included in the scope of the present invention.

The usable solvent in step 1 above is exemplified by $H_2O$, ethanol, tetrahydrofuran (THF), dichloromethane, toluene, acetonitrile, dimethylformamide, and hexafluoro isopropanol, and is preferably hexafluoro isopropanol herein, but not always limited thereto.

As shown in reaction formula 2 below, the compound represented by formula 2 can be prepared by the preparation method of the compound represented by formula 2 comprising the following steps:

preparing the compound represented by formula 7 from the compound represented by formula 8 (step 1);

preparing the compound represented by formula 6 from the compound represented by formula 7 prepared in step 1 above (step 2);

preparing the compound represented by formula 5 from the compound represented by formula 6 prepared in step 2 above (step 3);

preparing the compound represented by formula 4 from the compound represented by formula 5 prepared in step 3 above (step 4);

preparing the compound represented by formula 3 from the compound represented by formula 4 prepared in step 4 above (step 5); and preparing the compound represented by formula 2 from the compound represented by formula 3 prepared in step 5 above (step 6).

formula 2 is to prepare the compound represented by formula 7 from the compound represented by formula 8.

At this time, step 1 of reaction formula 2 is the step of introducing a protecting group into the hydroxy group of the compound represented by formula 8.

As shown in reaction formula 2, the protecting group can be MOM (methoxymethyl ether), but methyl ether, methoxymethyl ether, methoxyethyl ether, or benzyloxymethyl ether can also be used. In addition, any protecting group generally used in this field can be used without limitation, and this is included in the scope of the present invention.

In the preparation method of the compound represented by formula 2 above, step 2 of reaction formula 2 is to prepare the compound represented by formula 6 from the compound represented by formula 7.

At this time, step 2 of reaction formula 2 can be understood as the step of introducing the $NHR^1$ group in formula 6. This reaction is preferably induced in the presence of amine, a ligand such as $Pd_2(dba)_3$, NaOtBu, BINAP, or X-Phos, and anhydrous toluene, and the present invention includes any general modification possibly accepted for the inducement of the reaction above.

The temperature for carrying out the reaction is not particularly limited, but can be preferably performed at 20° C.~120° C.

Reaction Formula 2

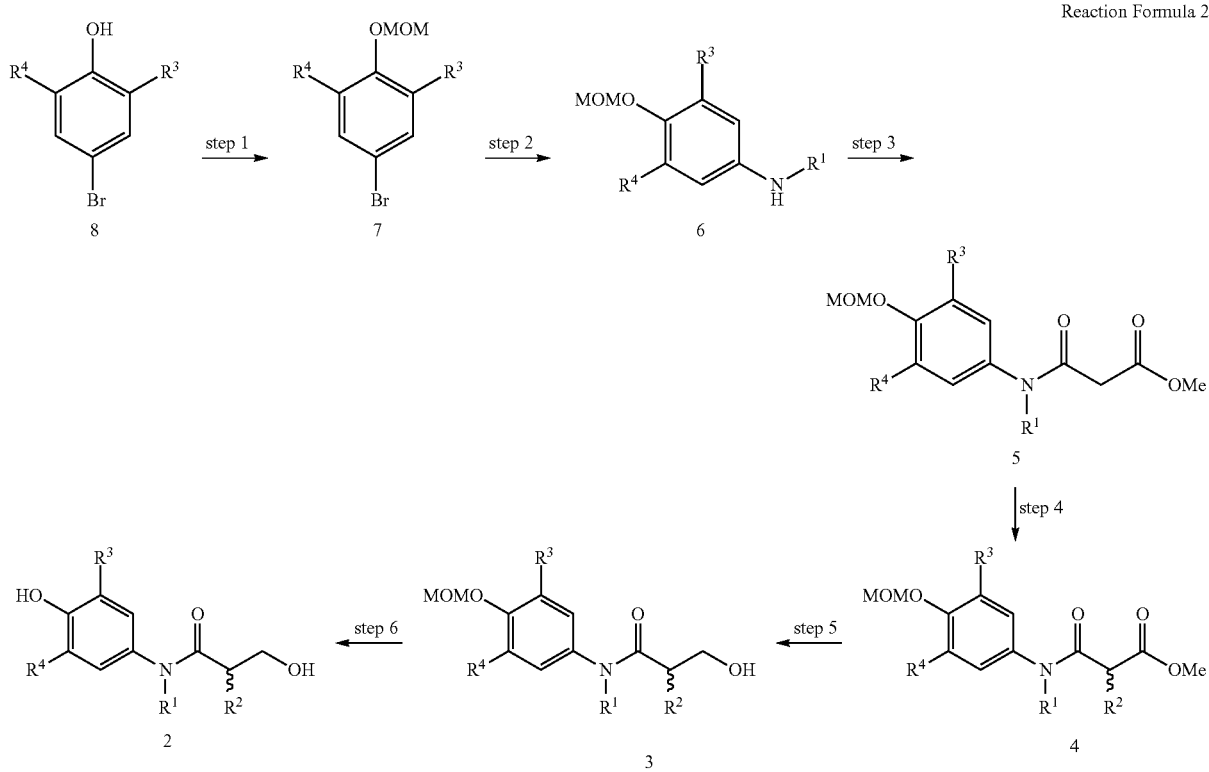

(In reaction formula 2, $R^1$, $R^2$, $R^3$, and $R^4$ are as defined in formula 1 of claim 1.)

Hereinafter, the preparation method of the compound represented by formula 2 is described in more detail, step by step.

In the preparation method of the compound represented by formula 2 of the present invention, step 1 of reaction In the preparation method of the compound represented by formula 2 above, step 3 of reaction formula 2 is to prepare the compound represented by formula 5 from the compound represented by formula 6.

At this time, step 3 of reaction formula 2 above can be understood as the step of obtaining N,N-substituted malonamide ester by inducing acyl substitution of malonic acid monoester. As an example, this reaction can be induced with the compound represented by formula 6 in the presence of methylmalonyl chloride. Any modification generally accepted in this field can be included in the scope of the present invention.

The temperature for carrying out the reaction is not particularly limited, but can be preferably performed at 0° C.~30° C.

In the preparation method of the compound represented by formula 2 above, step 4 of reaction formula 2 is to prepare the compound represented by formula 4 from the compound represented by formula 5.

At this time, step 4 of reaction formula 2 above is understood as the step of obtaining 2-substituted malonamide ester by introducing $R^2$ in the 2-position of N,N-substituted malonamide ester. As an example, this reaction can be induced with the compound represented by formula 5 in the presence of KOH (aqueous solution or solid), TBAI, $R^2$—X (halogen), and a proper solvent or in the presence of NaH, $R^2$—X (halogen) and an anhydrous solvent. Any modification generally accepted in this field can be included in the scope of the present invention.

The temperature for carrying out the reaction is not particularly limited, but can be preferably performed at 0° C.~30° C.

In the preparation method of the compound represented by formula 2 above, step 5 of reaction formula 2 is to prepare the compound represented by formula 3 from the compound represented by formula 4.

At this time, step 5 of reaction formula 2 above is understood as the step of reducing the ester group of the compound represented by formula 4. As an example, this reaction can be induced with the compound represented by formula 4 in the presence of $Li(OtBu)_3H$. Any modification generally accepted in this field can be included in the scope of the present invention.

The temperature for carrying out the reaction is not particularly limited, but can be preferably performed at −40° C.~0° C.

In the preparation method of the compound represented by formula 2 above, step 6 of reaction formula 2 is to prepare the compound represented by formula 2 from the compound represented by formula 3.

At this time, step 6 of reaction formula 2 is understood as the deprotection reaction to remove the protecting group introduced in step 1 above. Any modification generally accepted in this field can be included in the scope of the present invention.

Alternatively, when $R^2$ is C1-C6 alkyl, the compound represented by formula 2 can be obtained by reducing the ester group of N,N-substituted malonamide ester having a substituent at the 2-position introduced according to a literature (non-patent reference 3) by chemoselective reduction and removing the hydroxy protecting group of the protected phenol of the N,N-substituent.

The present invention also provides a preparation method of the compound represented by formula 1 comprising the step of preparing the compound represented by formula 1 from the compound represented by formula 2 (step 1), as shown in reaction formula 1 below.

In another aspect of the present invention, step 1 of reaction formula 1 is composed of the following steps, as shown in reaction formula 1':
preparing the compound represented by formula 1" from the compound represented by formula 2' (step 2); and
preparing the compound represented by formula 1 from the compound represented by formula 1" (step 3).

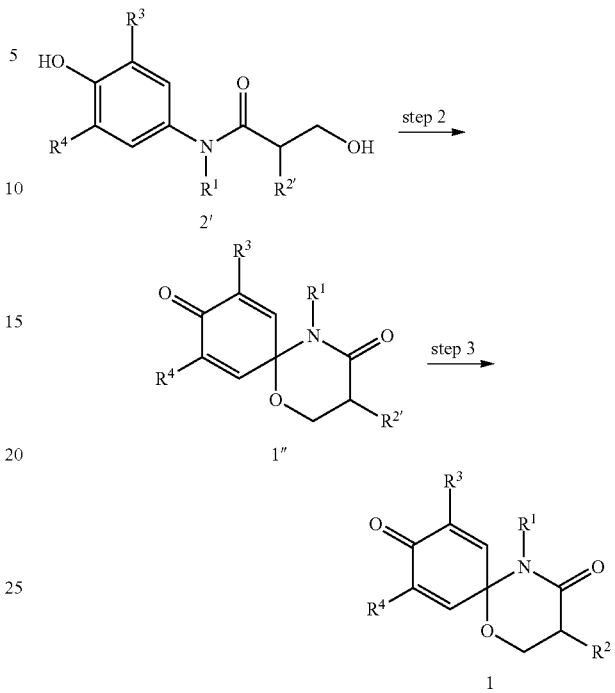

Reaction Formula 1'

In reaction formula 1',
$R^1$, $R^3$, and $R^4$ are as defined in formula 1;
$R^{2'}$ is $C_{1-5}$ straight or branched alkynyl containing one or more triple bonds; and

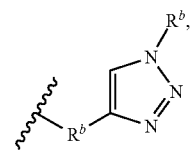

$R^2$ is preferably
wherein, $R^a$ is $C_{1-5}$ straight or branched alkylene,
$R^b$ is hydrogen, substituted or nonsubstituted $C_{6-10}$ arylsulfonyl, substituted or nonsubstituted $C_{6-10}$ arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from the group consisting of, N, O and S, substituted or nonsubstituted 5-10 membered heteroarylsulfonyl $C_{1-5}$ alkyl containing one or more heteroatoms selected from the group consisting of, N, O and S, substituted or nonsubstituted 5-10 membered heteroaryl containing one or more heteroatoms selected from the group consisting of, N, O and S, substituted or nonsubstituted 5-10 membered heteroaryl $C_{1-5}$ alkyl containing one or more heteroatoms selected from the group consisting of, N, O and S, substituted or nonsubstituted $C_{1-6}$ straight or branched alkyl, $C_{1-6}$ straight or branched alkoxy, hydroxy, halogen, amino, nitro, or cyano,
wherein, the substituted $C_{6-10}$ arylsulfonyl, $C_{6-10}$ arylsulfonyl $C_{1-6}$ alkyl, $C_{6-10}$ aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from the group consisting of $C_{1-6}$ straight or branched alkyl, $C_{1-6}$ straight or branched alkoxy, hydroxy, halogen, amino, nitro, and cyano.

Further, the present invention provides a pharmaceutical composition comprising the compound represented by formula 1 or formula 1', the stereoisomer thereof, or the pharmaceutically acceptable salt thereof as an active ingredient for the prevention or treatment of neurological disease.

The compound represented by formula 1 or formula 1' of the present invention, the stereoisomer thereof, or the pharmaceutically acceptable salt thereof can be effectively used for the prevention or treatment of neurological disease by inhibiting the cell death by suppressing the microglial activation, which can be an example of the industrial usage of the same, or by suppressing significantly the activities of acetylcholine esterase, JNK1, JNK2 and JNK3, and the neurological disease related enzyme group including RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, and TLK1.

Particularly, the pharmaceutical composition above can be used to treat injury, symptoms or disease caused by neurotoxic substances such as LPS (lipid polysaccharide) or by the over-activation of microglial cells or to prevent or treat neurological disease requiring the inhibition of the activity of acetylcholine esterase, JNK1, JNK2, JNK3, RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, or TLK1.

At this time, the term neurological disease as used herein indicates any nerve disorder benefiting from the inhibition of the microglial activation or the suppression of the activity of acetylcholine esterase, JNK1, JNK2, JNK3, RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, or TLK1. The neurological disease can include, in particular, cerebral nervous system disease and central nervous system disease.

More particularly, the neurological disease can be one or more diseases selected from the group consisting of multiple sclerosis, ischemic stroke, intracerebral hemorrhage, traumatic brain injury, spinal cord injury, Alzheimer's disease, Parkinson's disease, HIV-associated dementia, Huntington's disease, Lou Gehrig's disease, amyotrophic lateral sclerosis, myasthenia gravis, and Creutzfeldt-Jakob disease, but not always limited thereto.

In another aspect of the present invention, the neurological disease can be one or more diseases selected from the group consisting of attention deficit disorder, attention deficit hyperactivity disorder (ADHD), mild cognitive impairment, schizophrenia, age-associated memory impairment (AAMI), senile dementia, AIDS dementia, peak disease, Lewy body dementia, Down's syndrome related dementia, amyotrophic lateral sclerosis, Huntington's disease, smoking cessation, nicotine withdrawal symptoms, schizoaffective disorder, bipolar disorder and manic-depressive illness, CNS dysfunction associated with traumatic brain injury, acute pain, postoperative pain, chronic pain, inflammatory pain, and neuropathic pain.

In another aspect of the present invention, the neurological disease can be one or more diseases selected from the group consisting of Alzheimer's disease, Huntington's disease, Dandy-walker syndrome, Parkinson's disease, Parkinson-plus disease, amyotrophic lateral sclerosis (ALS), ischemia, stroke, intracranial hemorrhage, cerebral hemorrhage, brain barrier disorder, trigeminal neuralgia, tongue pharyngeal pain, Bell's palsy, myasthenia gravis, dystrophy, progressive muscular dystrophy, primary lateral sclerosis (PLS), false medulla oblongata palsy, progressive medulla oblongata palsy, progressive supranuclear palsy, spinal muscular atrophy, hereditary muscular dystrophy, invertebral disc syndrome, plexus disorder, cervical spondylosis, plexus disorder, chest exit syndrome, peripheral neuropathy, porphyria, multiple system atrophy, progressive supranuclear palsy, cortical basal degeneration, Lewy body dementia, anterior temporal dementia, dehydration disease, Guillain-Barre syndrome, multiple sclerosis, Charcot-Marie-Tooth disease, prion disease, Creutzfeldt-Jakob disease, Gerstmann-Straussler-Scheinker syndrome (GSS), fatal familial insomnia (FFI), bovine spongiform encephalopathy, Pick's disease, epilepsy, AIDS dementia complex; nerve damage due to exposure to toxic compounds selected from the group consisting of heavy metals, industrial solvents, drugs and chemotherapeutic agents; nervous system damage caused by physical, mechanical, or chemical trauma; glaucoma, lattice dystrophy, retinal pigment degeneration, age-related macular degeneration (AMD), photoreceptor degeneration associated with habit or dry AMD, other retinal degeneration, optic nerve drusen, optic neuropathy and optic neuritis.

To treat the diseases listed above, the pharmaceutical composition of the present invention brings the preventive and therapeutic effect on neurological disease by inhibiting the over-activation of microglia. The pharmaceutical composition of the present invention can also be efficient in preventing and treating neurological disease by protecting cells from neurotoxicity induced by LPS. Also, the pharmaceutical composition of the present invention can prevent and treat neurological disease by suppressing the activity of acetylcholine esterase. Further, the pharmaceutical composition of the present invention can prevent and treat neurological disease by suppressing the activity of JNK1, JNK2 or JNK3. In addition, the pharmaceutical composition of the present invention can prevent or treat neurological disease by suppressing the activity of RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, or TLK1.

The pharmacological effect of the compound represented by formula 1 or formula 1' of the present invention on the above-mentioned diseases have been demonstrated in the following experimental examples using the compounds of the examples of the present invention.

Particularly, the present inventors confirmed the protective effect of the compounds of the example of the present invention on nerve injury induced by LPS, and also confirmed the cell death suppression effect of the compounds resulted from inhibiting acetylcholine esterase activity and microglia.

In the experiment using a mouse model, drug-induced memory cognitive impairment was induced, and the recovery following the treatment with the compound of the present invention was investigated. The compound represented by formula 1 or formula 1' of the present invention was also efficient as an active ingredient for a pharmaceutical composition for the prevention or treatment of the disease or for a health functional food composition for the prevention or improvement of the disease.

The compound represented by formula 1 or formula 1' of the present invention, the stereoisomer thereof, the pharmaceutically acceptable salt thereof, the hydrate thereof, or the solvate thereof itself displays the cytoprotective activity, and it is also possible to bring a pharmacological effect by the specific internal environment or by the products of the metabolic process as an agonist.

Therefore, the pharmaceutical form for the administration of the compound represented by formula 1 or formula 1' of the present invention, the stereoisomer thereof, the pharmaceutically acceptable salt thereof, the hydrate thereof or the solvate thereof can be any pharmaceutically acceptable salt or the solvate.

The present invention also provides a food composition, such as a health functional food composition comprising the compound represented by formula 1 or formula 1', the stereoisomer thereof or the pharmaceutically acceptable salt thereof as an active ingredient for the prevention or improvement of neurological disease.

At this time, the health functional food composition can be prepared and used as a general health functional food composition containing the compound represented by formula 1 or formula 1' of the present invention, the stereoisomer thereof or the pharmaceutically acceptable salt thereof as an active ingredient.

Any formulation, food type, or administration pathway known to those in the art can be included in the scope of the present invention, and any health functional food composition can be included in the criteria of the health functional food composition of the present invention.

The term "prevention" in this invention indicates any activity to inhibit or delay the development of neurological disease by administering the pharmaceutical composition of the present invention to a subject.

The term "treatment" in this invention indicates any activity that is helpful for the improvement of the symptoms of neurological disease by administering the pharmaceutical composition of the present invention to a subject.

The pharmaceutical composition of the present invention can additionally include a pharmaceutically acceptable carrier, an excipient, or a diluent.

When the composition of the present invention is used as a medicinal drug, the pharmaceutical composition comprising the compound represented by formula 1 or formula 1', the stereoisomer thereof or the pharmaceutically acceptable salt thereof as an active ingredient can be formulated for oral or parenteral administration, but not always limited thereto.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the compound represented by formula 1 or formula 1' of the present invention can be administered by parenterally and the parenteral administration includes subcutaneous injection, intravenous injection, intramuscular injection or intrathoracic injection.

To prepare the composition as a formulation for parenteral administration, the compound represented by formula 1 or formula 1', the stereoisomer thereof or the pharmaceutically acceptable salt thereof of the present invention is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dose of the pharmaceutical composition comprising the compound represented by formula 1 or formula 1' as an active ingredient of the present invention can be adjusted according to age, weight, gender and health condition of patient, administration form, and severity of disease. The dose is preferably 0.01 to 1000 mg/kg/day, which can be administered orally or parenterally several times a day or preferably 1~3 times a day according to the judgment of a physician or a pharmacist.

Hereinafter, the preparation method of the compound represented by formula 1 or formula 1' is described in more detail with preparative examples or examples. The following examples are the examples to describe the preparation method of the compound represented by formula 1 or formula 1' and thus the present invention is not limited thereto. The preparation method described by the following examples can be accomplished by using proper reagents and synthesis conditions well-known in the field of organic synthesis.

The pharmaceutical composition of the present invention can be used as a single agent. It can also be formulated as a combined agent by including one or more other neurological disease therapeutic agents.

In another aspect of the present invention, the present invention provides a method for the prevention or treatment of neurological disease comprising the step of administering a therapeutically effective dose of the pharmaceutical composition to a subject in need.

The pharmaceutical composition indicates a pharmaceutical composition for the prevention or treatment of neurological disease, which comprises the compound represented by formula 1 or formula 1', the stereoisomer thereof or the pharmaceutically acceptable salt thereof as an active ingredient.

The neurological disease herein indicates any nerve disorder requiring the inhibition of the microglial activation or the suppression of the activity of acetylcholine esterase, JNK1, JNK2, JNK3, RIMS, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, or TLK1. The neurological disease can include, in particular, cerebral nervous system disease and central nervous system disease.

The neurological disease herein includes all the nerve disorders listed above. Particularly, the neurological disease includes the nerve disorders requiring the treatment based on the suppression of the microglial activation and the nerve disorders requiring the treatment based on the inhibition of the activity of acetylcholine esterase, JNK1, JNK2, JNK3, RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, or TLK1, which are exemplified by one or more diseases selected from the group consisting of multiple sclerosis, ischemic stroke, intracerebral hemorrhage, traumatic brain injury, spinal cord injury, Alzheimer's disease, Parkinson's disease, HIV-associated dementia, Huntington's disease, Lou Gehrig's disease, amyotrophic lateral sclerosis, myasthenia gravis, Creutzfeldt-Jakob disease, Dandy-walker syndrome, and progressive supranuclear palsy, but not always limited thereto.

To treat the diseases listed above, the pharmaceutical composition of the present invention brings the preventive and therapeutic effect for neurological disease by inhibiting the over-activation of microglia. The pharmaceutical composition of the present invention can also be efficient in preventing and treating neurological disease by protecting cells from neurotoxicity induced by LPS.

The term "therapeutically effective dose" can be understood by the minimum amount of the composition which shows the improvement, recovery and preferably the preventive or therapeutic effect on the disease in a subject when the compound of the present invention, the stereoisomer thereof or the pharmaceutically acceptable salt thereof is administered to the subject.

The term "administration" in this invention indicates the introduction of the pharmaceutical composition of the present invention into a subject via a proper pathway. The administration pathway for the pharmaceutical composition of the present invention can include any general pathway so long as it can reach the target tissue, which is exemplified by intraperitoneal administration, intramuscular administration, subcutaneous administration, intradermal administration, oral administration, topical administration, intranasal administration, intrapulmonary administration, rectal administration, intra-uterine administration, or intracerbroventricular injection, but not always limited thereto.

The term "subject" used in this invention indicates all the animals such as mammals including humans, mammals not including humans, and livestock wherein a neurological disease is developed or possibly occur. By administering the pharmaceutical composition of the present invention to a subject, the neurological disease can be effectively prevented or treated.

Next, the following experiments were performed in this invention in order to evaluate and examine the pharmacological activity and the therapeutic effect of the compound represented by formula 1 or formula 1' of the invention (the novel spiroquinone derivative compound) on disease.

First, an experiment was performed to evaluate the neuronal cell protection activity of the compound represented by formula 1 or formula 1' of the present invention (the novel spiroquinone derivative compound). As a result, it was shown that the production of nitrite was significantly inhibited in the LPS-treated neuronal cell line (murine microglial BV-2 cells) dose-dependently (see Experimental Example 1 FIG. 1 and Experimental Example 2 FIG. 3).

Figure 2:
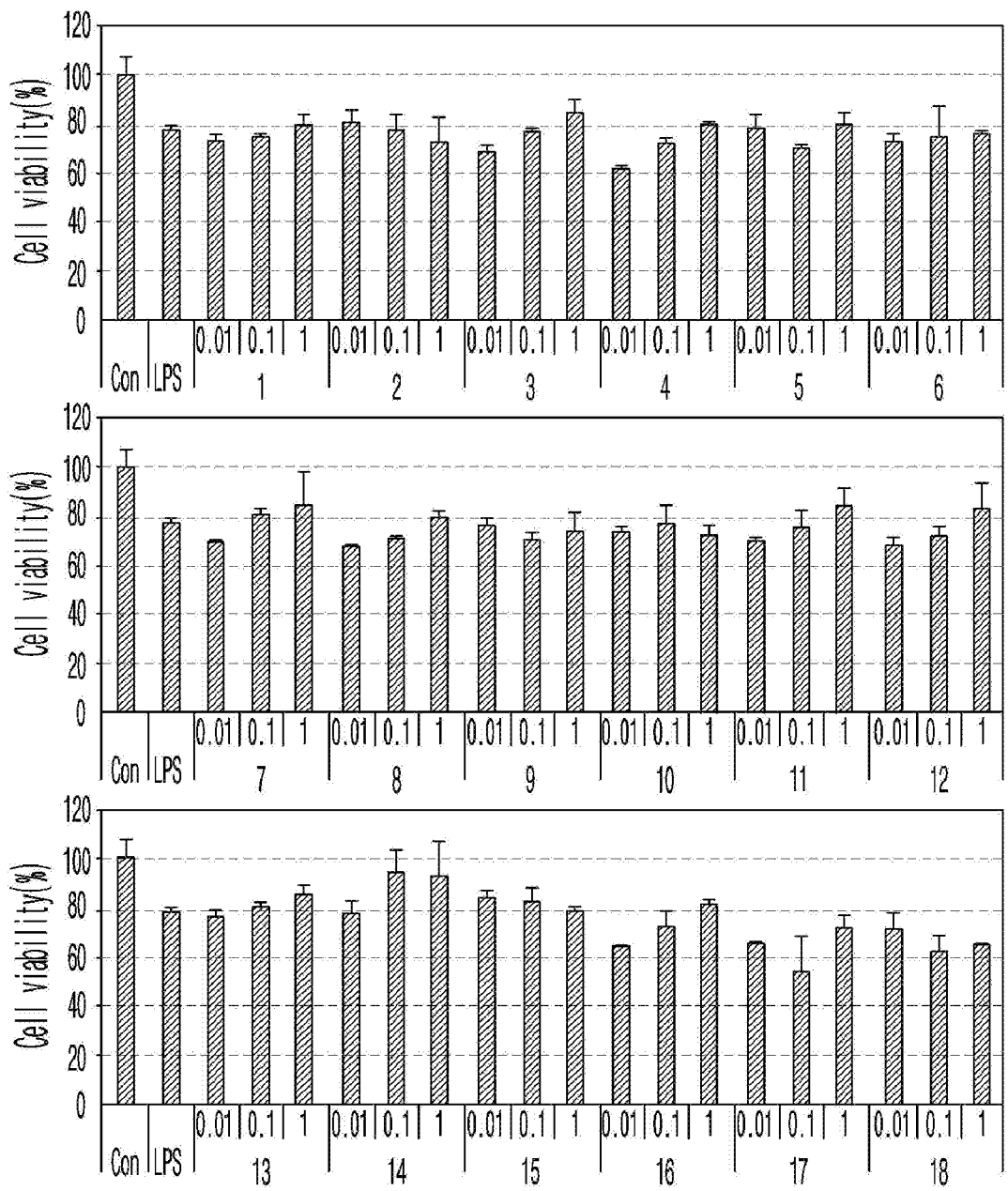
FIG. 2 is a set of graphs illustrating the cell survival rate (%) of the neuronal cell line (murine microglial BV-2 cells) treated with a neurotoxicant (LPS) according to the different concentrations (0.01 μM, 0.1 μM, and 1 μM) of the compound of the present invention.
Figure 4:
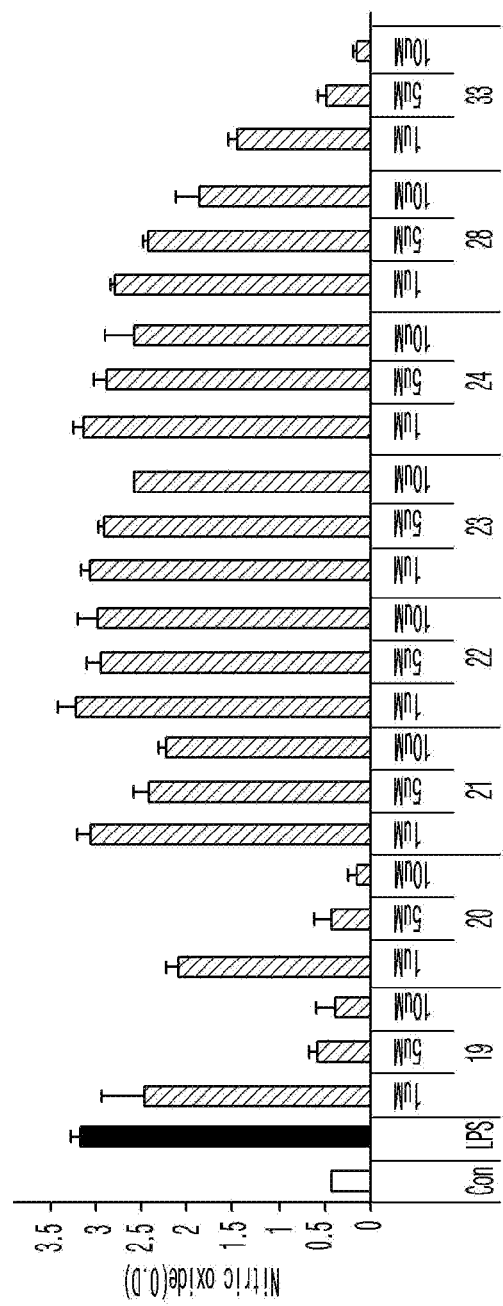
FIG. 4 is a graph illustrating the cell survival rate (%) of the neuronal cell line (murine microglial BV-2 cells) treated with a neurotoxicant (LPS) according to the different concentrations (1 μM, 5 μM, and 10 μM) of the compound of the present invention.

The compound of the present invention was also confirmed to increase the cell survival rate (%) significantly in the LPS-treated neuronal cell line (murine microglial BV-2 cells) dose-dependently (see Experimental Example 1 FIG. 2 and Experimental Example 2 FIG. 4).

Therefore, the compound of the present invention represented by formula 1 or formula 1' of the present invention was confirmed to have excellent neuroprotective effects (protective effect from oxidation caused by neurotoxic substances and stress) and significant inhibitory effects on microglial over-activation.

Further, the acetylcholine esterase inhibition activity of the compound of the present invention was also investigated and as a result a significant inhibition activity was confirmed.

Therefore, it was confirmed that the compound represented by formula 1 or formula 1' of the present invention was efficient in treating one or more diseases selected from the group consisting of the acetylcholine inhibition related diseases, for example the neurological diseases described in this specification and more specifically Alzheimer's disease, intractable epilepsy, stroke, cerebral infarct, head trauma, cerebral arteriosclerosis, Parkinson disease Huntington's disease, Creutzfeldt-Jakob disease, Pick's disease, Lewy body disease, amyotrophic lateral sclerosis, multiple sclerosis, ischemic brain disease, cerebrovascular disease, cranial nerve disease, cognitive disease or disorder, schizophrenia, attention deficit hyperactivity disorder (ADHD), attention deficit disorder (ADD), central nervous system (CNS) or peripheral nervous system (PNS) disease, Guillain-Barre syndrome, progressive dementia due to gradual killing of neurons, and progressive ataxia (see Experimental Example 3).

Another experiment was performed in order to investigate which kinases, among 369 kinases, were inhibited significantly by the compound of the present invention. As a result, the compound of the present invention significantly inhibited the enzyme activities of JNK1, CDK2/cyclin O, DAPK1, PKCa, CDK1/cyclin B, MST3/STK24, TLK1, JNK2, RIPK5, CDK3/cyclin E, PKN2/PRK2, Haspin, STK25/YSK1, ARK5/NUAK1, PKCb2, and JNK3, indicating that the compound of the present invention can be effectively used as an active ingredient of a pharmaceutical composition for the prevention or treatment of JNK1, CDK2/cyclin O, DAPK1, PKCa, CDK1/cyclin B, MST3/STK24, TLK1, JNK2, RIPK5, CDK3/cyclin E, PKN2/PRK2, Haspin, STK25/YSK1, ARK5/NUAK1, PKCb2, and JNK3 related diseases.

More precisely, the diseases related to each kinase are listed in Table 1 below.

TABLE 1

| Kinase | Disease | Reference |
|---|---|---|
| JNK 1 | Neurodegenerative disease, Ischemia, AD, PD | Neurobiology of Disease 54 (2013) 432-444Nat Rev Drug Discov. July 2003; 2(7):554-65.Journal of Neuroinflammation 2012, 9:175Brain, Behavior, and Immunity 24 (2010) 800.811 |
| CDK2/cyclin O | Neurodegenerative disease | Journal of Neurochemistry, 2005, 93, 538.548Neuroscience 146 (2007) 350-365 |
| DAPK1 | AD, Ischemia | Prog Neurobiol. April 2014; 115:157-88. Cell Death Dis. May 22, 2014; 5:e1237. |
| PKCa | Brain microvascular endothelial cell barrier disorder | Journal of Neuroinflammation 2011, 8:28 |
| CDK1/cyclin B | Neurodegenerative disease | Neuroscience 146 (2007) 350-365 |
| MST3/STK 24 | AD | PLoS Biol. January 2010; 8(1): e1000294 |
| JNK2 | Neurodegenerative disease, AD, PD | Neurobiology of Disease 54 (2013) 432-444Nat Rev Drug Discov. July 2003; 2(7):554-65. Journal of Neuroinflammation 2012, 9:175Brain, Behavior, and Immunity 24 (2010) 800.811 |
| RIPK5 | Alzheimer's disease, Down syndrome | J. Med. Chem. 2012, 55, 9312.9330 |
| CDK3/cyclin E | Neurodegenerative disease | Neuroscience 146 (2007) 350-365 |
| PKCb2 | Brain microvascular endothelial cell barrier disorder | Journal of Neuroinflammation 2011, 8:28 |
| JNK3 | Neurodegenerative disease, AD, PD | Neurobiology of Disease 54 (2013) 432-444Nat Rev Drug Discov. July 2003; 2(7):554-65. Journal of Neuroinflammation 2012, 9:175Brain, Behavior, and Immunity 24 (2010) 800.811 |

(*Alzheimer's disease: AD, Parkinson's disease: PD)

Therefore, it was confirmed that the compound represented by formula 1 or formula 1' of the present invention was effective in treating the kinase-related neurological diseases described above (see Experimental Example 4).

Further, it was confirmed from the animal model experiment (Y tube mouse experiment) using the compound represented by formula 1 or formula 1' (the novel spiroquinone derivative compound) that the administration of the compound of the invention to the mouse having induced memory impairment resulted in the recovery of memory impairment almost close to the level induced by donepezil.

Thus, it was confirmed that the compound of the present invention showed the neuroprotective effect and accordingly could be effectively used as a pharmaceutical composition for the prevention or treatment of all the neurological diseases described in this specification which are specifically exemplified by cerebral neurological diseases and central nervous system d Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of 2-benzyl-3-hydroxy-N-(4-hydroxyphenyl)-N-(pyridine-3-yl) propanamide

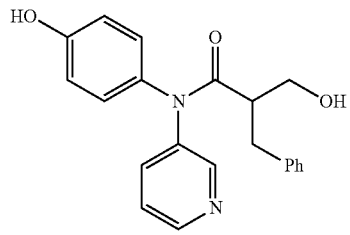 [SMILES: O=C(C(CO)Cc1ccccc1)N(c1ccc(O)cc1)c1cccnc1]

Step 1: Preparation of 1-bromo-4-(methoxymethoxy)benzene 50 mL of 4-bromophenol (5 g, 28.9 mmol) was dissolved in anhydrous tetrahydropyran, to which bromo(methoxy)methane (MOM-Br, 2.8 mL, 34.68 mmol) and sodium hydride (1.387 g, 34.68 mmol) were added, followed by stirring for 12 hours. The reaction was terminated by using methanol drop and distilled water. The reaction mixture was diluted with ethyl acetate and then washed with water and saturated brine. The organic phase was dried over sodium sulfate, followed by concentration in vacuo. The crude product was purified by using silica gel column chromatography (flash column chromatography) using EtOAc:Hex (1:9) as a moving phase to give the target compound (5.35 g, 85%).

$^1$H NMR (600 Hz, CDCl$_3$): δ 7.41 (d, J=8.6 Hz, 2H), 6.92 (d, J=8.24 Hz, 2H), 5.17 (s, 2H), 3.49 (s, 3H)

Step 2: Preparation of N-(4-(methoxymethoxyphenyl)pyridine-3-amine

The compound prepared in step 1 (1.4 g, 11.53 mmol), pyridine-3-amine (0.92 mL, 9.61 mmol), Pd$_2$(bda)$_3$ (0.437 g, 0.321 mmol), X-Phos (1.364 g, 1.364 mmol) and NaOtBu (1.318 g, 9.61 mmol) were dissolved in 10 mL of anhydrous toluene, which was added in a seal tube filled with argon gas, followed by stirring at 100~120° C. for 18 hours. The temperature was lowered to room temperature and the reaction was terminated with distilled water. The generated reaction mixture was diluted with ethyl acetate and then washed with water and saturated brine. The organic phase was dried over sodium sulfate, followed by concentration in vacuo. The crude product was purified by using silica gel column chromatography (flash column chromatography) using EtOAc:Hex (1:4) as a moving phase to give the target compound.

$^1$H NMR (600 Hz, CDCl$_3$): δ 8.27 (d, J=2.6 Hz, 1H), 8.08 (dd, J=4.5, 0.94 Hz, 1H), 7.26-7.23 (m, 1H), 7.12-7.09 (m, 1H), 7.06 (d, J=9.0 Hz, 2H), 7.01 (d, J=9.0 Hz, 2H), 5.87-5.85 (bs, 1H), 5.15 (s, 2H), 3.49 (s, 3H), 13C NMR (125 MHz, CDCl$_3$): δ 153.0, 141.2, 140.6, 138.5, 135.7, 123.6, 121.8 (3C), 121.4, 117.4 (2C), 94.8, 55.9 ppm.

The target compound of step 2 having an aromatic substituent substituted with heteroatoms such as pyridine can be prepared from pyridine-3-amine and 1-bromo-4-(methoxymethoxy)benzene as described in step 2 above. In addition to this method, the target compound of step 2 can be prepared by reacting 4-(methoxymethoxy)aniline and 3-bromopyridine as shown in reaction formula 3 below.

Reaction Formula 3

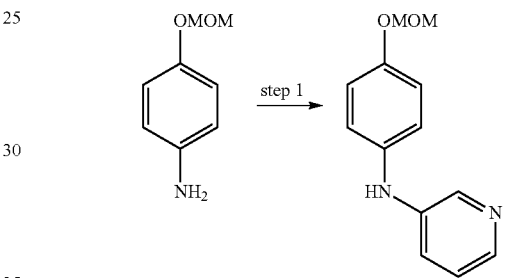

Step 2: Preparation of N-(4-(methoxymethoxy)phenyl)pyridine-3-amine

The oven-dried seal tube was filled with tri(dibenzylidineacetone)dipalladium (0.437 g, 0.321 mmol), (XPhos) palladium(2) phenethylamin chloride (1.364 g, 1.364 mmol), and sodium tert-butoxide (1.318 g, 9.61 mmol), to which degassed toluene anhydride (10 mL) was added. Then, 3-bromopyridine (0.92 mL, 9.61 mmol) and 4-(methoxymethoxy) aniline (1.4 g, 11.53 mmol) were added thereto after degassing with argon gas. The tube was filled with argon gas again. The mixture was stirred at room temperature for 5~10 minutes. After sealing with a Teflon screw cap, the mixture was stirred at 100~120° C. for 18 hours. The reaction progression was monitored by TLC. Upon completion of the reaction, the mixture was cooled to room temperature, diluted with dichloromethane (25 mL) and filtered with celite. Concentration was performed under reduced pressure. The crude product was purified by using silica gel column chromatography (flash column chromatography) using EtOAc:Hex (3:7) as a moving phase to give the target compound as a light brown solid (1.92 g, 87%).

$^1$H NMR (600 Hz, CDCl$_3$): δ 8.27 (d, J=2.6 Hz, 1H), 8.08 (dd, J=4.5, 0.94 Hz, 1H), 7.26-7.23 (m, 1H), 7.12-7.09 (m, 1H), 7.06 (d, J=9.0 Hz, 2H), 7.01 (d, J=9.0 Hz, 2H), 5.87-5.85 (bs, 1H), 5.15 (s, 2H), 3.49 (s, 3H)

Step 3: Preparation of methyl 3-((4-(methoxymethoxy)phenyl)(pyridine-3-yl)amino)-3-oxopropanoate 1.12 mL of 3-methoxy-3-oxopropanoic acid (9.08 mmol) was dissolved in 12 mL of anhydrous dichloromethane. The mixture was cooled to 0° C. with stirring. Then, EDCI.HCl (1.90 g, 9.91 mmol) and anhydrous HOBt (1.51 g, 9.91 mmol) were added thereto stepwise. The compound prepared in step 2 (1.9 g, 8.26 mmol) was added to the mixture at 0° C. The temperature was raised to room temperature. After 12 hours of stirring, the reaction was terminated with a saturated aqueous sodium bicarbonate solution. The generated reaction mixture was diluted with ethyl acetate and then washed with water and saturated brine. The organic phase was dried over sodium sulfate, followed by concentration in vacuo. The crude product was purified by silica gel column chromatography (flash column chromatography) using EtOAc:Hex (3:7) as a moving phase to give the target compound (1.85 g, 68%).

1.23 mL of methylmalonyl chloride was dissolved in 30 mL of anhydrous dichloromethane by another method. The mixture was cooled to 0° C. with stirring. Then, 5.5 mL of triethylamine was added thereto at 0° C. N-(4-(methoxymethoxyphenyl)pyridine-3-amine (1.9 g, 8.26 mmol) was added to the mixture at 0° C., and then the temperature was raised to room temperature slowly. After 12 hours of stirring, the reaction was terminated with a saturated aqueous sodium bicarbonate solution. The generated reaction mixture was diluted with ethyl acetate and then washed with water and saturated brine. The organic phase was dried over sodium sulfate, followed by concentration in vacuo. The crude product was purified by silica gel column chromatography (flash column chromatography) using EtOAc:Hex (3:7) as a moving phase to give the target compound (2.4 g, 86%).

$^1$H NMR (600 Hz, CDCl$_3$): δ 8.52 (s, 1H), 8.41 (s, 1H), 7.72 (d, J=6.9 Hz, 1H), 7.27-7.20 (m, 3H), 7.10 (d, J=7.3 Hz, 2H), 5.19 (s, 2H), 3.71 (s, 3H), 3.49 (s, 3H), 3.42 (s, 2H), $^{13}$C NMR (125 MHz, CDCl$_3$): δ 167.6, 166.5, 157.4, 146.9, 146.8, 138.9, 134.9, 132.9, 129.8 (2C), 123.3, 117.6 (2C), 94.3, 56.2, 52.4, 42.3 ppm.

Step 4: Preparation of methyl 2-benzyl-3-((4-(methoxymethoxy)phenyl)(pyridine-3-yl)amino)-3-oxopropanoate The compound prepared in step 3 (0.500 g, 1.515 mmol) was dissolved in toluene, to which tetra-n-butylammonium bromide (TBAB) (0.049 g, 0.1515 mmol) and 50% aqueous potassium hydroxide solution (0.54 mL, 19.61 mmol) were added stepwise at room temperature, followed by stirring. Benzylbromide (0.18 mL, 1.15 mmol) was added to the stirred solution, followed by stirring at room temperature until the substrate (the compound prepared in step 3) disappeared completely. The reaction was terminated with water and ethyl acetate. The reaction mixture was diluted with ethyl acetate and then washed with water and saturated brine. The organic phase was dried over sodium sulfate, followed by concentration in vacuo. The crude product was purified by silica gel column chromatography (flash column chromatography) using EtOAc:Hex (1:4) as a moving phase to give the target compound (0.458 g, 72%).

$^1$H NMR (600 Hz, CDCl$_3$): δ 8.37 (d, J=4.1 Hz, 1H), 8.31 (d, J=1.7 Hz, 1H), 7.48 (d, J=8.1 Hz, 1H), 7.36-7.27 (m, 4H), 7.23-7.19 (m, 1H), 7.14 (d, J=6.9 Hz, 3H), 6.97-6.89 (m, 2H), 5.16 (s, 2H), 3.83-3.78 (m, 1H), 3.77 (s, 3H), 3.48 (s, 3H), 3.33 (t, J=13.7 Hz, 1H), 3.20 (dd, J=13.1, 4.3 Hz, 1H), $^{13}$C NMR (125 MHz, CDCl$_3$): δ 169.4, 169.1, 157.1, 147.2, 146.8, 138.9, 137.9, 134.7, 133.1, 129.9, 129.4 (3C), 128.5 (2C), 126.9, 123.2, 117.1 (2C), 94.3, 56.1, 52.6, 51.3, 35.4 ppm.

Step 5: Preparation of 2-benzyl-3-hydroxy-N-(4-(methoxymethoxy)phenyl)-N-(pyridine-3-yl)pro-cainamide The compound prepared in step 4 (0.340 g, 0.8095 mmol) was dissolved in anhydrous THF (6 mL), to which LiAl(O-t-Bu)$_3$H (30% in THF, 8.9 mL, 10.523 mmol) was slowly added under argon atmosphere at −40° C. After stirring the mixture at −40° C. for 30 minutes, the temperature was slowly raised to room temperature with stirring. After confirming that the substrate (the compound prepared in step 4) disappeared completely, the reaction was quenched with a saturated sodium potassium tartrate aqueous solution. The reaction mixture was diluted with ethyl acetate and then stirred until the water layer and the organic layer became clear. The organic layer was separated and then washed with saturated brine. The organic phase was dried over sodium sulfate, followed by concentration in vacuo. The crude product was purified by silica gel column chromatography (flash column chromatography) using EtOAc:Hex (6:4) as a moving phase to give the target compound (0.269 g, 85%).

$^1$H NMR (600 Hz, CDCl$_3$): δ 8.37 (d, J=4.1 Hz, 1H), 8.36 (d, J=1.8 Hz, 1H), 7.49 (d, J=7.9 Hz, 1H), 7.33-7.27 (m, 3H), 7.24-7.20 (m, 1H), 7.08-7.05 (m, 3H), 6.98-6.91 (m, 3H), 5.17 (s, 2H), 3.86-3.81 (m, 1H), 3.79-3.76 (m, 1H), 3.49 (s, 3H), 3.07-3.01 (m, 1H), 2.78-2.74 (m, 1H).

$^{13}$C NMR (125 MHz, CDCl$_3$): δ 175.4, 156.9, 147.5, 146.8, 139.1, 138.6, 134.9, 133.3, 130.0, 129.2 (2C), 128.4 (2C), 126.6, 123.3, 117.1 (2C), 94.3, 63.8, 56.1, 46.7, 35.7 ppm.

HRMS (ESI): calcd. For $C_{23}H_{25}N_2O_4$ [M+H]$^+$ 393.1814; found 393.1814.

Step 6: Preparation of 2-benzyl-3-hydroxy-N-(4-hydroxyphenyl)-N-(pyridine-3-yl)propanamide The compound prepared in step 5 (0.180 g, 0.4591 mmol) was dissolved in 15 mL of acetonitrile and 15 mL of dichloromethane, followed by stirring. Sodium iodide (0.688 g, 4.591 mmol) was added thereto at 0° C., to which chlorotrimethylsilane (0.6 mL, 4.591 mmol) was added stepwise. After stirring the mixture for 1 hour, the reaction was terminated with a saturated aqueous sodium bisulfate solution. The organic layer obtained by extraction with dichloromethane (2×50 mL) was washed with a saturated aqueous sodium chloride solution. The organic phase was dried over sodium sulfate, followed by concentration in vacuo. The crude product was purified by silica gel column chromatography (flash column chromatography) using EtOAc:Hex (4:1) as a moving phase to give the target compound (0.111 g, 70%).

$^1$H NMR (600 Hz, CDCl$_3$): δ 9.14 (d, J=3.9 Hz, 1H), 9.1 (s, 1H), 8.25 (d, J=7.9 Hz, 1H), 8.17-8.05 (m, 5H), 7.85 (d, J=7.3 Hz, 2H), 7.67-7.61 (m, 1H), 7.51-7.44 (m, 2H), 5.69-5.62 (bs, 1H), 4.50 (t, J=8.4 Hz, 1H), 4.24-4.18 (m, 1H), 3.74-3.68 (m, 1H), 3.55-3.44 (m, 2H), $^{13}$C NMR (125 MHz, MeOD): δ 183.6, 157.0, 155.9, 149.3, 148.8, 143.0, 138.5 (4C), 137.7 (3C), 135.8 (2C), 133.2, 128.4 (2C), 72.4, 57.0, 44.9 ppm.

HRMS (ESI): calcd. For $C_{21}H_{21}N_2O_3$ [M+H]$^+$ 349.1552; found 349.1548.

Preparative Example 2: Preparation of 3-hydroxy-N-(4-hydroxyphenyl)-2-methyl-N-(pyridine-3-yl)propanamide

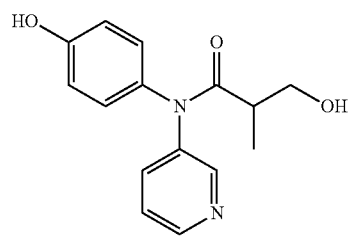 [SMILES: CC(CO)C(=O)N(c1ccc(O)cc1)c1cccnc1]

The target compound was prepared by the same manner as described in Preparative Example 1 except that iodomethane was used instead of benzylbromide in step 4 of Preparative Example 1.

$^1$H NMR (600 Hz, MeOD): δ 8.43 (s, 1H), 8.24 (s, 1H), 7.71-7.52 (m, 1H), 7.42-7.33 (m, 1H), 7.22-7.04 (m, 2H), 6.81-6.64 (m, 2H), 3.72-3.63 (m, 1H), 3.38-3.34 (m, 1H), 2.73-2.92 (m, 1H), 0.87 (d, J=1.7 Hz, 3H); $^{13}$C NMR (125 MHz, MeOD): 177.15, 157.75, 146.90, 145.78, 140.40, 134.47, 132.99, 129.82 (2C), 123.93, 116.20 (2C), 64.53, 39.92, 13.12 ppm.

$^1$H NMR (600 MHz, MeOD) δ 7.39-7.23 (m, 6H), 7.19 (t, J=7.3 Hz, 1H), 7.15-7.06 (m, 4H), 6.92 (d, J=8.7 Hz, 1H), 6.78-6.61 (m, 2H), 3.92-3.86 (m, 1H), 3.63-3.59 (m, 1H), 3.16-3.03 (m, 1H), 2.87-2.80 (m, 1H), 2.78-2.70 (m, 1H); $^{13}$C NMR (151 MHz, MeOD) δ 175.24, 156.99, 143.11, 139.21, 133.77, 129.68, 129.11, 129.09, 129.00, 128.53, 128.41, 128.12, 127.81, 127.36, 126.47, 126.23, 126.20, 115.43, 115.15, 63.61, 48.10, 35.57 ppm.

Preparative Example 3: Preparation of 2-benzyl-3-hydroxy-N-(4-hydroxyphenyl)-N-phenylpropanamide Preparative Example 4: Preparation of 2-benzyl-3-hydroxy-N-(4-hydroxyphenyl)-N-methylpropanamide

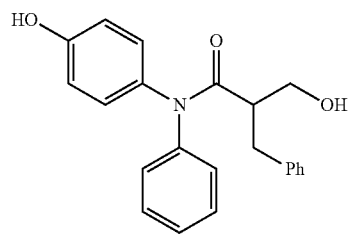 [SMILES: O=C(C(CO)Cc1ccccc1)N(c1ccccc1)c1ccc(O)cc1]

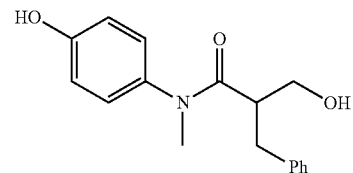 [SMILES: CN(C(=O)C(CO)Cc1ccccc1)c1ccc(O)cc1]

The target compound was prepared by the same manner as described in Preparative Example 1 except that aniline was used instead of pyridine-3-amine in step 2 of Preparative Example 1.

The secondary amine compound with the substitution of an alkyl group instead of an aromatic substituent can be prepared by the same manner as described in Preparation Example 4 as shown in reaction formula 4 below, unlike Preparation Examples 1-3 and 5-13.

Reaction Formula 4

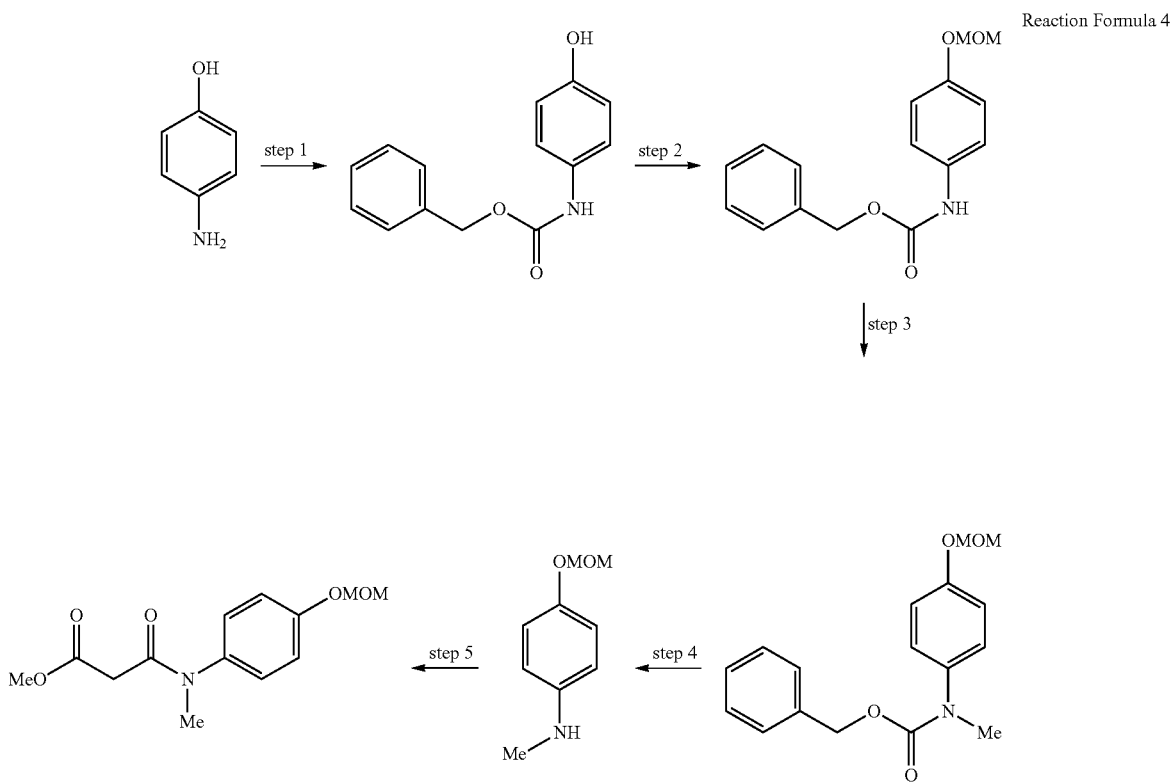

Step 1: Preparation of benzyl(4-hydroxyphenyl)carbamate 4-aminophenol (8.0 g, 73.3 mmol) was mixed with distilled water (91.5 mL) and tetrahydrofuran (91.5 mL) mixture (1:1), followed by stirring. After lowering the temperature of the mixture to 0° C., sodium carbonate (15.58 g, 146.7 mmol) was added thereto dropwise. A solution of benzyl chloroformate (12.5 mL, 76.2 mmol) in tetrahydrofuran (30 mL) was added thereto slowly. The temperature of the solution with brown floats was slowly raised to room temperature, followed by stirring for 1 hour. Then, tetrahydrofuran was removed in vacuo. The brown solution was diluted with distilled water (200 mL), followed by extraction with ethyl acetate. The organic layer was washed with brine, and dried over sodium sulfate. The solvent was removed under reduced pressure. The crude product was subjected to recrystallization from ethyl acetate to give the target compound (14.4 g, 61.6 mmol, 90%) as white crystals protected with a carboxybenzyl group.

$^1$H NMR (600 MHz, DMSO-$d_6$) δ δ 5.12 (s, 2H), 6.66-7.00 (m, 2H), 7.24 (d, J=8.1 Hz, 2H), 7.31-7.47 (m, 5H), 9.12 (s, 1H), 9.44 (br s, 1H) ppm.

Step 2: Preparation of benzyl(4-(methoxyketoxy)phenyl)carbamate

Sodium hydride (1.604 g, 66.87 mmol, dispersed in 60% paraffin oil) was mixed with anhydrous dimethylformamide (10 mL), to which the compound prepared in step 1 (13.8 g, 60.78 mmol) dissolved in anhydrous dimethylformamide (10 mL) was added slowly in the condition of nitrogen gas filled therein at 0° C. 30 minutes later when hydrogen gas was not generated anymore, the loading was stopped. Bromomethylmethylether (5.45 mL, 66.87 mmol) was slowly added thereto at 0° C., followed by stirring at room temperature for 2 hours. Upon completion of the reaction, the red solution was concentrated in vacuo. The residue was washed with ethyl acetate (250 mL), 10% citric acid (2×100 mL), 1 M sodium hydroxide (aq) (2×150 mL), and brine, followed by drying over sodium sulfate. The solvent was removed under reduced pressure. The crude product was subjected to recrystallization from ethanol to give the target compound (9.3 g, 56.8%) as white crystals.

$^1$H NMR (600 Hz, CDCl$_3$): δ 7.17-7.29 (m, 7H), 6.98 (d, J=9.0 Hz, 2H), 5.19 (s, 2H), 5.13 (s, 2H), 3.47 (s, 3H), $^{13}$C NMR (125 MHz, CDCl$_3$): δ 153.5, 136.0, 131.9, 128.5 (4C), 128.29 (2C), 128.26 (2C), 120.4, 116.8 (2C), 94.78, 66.9, 55.8 ppm.

Step 3: Preparation of benzyl(4-(methoxymethoxy)phenyl)(methyl)carbamate

Sodium hydride (0.93 g, 37.63 mmol, dispersed in 60% paraffin oil) was mixed with anhydrous dimethylformamide (15 mL), to which the compound prepared in step 2 (7.2 g, 25.08 mmol) dissolved in anhydrous dimethylformamide (20 mL) was added slowly in the condition of nitrogen gas filled therein at 0° C., followed by stirring for 30 minutes. 30 minutes later when hydrogen gas was not generated anymore, the loading was stopped. Methyl iodide (2.3 mL, 37.63 mmol) was slowly added thereto at 0° C., followed by stirring at room temperature for 6 hours. The reaction was terminated with cold ice cubes and the reaction mixture was extracted with ethyl acetate. The organic layer was washed with brine and dried over sodium sulfate. The solvent was removed under reduced the pressure. The crude product was purified by silica gel column chromatography (flash column chromatography) to give the brown target compound (6.5 g, 86%).

$^1$H NMR (600 Hz, CDCl$_3$): δ 7.38-7.27 (m, 5H), 7.16-7.24 (m, 2H), 7.04 (d, J=8.3 Hz, 2H), 5.19 (s, 4H), 3.51 (s, 3H), 3.30 (s, 3H) ppm.

Step 4: Preparation of 4-(methoxymethoxy)-N-methylalanine

The compound prepared in step 3 (6.0 g, 35.01 mmol) was dissolved in methanol, to which palladium (3.4 g, 5% activated carbon powder) filled with argon gas was added thereto. Argon gas was replaced with hydrogen gas, followed by stirring until the starting substrates were reacted completely. Upon completion of the reaction, the reaction mixture was filtered with a diatomite pad. The solvent was removed under reduced the pressure. The crude product was purified by silica gel column chromatography (flash column chromatography) to give the target compound (2.88 g, 86%) as yellow oil.

$^1$H NMR (600 Hz, CDCl$_3$): δ 7.28-7.25 (m, 4H), 5.04 (s, 2H), 2.77 (s, 3H) ppm.

Step 5: Preparation of methyl-3-((4-(methoxymethoxy)phenyl)(methyl)amino)-3-oxopropanoate Cooled methylmalonylchloride (1.57 mL, 14.65 mmol) was dissolved in dimethylformamide (10 mL), to which the compound prepared in step 4 (2.69 g, 16.11 mmol) dissolved in dimethylformamide (20 mL) was slowly added at 0° C., followed by stirring for 1 hour. The reaction was terminated with ice cubes and the reaction mixture was extracted with dichloromethane. The organic layer was washed with brine and dried over sodium sulfate. The solvent was removed under reduced the pressure. The crude product was purified by silica gel column chromatography (flash column chromatography) to give the target compound (3.8 g, 89%) as colorless liquid.

$^1$H NMR (600 Hz, CDCl$_3$): δ 7.13-7.06 (m, 4H), 5.2 (s, 2H), 3.69 (s, 3H), 3.50 (s, 3H), 3.28 (s, 3H), 3.23 (s, 3H) ppm.

Step 6: Preparation of 2-benzyl-3-hydroxy-N-(4-hydroxyphenyl)-N-methylpropanamide After step 5, the target compound was prepared by the same manner as described in step 4, step 5 and step 6 of Preparative Example 1.

$^1$H NMR (600 MHz, MeOD) δ 7.29-7.22 (m, 3H), 7.04-6.97 (m, 2H), 6.81-6.55 (m, 4H), 3.78 (dd, J=10.6, 8.2 Hz, 1H), 3.51 (dd, J=10.6, 5.8 Hz, 1H), 3.10 (d, J=3.8 Hz, 1H), 2.93-2.86 (m, 1H), 2.76 (dd, J=12.8, 10.2 Hz, 1H), 2.63 (dd, J=12.9, 4.8 Hz, 1H); $^{13}$C NMR (150 MHz, MeOD) δ 174.80, 156.85, 139.33, 134.68, 128.77 (2C), 128.34, 128.01 (2C), 126.02 (2C), 115.46 (2C), 63.36, 47.67, 36.61, 35.31 ppm.

Preparative Example 5: Preparation of 3-hydroxy-N-(4-hydroxyphenyl)-2-methyl-N-phenylpropanamide

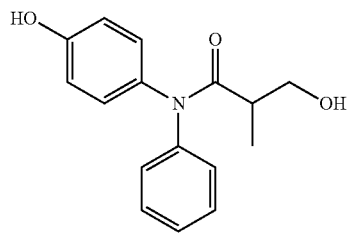 [SMILES: CC(CO)C(=O)N(c1ccccc1)c1ccc(O)cc1]

The target compound was prepared by the same manner as described in Preparative Example 1 except that aniline was used instead of pyridine-3-amine in step 2 and iodomethane was used instead of benzylbromide in step 4.

$^1$H NMR (600 MHz, MeOD) δ 7.51-7.06 (m, 7H), 6.91-6.67 (m, 2H), 3.79 (dd, J=10.4, 8.5 Hz, 1H), 3.44 (dd, J=10.0, 5.5 Hz, 1H), 2.87 (dd, J=16.7, 10.2 Hz, 1H), 1.05 (d, J=6.9 Hz, 3H); $^{13}$C NMR (150 MHz, MeOD) δ 178.16, 158.57, 144.51, 135.54, 130.83, 129.89, 129.51, 129.27, 128.88, 127.82, 127.40, 117.21, 116.54, 65.85, 41.23, 14.56 ppm.

Preparative Example 6: Preparation of 2-(hydroxymethyl)-N-(4-hydroxyphenyl)-N-phenylpent-4-enamide

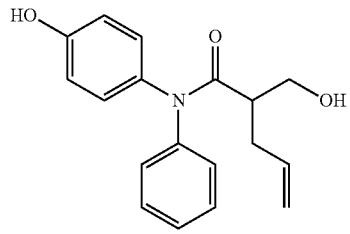 [SMILES: C=CCC(CO)C(=O)N(c1ccccc1)c1ccc(O)cc1]

The target compound was prepared by the same manner as described in Preparative Example 1 except that aniline was used instead of pyridine-3-amine in step 2 and allylbromide was used instead of benzylbromide in step 4.

$^1$H NMR (600 MHz, MeOD) δ 7.45-7.30 (m, 3H), 7.26 (s, 1H), 7.19 (d, J=7.4 Hz, 2H), 7.07 (d, J=8.4 Hz, 1H), 6.82 (d, J=8.5 Hz, 1H), 6.74 (d, J=8.4 Hz, 1H), 5.78-5.67 (m, 1H), 5.11-5.04 (t, J=12.4 Hz, 2H), 3.80 (dd, J=10.5, 8.5 Hz, 1H), 3.53 (dd, J=10.4, 5.4 Hz, 1H), 3.02-2.86 (m, 1H), 2.38-2.26 (m, 1H), 2.21-2.13 (m, 1H); $^{13}$C NMR (151 MHz, MeOD) δ 176.79, 158.51, 144.57, 136.51, 135.38, 131.25, 130.62, 129.88 (2C), 129.27, 127.87 (2C), 117.41, 117.06, 116.53, 64.49, 46.45, 35.14 ppm.

Preparative Example 7: Preparation of 3-hydroxy-N-(4-hydroxyphenyl)-N-phenyl-2-(4-(trifluoromethyl)benzyl)propanamide

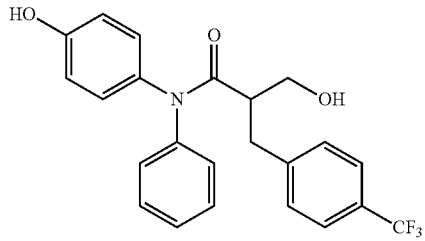

The target compound was prepared by the same manner as described in Preparative Example 1 except that aniline was used instead of pyridine-3-amine in step 2 and 4-trifluoromethylbenzylbromide was used instead of benzylbromide in step 4.

$^1$H NMR (600 MHz, MeOD) δ 7.65 (d, J=6.9 Hz, 2H), 7.38-7.24 (m, 5H), 7.19 (t, J=7.1 Hz, 1H), 7.10 (d, J=7.7 Hz, 1H), 6.91 (d, J=8.3 Hz, 1H), 6.76-6.60 (m, 3H), 3.91 (t, J=9.0 Hz, 1H), 3.66-3.61 (m, 1H), 3.19-3.06 (m, 1H), 2.98-2.80 (m, 2H); $^{13}$C NMR (150 MHz, MeOD) δ 176.09, 158.44, 145.38, 144.31, 135.68, 134.95, 131.02, 130.82, 130.44, 129.93, 129.55, 129.07, 128.82, 127.70, 127.60, 126.34, 126.31, 124.89, 116.88, 116.55, 64.79, 49.22, 36.57 ppm.

Preparative Example 8: Preparation of 2-(4-fluorobenzyl)-3-hydroxy-N-(4-hydroxyphenyl)-N-phenylpropanamide

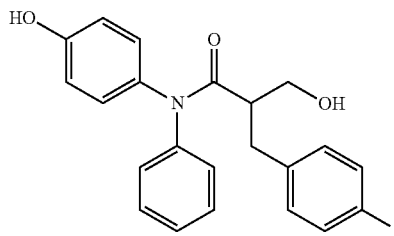

The target compound was prepared by the same manner as described in Preparative Example 1 except that aniline was used instead of pyridine-3-amine in step 2 and 4-fluorobenzylbromide was used instead of benzylbromide in step 4.

$^1$H NMR (600 MHz, MeOD) δ 7.32-7.24 (m, 3H), 7.17 (t, J=7.2 Hz, 1H), 7.13-6.98 (m, 6H), 6.91 (d, J=8.3 Hz, 1H), 6.75-6.58 (m, 2H), 3.86 (t, J=8.9 Hz, 1H), 3.58 (t, J=8.9 Hz, 1H), 3.12-2.99 (m, 1H), 2.85-2.77 (m, 1H), 2.74-7.68 (m, 1H); $^{13}$C NMR (150 MHz, MeOD) δ 176.40, 163.96, 158.40, 144.36, 136.50, 136.43, 135.74, 135.06, 132.04, 131.99, 130.41, 129.89, 129.11, 127.75, 127.55, 116.84, 116.52, 116.06, 115.92, 64.80, 49.39, 35.94 ppm.

Preparative Example 9: Preparation of 2-(4-bromobenzyl)-3-hydroxy-N-(4-hydroxyphenyl)-N-phenylpropanamide

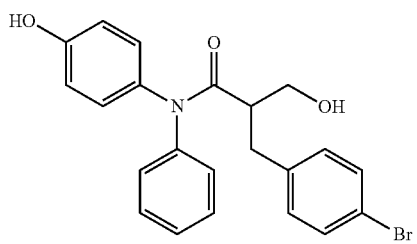 [SMILES: O=C(C(CO)Cc1ccc(Br)cc1)N(c1ccccc1)c1ccc(O)cc1]

The target compound was prepared by the same manner as described in Preparative Example 1 except that aniline was used instead of pyridine-3-amine in step 2 and 4-bromobenzylbromide was used instead of benzylbromide in step 4.

$^1$H NMR (600 Hz, MeOD): δ 7.58 (s, 1H), 7.47 (d, J=7.2 Hz, 2H), 7.31-7.26 (m, 3H), 7.19-7.15 (m, 1H), 7.09-7.07 (m, 2H), 7.06-6.96 (m, 2H), 7.09-7.07 (m, 2H), 6.92-6.88 (m, 1H), 6.73-6.66 (m, 2H), 3.86 (t, J=8.9 Hz, 1H), 3.58 (s, 1H), 3.09-3.01 (m, 1H), 2.82-2.71 (m, 2H) ppm.

Preparative Example 10: Preparation of 2-benzyl-3-hydroxy-N-(4-hydroxy-3-methylphenyl)-N-phenylpropanamide

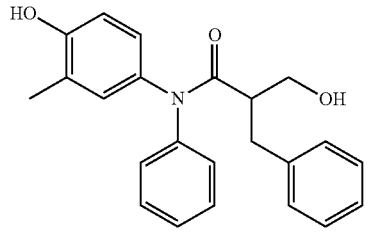 [SMILES: Cc1cc(N(C(=O)C(CO)Cc2ccccc2)c2ccccc2)ccc1O]

The target compound was prepared by the same manner as described in Preparative Example 1 except that 4-bromo-2-methylphenyl was used instead of 4-bromophenol in step 1 and aniline was used instead of pyridine-3-amine in step 2.

$^1$H NMR (600 Hz, MeOD): δ 7.37-7.21 (m, 5H), 7.19-7.13 (t, J=1.9 Hz, 1H), 7.13-7.05 (m, 3H), 6.79-6.67 (m, 1H), 6.66-6.55 (m, 1H), 3.90-3.82 (m, 1H), 3.62-3.54 (m, 1H), 2.86-2.76 (m, 1H) 2.75-2.66 (m, 1H), 2.13-1.95 (m, 3H); $^{13}$C NMR (150 Hz, MeOD): δ 176.76, 156.62, 144.73, 140.89, 130.68, 130.51, 130.05, 129.92, 129.68, 128.85, 128.34, 128.01, 127.83, 127.75, 127.75, 127.69, 126.51, 115.93, 115.82, 65.21, 37.15, 30.82, 16.32 ppm.

Preparative Example 11: Preparation of N-(4-hydroxy-3-methylphenyl)-2-(hydroxymethyl)-N-phenylpent-4-enamide

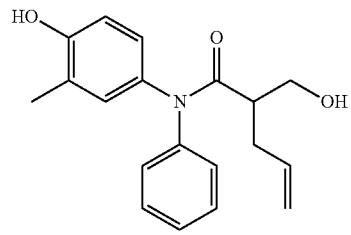 [SMILES: C=CCC(CO)C(=O)N(c1ccccc1)c1ccc(O)c(C)c1]

The target compound was prepared by the same manner as described in Preparative Example 1 except that 4-bromo-2-methylphenyl was used instead of 4-bromophenol in step 1, aniline was used instead of pyridine-3-amine in step 2, and allylbromide was used instead of benzylbromide.

$^1$H NMR (600 Hz, MeOD): δ 7.45-7.36 (m, 1H), 7.35-7.27 (m, 2H), 7.26-7.24 (m, 2H), 7.05-6.86 (m, 2H), 6.76-6.61 (m, 1H), 5.78-5.53 (m, 1H), 5.42-5.29 (m, 1H), 5.13-5.02 (m, 2H), 3.83-3.70 (m, 2H), 2.93-2.80 (m, 2H), 2.50-2.39 (m, 1H), 2.36-2.26 (m, 1H), 2.25-2.12 (m, 3H); $^{13}$C NMR (150 Hz, MeOD): δ 178.60, 140.45, 139.06, 136.41, 133.35, 132.50, 131.52, 129.98, 129.17, 127.90, 124.97, 122.49, 120.97, 110.36, 110.02, 77.93, 38.97, 30.89, 21.16 ppm.

Preparative Example 12: Preparation of 3-hydroxy-N-(4-hydroxy-3-methylphenyl)-2-methyl-N-phenylpropanamide

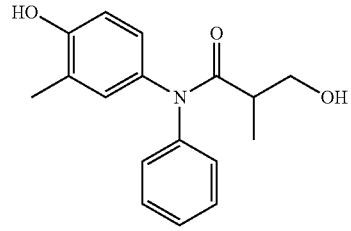 [SMILES: Cc1cc(N(C(=O)C(C)CO)c2ccccc2)ccc1O]

The target compound was prepared by the same manner as described in Preparative Example 1 except that 4-bromo-2-methylphenyl was used instead of 4-bromophenol in step 1, aniline was used instead of pyridine-3-amine in step 2, and methyliodide was used instead of benzylbromide.

$^1$H NMR (600 Hz, MeOD): δ 7.47-7.14 (m, 5H), 7.11-6.95 (m, 2H), 6.80-6.66 (m, 1H), 3.82-3.75 (t, J=1.7 Hz, 1H), 3.46-3.38 (m, 1H), 2.92-2.82 (m, 1H), 2.21-2.09 (m, 3H), 1.06-1.02 (d, J=1.1 Hz, 3H); $^{13}$C NMR (150 Hz, MeOD): δ 174.30, 147.54, 144.84, 144.22, 143.62, 130.96, 130.08 (2C), 128.16, 128.03, 127.56, 126.61, 122.96, 66.07, 41.45, 16.32, 14.80 ppm.

Preparative Example 13: Preparation of 2-benzyl-N-(3-fluoro-4-hydroxyphenyl)-3-hydroxy-N-phenyl-propanamide

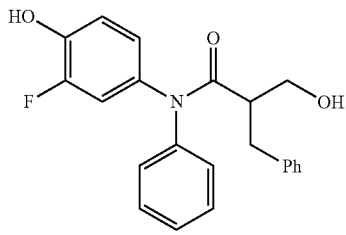 [SMILES: O=C(C(CO)Cc1ccccc1)N(c1ccccc1)c1ccc(O)c(F)c1]

The target compound was prepared by the same manner as described in Preparative Example 1 except that 4-bromo-2-fluorophenol was used instead of 4-bromophenol in step 1 and aniline was used instead of pyridine-3-amine in step 2.

$^1$H NMR (600 Hz, MeOD): δ 7.75-7.69 (m, 1H), 7.64-7.59 (m, 1H), 7.37-7.25 (m, 5H), 7.23-7.17 (m, 1H), 7.14-7.02 (m, 3H), 6.80-6.78 (m, 2H), 4.28 (t, J=6.6 Hz, 1H), 3.88 (t, J=5.8 Hz, 1H), 3.63-3.55 (m, 1H), 2.85-2.76 (m, 1H), 2.75-2.70 (m, 1H) ppm.

Preparative Example 14: Preparation of 3-hydroxy-N-(4-hydroxyphenyl)-N-phenylpropanamide

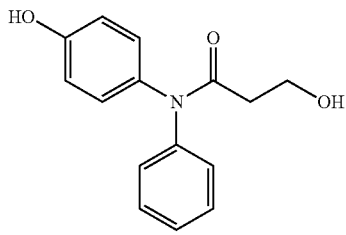 [SMILES: O=C(CCO)N(c1ccccc1)c1ccc(O)cc1]

Unlike Preparative Examples 1~13, when $R^2$ in reaction formula 1 was hydrogen, the target compound was prepared by the same method until step 3 of Preparative Example 1 and thereafter the preparation continued by the following reaction formula A, as shown in Preparative Example 14.

Reaction Formula A

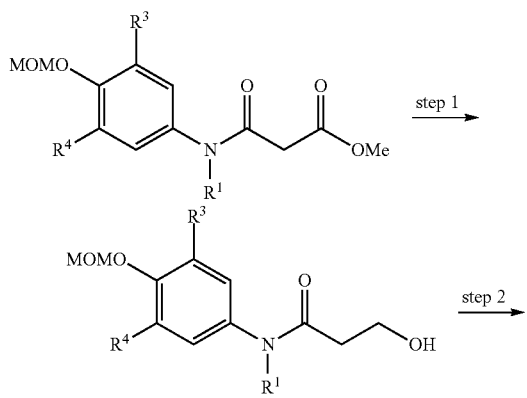

The compound of Preparative Example 14 was prepared as follows as shown in reaction formula A.

Step 1: Preparation of 3-hydroxy-N-(4-(methoxymethoxy)phenyl)-N-phenylpropanamide The compound prepared in step 3 of Preparative Example 1 (0.175 g, 0.53 mmol) was dissolved in anhydrous tetrahydrofuran, to which sodium borohydride (0.022 g, 0.58 mmol) was added at 0° C. The temperature was slowly raised to room temperature, during which the mixture was stirred for 24 hours. After confirming the complete consumption of the starting materials, the reaction mixture was filtered and then diluted with dichloromethane, followed by washing with water and saturated brine. The organic phase was dried over sodium sulfate, followed by concentration in vacuo. The crude product was purified by silica gel column chromatography (flash column chromatography) using EtOAc:Hex (1:1) as a moving phase to give the target compound (0.124 g, 78%).

1H NMR (600 MHz, CDCl$_3$) δ 7.39 (d, J=49.2 Hz, 2H), 7.29 (s, 1H), 7.11 (s, 2H), 6.84-6.57 (m, 3H), 3.88 (t, J=5.4 Hz, 2H), 3.64-3.47 (bs 1H), 2.52 (t, J=5.3 Hz, 2H); 13C NMR (150 MHz, CDCl$_3$) δ 173.53, 156.11, 142.40, 134.40, 129.94, 129.69, 128.99, 128.15, 127.85, 126.41, 126.09, 116.65, 116.18, 58.79, 37.08 ppm.

Step 2: Preparation of 3-hydroxy-N-(4-hydroxyphenyl)-N-phenylpropanamide

The final target compound was prepared by the method of step 6 of Preparative Example 1 by using the compound prepared in step 1 above.

$^1$H NMR (600 MHz, CDCl$_3$) δ 7.39 (d, J=49.2 Hz, 2H), 7.29 (s, 1H), 7.11 (s, 2H), 6.84-6.57 (m, 3H), 3.88 (t, J=5.4 Hz, 2H), 3.64-3.47 (bs 1H), 2.52 (t, J=5.3 Hz, 2H); $^{13}$C NMR (150 MHz, CDCl$_3$) δ 173.53, 156.11, 142.40, 134.40, 129.94, 129.69, 128.99, 128.15, 127.85, 126.41, 126.09, 116.65, 116.18, 58.79, 37.08 ppm.

Preparative Example 15: Preparation of 2-(hydroxymethyl)-N-(4-hydroxyphenyl)-4-methyl-N-phenylpent-4-enamide

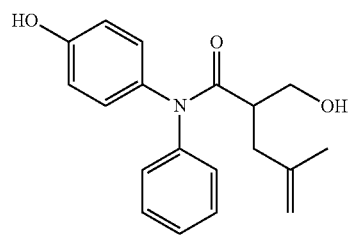 [SMILES: C=C(C)CC(CO)C(=O)N(c1ccccc1)c1ccc(O)cc1]

The target compound was prepared by the same manner as described in Preparative Example 1 except that aniline was used instead of pyridine-3-amine in step 2 and 4-bromo-2-methylbut-1-ene was used instead of benzylbromide in step 4.

¹H NMR (600 MHz, MeOD) δ 7.44-7.36 (m, 1H), 7.34-7.29 (m, 2H), 7.26-7.13 (m, 3H), 7.07 (d, J=8.5 Hz, 1H), 6.83 (d, J=8.5 Hz, 1H), 6.75 (d, J=8.5 Hz, 1H), 4.82-4.78 (m, 1H), 4.75 (d, J=8.0 Hz, 1H), 3.81 (t, J=9.5 Hz, 1H), 3.52-3.48 (m, 1H), 3.11-3.01 (m, 1H), 2.42-3.24 (m, 1H), 2.12-2.02 (m, 1H), 1.49 (d, J=33.9 Hz, 3H); ¹³C NMR (150 MHz, MeOD) δ 177.32, 158.66, 144.81, 144.10, 135.54, 131.43, 130.81, 130.09, 129.50, 128.98, 128.10, 127.68, 117.27, 116.74, 113.58, 64.83, 45.09, 39.22, 22.63 ppm.

Preparative Example 16: Preparation of 2-(hydroxymethyl)-N-(4-hydroxyphenyl)-N-phenylhex-5-enamide

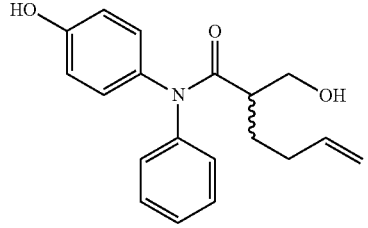 [SMILES: C=CCCC(CO)C(=O)N(c1ccccc1)c1ccc(O)cc1]

The target compound was prepared by the same manner as described in Preparative Example 1 except that aniline was used instead of pyridine-3-amine in step 2 and 4-bromobut-1-ene was used instead of benzylbromide in step 4.

¹H NMR (600 MHz, CDCl₃) δ 7.33-7.29 (m, 3H), 7.07-7.02 (m, 2H), 7.01 (dd, J=10.2, 3.2 Hz, 1H), 6.95 (dd, J=10.2, 3.2 Hz, 1H), 6.11-6.02 (m, 2H), 5.88-5.80 (m, 1H), 5.13-5.09 (m, 1H), 5.06-5.03 (m, 1H), 4.32 (dd, J=12.0, 5.3 Hz, 1H), 4.11 (dd, J=12.1, 6.9 Hz, 1H), 2.79 (m, 1H), 2.32-2.19 (m, 2H), 2.17-2.07 (m, 1H), 1.83-1.75 (m, 1H); ¹³C NMR (150 MHz, CDCl₃) δ 183.76, 170.25, 143.88, 143.47, 137.22, 136.31, 129.74 (2C), 129.55, 129.51, 128.87 (2C), 128.74, 115.60, 82.97, 63.78, 41.13, 30.94, 27.80 ppm.

Preparative Example 17: Preparation of 2-(4-chlorobenzyl)-3-hydroxy-N-(4-hydroxyphenyl)-N-phenylpropanamide

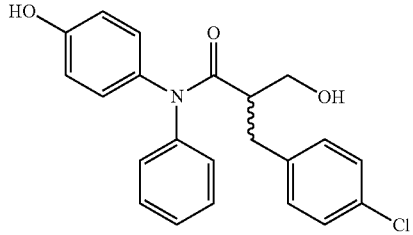 [SMILES: O=C(C(CO)Cc1ccc(Cl)cc1)N(c1ccccc1)c1ccc(O)cc1]

The target compound was prepared by the same manner as described in Preparative Example 1 except that aniline was used instead of pyridine-3-amine in step 2 and 1-(bromomethyl)-4-chlorobenzene was used instead of benzylbromide in step 4.

¹H NMR (600 MHz, MeOD) δ 7.36-7.26 (m, 4H), 7.18 (t, J=7.3 Hz, 1H), 7.13-7.02 (m, 4H), 6.90 (d, J=8.5 Hz, 1H), 6.76-6.57 (m, 3H), 3.86 (t, J=9.2 Hz, 1H), 3.62-3.53 (m, 1H), 3.14-3.01 (m, 1H), 2.84-2.76 (m, 1H), 2.75-2.67 (m, 1H); ¹³C NMR (150 MHz, MeOD) δ 176.35, 158.50, 144.42, 139.45, 135.09, 133.46, 132.05 (2 C), 131.00, 130.50, 129.98, 129.54 (2C), 129.17, 128.86, 127.81, 127.63, 116.93, 116.60, 49.31, 36.15, 20.84 ppm.

Preparative Example 18: Preparation of 2-(3-bromobenzyl)-3-hydroxy-N-(4-hydroxyphenyl)-N-phenylpropanamide

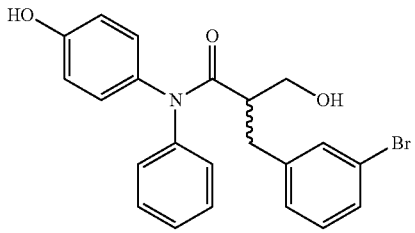 [SMILES: O=C(C(CO)Cc1cccc(Br)c1)N(c1ccccc1)c1ccc(O)cc1]

The target compound was prepared by the same manner as described in Preparative Example 1 except that aniline was used instead of pyridine-3-amine in step 2 and 1,3-dibromobenzene was used instead of benzylbromide in step 4.

¹H NMR (600 MHz, MeOD) δ 7.53-7.47 (m, 1H), 7.34-7.24 (m, 5H), 7.20 (t, J=7.4 Hz, 1H), 7.14-7.06 (m, 3H), 6.94-6.88 (m, 1H), 6.75-6.71 (m, 2H), 3.93-3.86 (m, 1H), 3.62 (dd, J=10.6, 6.0 Hz, 1H), 3.16-3.01 (m, 1H), 2.83-2.70 (m, 2H); 13C NMR (150 MHz, MeOD) δ 176.26, 158.52, 144.43, 143.34, 135.07, 133.53, 131.40, 130.74, 130.53, 130.02 (2C), 129.75, 129.45, 129.27, 127.93 (2C), 123.52, 116.97, 116.63, 64.93, 49.29, 36.58 ppm.

Preparative Example 19: Preparation of 3-hydroxy-N-(4-hydroxyphenyl)-2-(4-nitrobenzyl)-N-phenylpropanamide

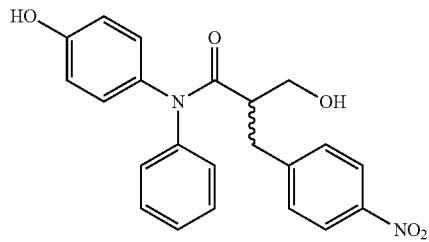 [SMILES: O=C(C(CO)Cc1ccc([N+](=O)[O-])cc1)N(c1ccccc1)c1ccc(O)cc1]

The target compound was prepared by the same manner as described in Preparative Example 1 except that aniline was used instead of pyridine-3-amine in step 2 and 1-bromo-4-nitrobenzene was used instead of benzylbromide in step 4.

¹H NMR (600 MHz, MeOD) δ 8.20 (d, J=8.3 Hz, 2H), 7.39-7.25 (m, 5H), 7.17 (t, J=7.3 Hz, 1H), 7.10 (d, J=7.8 Hz, 1H), 6.91 (d, J=8.4 Hz, 1H), 6.78-6.62 (m, 3H), 3.89 (t, J=9.1 Hz, 1H), 3.65-3.57 (m, 1H), 3.20-3.07 (m, 1H), 3.00-2.93 (m, 1H), 2.92-2.82 (m, 1H); ¹³C NMR (150 MHz, MeOD) δ 175.89, 158.64, 148.81, 148.31, 144.33, 134.99, 131.54, 130.95, 130.66, 130.04, 129.67, 129.16, 129.03, 127.78, 127.71, 124.62 (2C), 117.08, 116.66, 64.80, 48.75, 36.56 ppm.

Preparative Example 20: Preparation of 3-hydroxy-N-(4-hydroxyphenyl)-N-phenyl-2-(2-((phenylsulfonyl)methyl)benzyl)propanamide

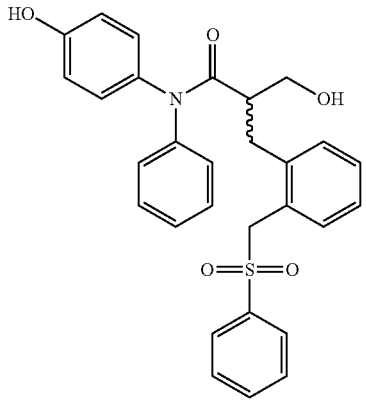 [SMILES: O=C(C(CO)Cc1ccccc1CS(=O)(=O)c1ccccc1)N(c1ccccc1)c1ccc(O)cc1]

The target compound was prepared by the same manner as described in Preparative Example 1 except that aniline was used instead of pyridine-3-amine in step 2 and 1-(bromomethyl)-2-((phenylsulfonyl)methyl)benzene was used instead of benzylbromide in step 4.

$^1$H NMR (600 MHz, MeOD) δ 7.89 (s, 1H), 7.75-7.58 (m, 3H), 7.52 (t, J=7.6 Hz, 2H), 7.34 (t, J=7.2 Hz, 1H), 7.29-7.20 (m, 4H), 7.15 (d, J=7.2 Hz, 2H), 7.08 (dd, J=20.8, 7.5 Hz, 1H), 6.99 (d, J=7.8 Hz, 1H), 6.80 (d, J=8.6 Hz, 1H), 6.71-6.55 (m, 3H), 4.59 (s, 1H), 4.44 (dd, J=30.1, 14.2 Hz, 1H), 4.28 (dd, J=32.0, 14.2 Hz, 1H), 3.79 (t, J=8.9 Hz, 1H), 3.52 (dd, J=9.8, 6.8 Hz, 1H), 3.04-2.90 (m, 1H), 2.76-2.59 (m, 2H); $^{13}$C NMR (150 MHz, MeOD) δ 176.21, 158.43, 144.23, 141.19, 139.66, 135.12, 134.94, 133.98, 132.21, 130.87, 130.48, 130.23 (2C), 129.98, 129.64 (2C), 129.58, 129.05, 128.87, 128.38, 127.90, 127.71, 127.67, 116.90, 116.59, 64.81, 59.88, 48.84, 33.20 ppm.

Preparative Example 21: Preparation of 2-(3,5-bis(trifluoromethyl)benzyl)₃-hydroxy-N-(4-hydroxyphenyl)-N-phenylpropanamide

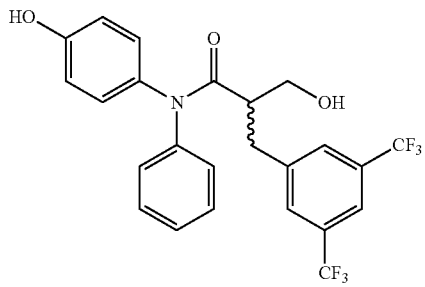 [SMILES: O=C(C(CO)Cc1cc(C(F)(F)F)cc(C(F)(F)F)c1)N(c1ccccc1)c1ccc(O)cc1]

The target compound was prepared by the same manner as described in Preparative Example 1 except that aniline was used instead of pyridine-3-amine in step 2 and 1-(bromomethyl)-3,5-bis(trifluoromethyl)benzene was used instead of benzylbromide in step 4.

$^1$H NMR (600 MHz, MeOD) δ 7.93 (s, 1H), 7.73 (s, 1H), 7.69 (s, 1H), 7.27 (dd, J=10.7, 4.9 Hz, 3H), 7.17 (t, J=7.4 Hz, 1H), 7.05-6.95 (m, 1H), 6.82 (d, J=8.8 Hz, 1H), 6.73-6.57 (m, 3H), 3.94-3.88 (m, 1H), 3.64 (dd, J=10.6, 6.1 Hz, 1H), 3.21-3.06 (m, 1H), 3.03-2.90 (m, 2H); $^{13}$C NMR (150 MHz, MeOD) δ 175.64, 158.76, 144.18, 144.16, 134.87, 132.99, 132.77, 131.07, 130.71, 130.00 (2C), 129.47, 129.05, 127.80, 127.69 (2C), 125.82, 124.02, 121.55, 117.13, 116.61, 64.78, 49.18, 36.39 ppm.

Preparative Example 22: Preparation of 2-(3,5-dimethylbenzyl)-3-hydroxy-N-(4-hydroxyphenyl)-N-phenylpropanamide

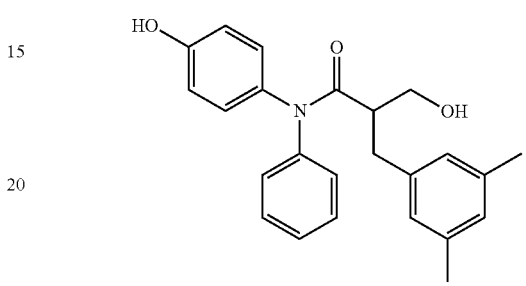

The target compound was prepared by the same manner as described in Preparative Example 1 except that aniline was used instead of pyridine-3-amine in step 2 and 1-bromo-3,5-dimethylbenzene was used instead of benzylbromide in step 4.

$^1$H NMR (600 MHz, MeOD) δ 7.31-7.14 (m, 4H), 7.06 (d, J=7.9 Hz, 1H), 6.94 (s, 1H), 6.86 (d, J=8.5 Hz, 1H), 6.68 (d, J=22.0 Hz, 5H), 3.86 (dd, J=15.9, 7.2 Hz, 1H), 3.58 (dd, J=10.3, 5.7 Hz, 1H), 3.11-2.99 (m, 1H), 2.73-2.59 (m, 2H), 2.30 (d, J=4.3 Hz, 6H); $^{13}$C NMR (150 MHz, MeOD) δ 175.41, 156.95, 143.17, 138.87, 137.66, 133.79, 129.77, 128.80, 128.51 (2C), 127.85, 127.60, 127.55, 127.00, 126.98, 126.52 (2C), 115.25, 115.12, 63.63, 48.10, 35.59, 20.02 (2C) ppm.

Preparative Example 23: Preparation of 3-hydroxy-N-(4-hydroxyphenyl)-2-(2-nitro-4-(trifluoromethyl)benzyl)-N-phenylpropanamide

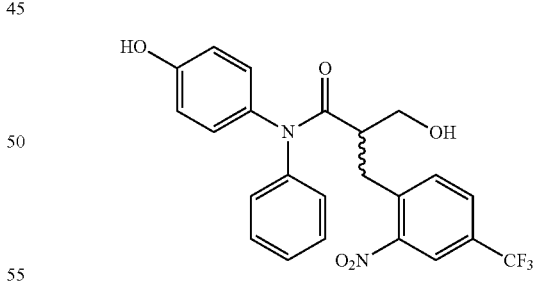

The target compound was prepared by the same manner as described in Preparative Example 1 except that aniline was used instead of pyridine-3-amine in step 2 and 1-(bromomethyl)-2-nitro-4-(trifluoromethyl)benzene was used instead of benzylbromide in step 4.

$^1$H NMR (600 MHz, MeOD) δ 8.31 (d, J=7.1 Hz, 1H), 8.05-8.01 (m, 1H), 7.66 (t, J=7.6 Hz, 1H), 7.30 (t, J=7.9 Hz, 1H), 7.24 (m, 2H), 7.18 (t, J=7.4 Hz, 1H), 7.10 (d, J=7.5 Hz, 1H), 6.91 (d, J=8.8 Hz, 1H), 6.76-6.53 (m, 3H), 3.89 (dd, J=10.6, 8.2 Hz, 1H), 3.66 (dd, J=10.6, 5.6 Hz, 1H), 3.37-3.31 (m, 1H), 3.30-3.24 (m, 1H), 3.08 (dd, J=12.7, 10.4 Hz,

1H); $^{13}$C NMR (150 MHz, MeOD) δ 175.71, 158.61, 150.82, 144.26, 140.07, 135.77, 134.84, 130.67, 130.04, 129.11, 129.03, 127.74 (2C), 125.46, 123.66, 123.42, 117.11, 116.66, 65.11, 48.76, 48.61, 47.50, 33.83 ppm.

Preparative Example 24: Preparation of 2-(2-fluoro-6-(trifluoromethyl)benzyl)-3-hydroxy-N-(4-hydroxyphenyl)-N-phenylpropanamide

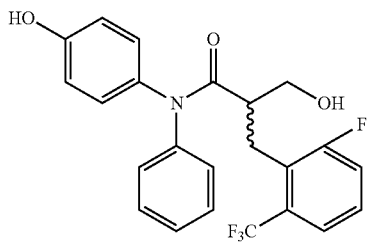 [SMILES: O=C(C(CO)Cc1c(F)cccc1C(F)(F)F)N(c1ccccc1)c1ccc(O)cc1]

The target compound was prepared by the same manner as described in Preparative Example 1 except that aniline was used instead of pyridine-3-amine in step 2 and 2-(bromomethyl)-1-fluoro-3-(trifluoromethyl)benzene was used instead of benzylbromide in step 4.

$^1$H NMR (600 MHz, MeOD) δ 7.89 (s, 1H), 7.53-7.47 (m, 2H), 7.43-7.39 (m, 1H), 7.31 (t, J=7.9 Hz, 2H), 7.24-7.14 (m, 4H), 7.03 (d, J=8.8 Hz, 1H), 6.73 (d, J=8.8 Hz, 1H), 6.59 (s, 1H), 3.93 (m, 1H), 3.54 (m, 1H), 3.27-3.21 (m, 1H), 3.20-3.13 (m, 1H), 2.83 (t, J=10.9 Hz, 1H); $^{13}$C NMR (150 MHz, MeOD) δ 175.88, 163.88, 158.01, 157.04, 144.17, 134.77, 130.13, 129.71, 129.58 (2C), 128.76, 128.35, 127.38 (2C), 127.18, 123.09, 120.33, 120.17, 116.58, 116.22, 64.80, 46.55, 26.15 ppm.

Preparative Example 25: Preparation of 2-(2-chloro-5-(trifluoromethyl)benzyl)-3-hydroxy-N-(4-hydroxyphenyl)-N-phenylpropanamide

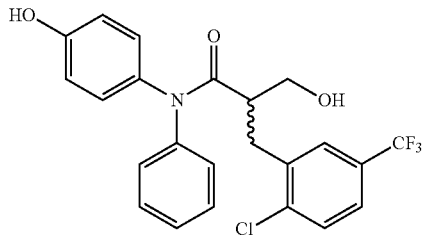 [SMILES: O=C(C(CO)Cc1cc(C(F)(F)F)ccc1Cl)N(c1ccccc1)c1ccc(O)cc1]

The target compound was prepared by the same manner as described in Preparative Example 1 except that aniline was used instead of pyridine-3-amine in step 2 and 2-(bromomethyl)-1-chloro-4-(trifluoromethyl)benzene was used instead of benzylbromide in step 4.

$^1$H NMR (600 MHz, MeOD) δ 7.61-7.58 (m, 3H), 7.32-7.26 (m, 3H), 7.17 (dd, J=9.3, 1H), 7.09-7.04 (m, 2H), 6.86 (d, J=8.8 Hz, 1H), 6.68 (d, J=8.8 Hz, 2H), 3.97-3.85 (m, 1H), 3.73-3.51 (m, 1H), 3.39-3.31 (m, 1H), 3.04 (m, 1H), 2.97-2.86 (m, 1H); $^{13}$C NMR (150 MHz, MeOD) δ 174.52, 157.17, 156.12, 142.84, 138.12, 133.48, 130.30, 129.22, 128.87, 128.52 (2C), 128.11, 127.68, 127.51, 126.34 (2C), 126.31, 124.88, 115.65, 115.12, 63.49, 44.81, 33.30 ppm.

Preparative Example 26: Preparation of 3-hydroxy-N-(4-hydroxyphenyl)-2-methyl-N-(pyrodi-3-nyl)propanamide

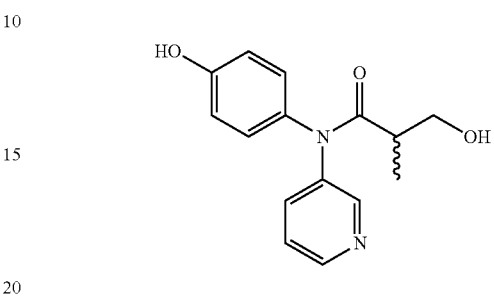

The target compound was prepared by the same manner as described in Preparative Example 1 except that iodomethane was used instead of benzylbromide in step 4.

$^1$H NMR (600 Hz, MeOD): δ 8.43 (s, 1H), 8.24 (s, 1H), 7.71-7.52 (m, 1H), 7.42-7.33 (m, 1H), 7.22-7.04 (m, 2H), 6.81-6.64 (m, 2H), 3.72-3.63 (m, 1H), 3.38-3.34 (m, 1H), 2.73-2.92 (m, 1H), 0.87 (d, J=1.7 Hz, 3H); $^{13}$C NMR (125 MHz, MeOD): 177.15, 157.75, 146.90, 145.78, 140.40, 134.47, 132.99, 129.82 (2C), 123.93, 116.20 (2C), 64.53, 39.92, 13.12 ppm.

Preparative Example 27: Preparation of N-(4-hydroxy-3-methylphenyl)-2-(hydroxymethyl)-4-methyl-N-phenylpent-4-enamide

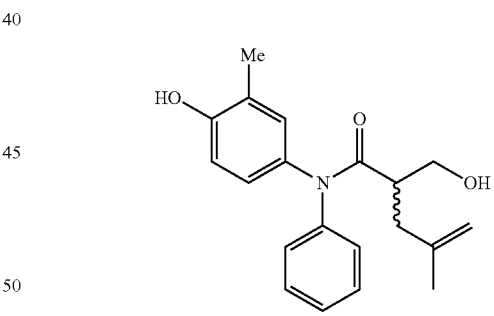

The target compound was prepared by the same manner as described in Preparative Example 1 except that 4-bromo-2-fluorophenol was used instead of 4-bromophenol in step 1, aniline was used instead of pyridine-3-amine in step 2, and 2-methyl-allylbromide was used instead of benzylbromide in step 4.

$^1$H NMR (600 Hz, MeOD): δ 7.44-7.16 (m, 5H), 7.12-6.95 (m, 2H), 6.79-6.67 (m, 1H), 4.82-4.79 (s, 1H), 4.76-4.72 (m, 1H), 3.83-3.76 (m, 1H), 3.52-3.46 (m, 1H), 3.09-3.02 (m, 1H), 2.41-2.34 (m, 1H), 2.18-2.12 (m, 3H), 2.09-2.05 (m, 1H), 1.54-1.45 (m, 3H); $^{13}$C NMR (150 Hz, MeOD): δ 177.35, 145.03, 144.23, 138.88, 138.52, 130.79, 130.12, 130.06 (2C), 128.09 (2C), 127.62, 116.22, 113.58 (2C), 64.88, 45.15, 39.22, 22.57, 16.31 ppm.

Preparative Example 28: Preparation of N-(3-fluoro-4-hydroxyphenyl)-2-(hydroxymethyl)-N-phenylpent-4-enamide

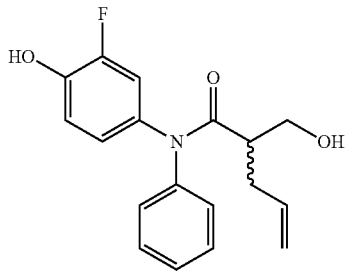 [SMILES: C=CCC(CO)C(=O)N(c1ccccc1)c1ccc(O)c(F)c1]

The target compound was prepared by the same manner as described in Preparative Example 1 except that 4-bromo-2-fluorophenol was used instead of 4-bromophenol in step 1, aniline was used instead of pyridine-3-amine in step 2, and 4-bromo-butyl-1-ene was used instead of benzylbromide in step 4.

$^1$H NMR (600 MHz, MeOD) δ 7.47-7.26 (m, 3H), 7.24 (s, 1H), 7.21 (d, J=7.6 Hz, 2H), 6.83-6.74 (m, 2H), 5.80-5.77 (m, 1H), 5.08-5.06 (t, J=12.6 Hz, 2H), 3.79-3.76 (m, 1H), 3.52 (dd, J=10.2, 5.5 Hz, 1H), 3.01-2.88 (m, 1H), 2.39-2.27 (m, 1H), 2.20-2.14 (m, 1H); $^{13}$C NMR (150 MHz, MeOD) δ 177.54, 154.62, 158.46, 144.75, 136.54, 135.36, 131.24, 130.60, 130.08 (2C), 129.36, 128.09 (2C), 116.61, 116.54, 64.52, 46.54, 35.12 ppm.

Preparative Example 29: Preparation of N-(4-hydroxy-3-methylphenyl)-2-(hydroxymethyl)-N-phenylpent-4-enamide

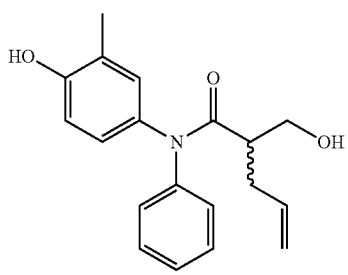 [SMILES: C=CCC(CO)C(=O)N(c1ccccc1)c1ccc(O)c(C)c1]

The target compound was prepared by the same manner as described in Preparative Example 1 except that 4-bromo-2-methylphenyl was used instead of 4-bromophenol in step 1, aniline was used instead of pyridine-3-amine in step 2, and 4-bromo-butyl-1-ene was used instead of benzylbromide in step 4.

$^1$H NMR (600 Hz, MeOD): δ 7.45-7.36 (m, 1H), 7.35-7.27 (m, 2H), 7.26-7.24 (m, 2H), 7.05-6.86 (m, 2H), 6.76-6.61 (m, 1H), 5.78-5.53 (m, 1H), 5.42-5.29 (m, 1H), 5.13-5.02 (m, 2H), 3.83-3.70 (m, 2H), 2.93-2.80 (m, 2H), 2.50-2.39 (m, 1H), 2.36-2.26 (m, 1H), 2.25-2.12 (m, 3H); $^{13}$C NMR (150 Hz, MeOD): δ 178.60, 140.45, 139.06, 136.41, 133.35, 132.50, 131.52, 129.98, 129.17, 127.90, 124.97, 122.49, 120.97, 110.36, 110.02, 77.93, 38.97, 30.89, 21.16 ppm.

Preparative Example 30: Preparation of 3-hydroxy-N-(4-hydroxyphenyl)-N,2-dimethylpropanamide

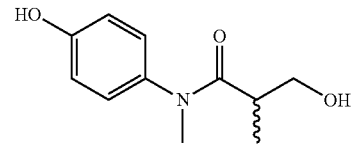

The target compound was prepared by the same manner as described in step 5 and step 6 except that iodomethane was used instead of benzylbromide in step 4 of Preparative Example 1.

$^1$H NMR (600 MHz, MeOD) δ 7.13-7.11 (m, 2H), 6.86 (d, J=8.9 Hz, 2H), 3.71 (dd, J=10.5, 8.3 Hz, 1H), 3.37 (dd, J=10.5, 5.8 Hz, 1H), 3.22 (s, 3H), 2.74-2.68 (m, 1H), 0.96 (d, J=6.9 Hz, 3H); $^{13}$C NMR (150 MHz, MeOD) δ 176.43, 157.13, 135.14, 128.20 (2C), 115.86 (2C), 64.37, 39.08, 36.65, 13.13 ppm.

Preparative Example 31: Preparation of 2-(hydroxymethyl)-N-(4-hydroxyphenyl)-N-methylpent-4-enamide

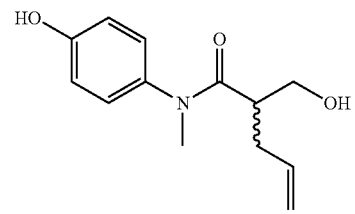 [SMILES: C=CCC(CO)C(=O)N(C)c1ccc(O)cc1]

The target compound was prepared by the same manner as described in step 5 and step 6 except that 3-bromo-pro-1-pene was used instead of benzylbromide in step 4 of Preparative Example 1.

$^1$H NMR (600 MHz, MeOD) δ 7.10 (d, J=8.5 Hz, 2H), 6.87-6.83 (m, 2H), 5.66-5.59 (m, 1H), 5.03-4.97 (m, 2H), 3.71 (dd, J=10.6, 8.3 Hz, 1H), 3.49-3.44 (m, 1H), 3.22 (s, 3H), 2.79-2.74 (m, 1H), 2.25-2.20 (m, 1H), 2.13-2.08 (m, 1H); $^{13}$C NMR (150 MHz, MeOD) δ 175.02, 157.08, 135.26 (2C), 134.99, 128.63, 115.74, 115.72 (2C), 63.08, 44.67, 36.72, 33.47 ppm.

Preparative Example 32: Preparation of 2-(hydroxymethyl)-N-(4-hydroxyphenyl)-N-methylhex-5-enamide

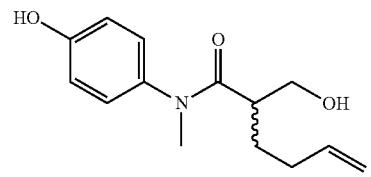 [SMILES: C=CCCC(CO)C(=O)N(C)c1ccc(O)cc1]

The target compound was prepared by the same manner as described in step 5 and step 6 except that 4-bromo-butyl-1-ene was used instead of benzylbromide in step 4 of Preparative Example 1.

¹H NMR (600 MHz, CDCl₃) δ 7.05 (d, J=8.6 Hz, 2H), 6.89 (d, J=8.7 Hz, 2H), 5.61-5.54 (m, 1H), 4.91-4.85 (m, 2H), 3.74-3.66 (m, 1H), 3.27 (s, J=4.6 Hz, 3H), 2.69-2.65 (m, 1H), 1.95-1.88 (m, 2H), 1.70-1.55 (m, 2H); ¹³C NMR (150 MHz, CDCl₃) δ 176.34, 156.20, 137.55, 135.52, 128.68, 116.50 (2C), 115.10 (2C), 63.27, 42.61, 37.79, 31.59, 31.12 ppm.

Preparative Example 33: Preparation of 2-(hydroxymethyl)-N-(4-hydroxyphenyl)-N,4-dimethyl-pent-4-enamide

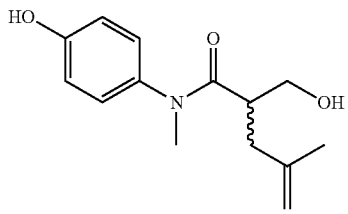 [SMILES: C=C(C)CC(CO)C(=O)N(C)c1ccc(O)cc1]

The target compound was prepared by the same manner as described in step 5 and step 6 except that 3-bromo-2-methylpro-1-pene was used instead of benzylbromide in step 4 of Preparative Example 1.

¹H NMR (600 MHz, MeOD) δ 7.09 (d, J=7.5 Hz, 2H), 6.85-6.82 (m, 2H), 4.70 (s, 1H), 4.63 (s, 1H), 3.73-3.68 (m, 1H), 3.42 (dd, J=10.5, 5.4 Hz, 1H), 3.20 (s, 3H), 2.90-2.84 (m, 1H), 2.23 (dd, J=13.4, 8.1 Hz, 1H), 1.99 (dd, J=13.4, 6.2 Hz, 1H), 1.45 (s, 3H); ¹³C NMR (150 MHz, MeOD) δ 174.11, 155.79, 141.30, 133.70, 127.35, 114.45 (2C), 110.44 (2C), 61.86, 41.89, 36.05, 35.46, 19.70 ppm.

Preparative Example 34: Preparation of 2-(4-fluorobenzyl)-3-hydroxy-N-(4-hydroxyphenyl)-N-methylpropanamide

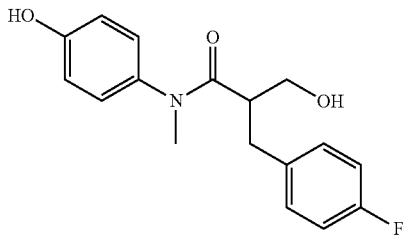 [SMILES: CN(C(=O)C(CO)Cc1ccc(F)cc1)c1ccc(O)cc1]

The target compound was prepared by the same manner as described in step 5 and step 6 except that 1-(bromomethyl)-4-fluorobenzene was used instead of benzylbromide in step 4 of Preparative Example 1.

¹H NMR (600 MHz, MeOD) δ 7.03-6.99 (m, 4H), 6.83-5.86 (m, 4H), 3.77 (dd, J=10.6, 8.1 Hz, 1H), 3.50 (dd, J=10.6, 5.9 Hz, 1H), 3.11 (s, 3H), 2.92-2.88 (m, 1H), 2.74 (dd, J=13.1, 10.1 Hz, 1H), 2.63 (dd, J=13.1, 4.9 Hz, 1H); ¹³C NMR (150 MHz, MeOD) δ 174.64, 162.51, 160.90, 156.94, 135.29, 135.27, 134.65, 130.40, 130.35, 128.33, 115.51, 114.62, 114.48, 63.25, 47.46, 36.60, 34.38 ppm.

Preparative Example 35: Preparation of 2-(4-bromobenzyl)-3-hydroxy-N-(4-hydroxyphenyl)-N-methylpropanamide

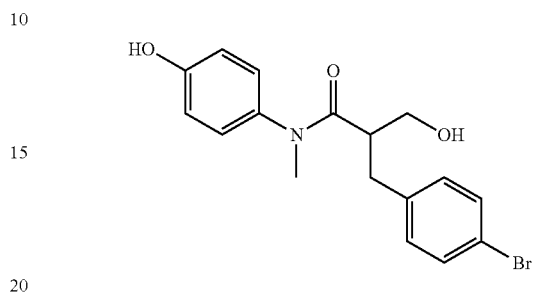

The target compound was prepared by the same manner as described in step 5 and step 6 except that 1-(bromomethyl)-4-bromobenzene was used instead of benzylbromide in step 4 of Preparative Example 1.

¹H NMR (600 MHz, MeOD) δ 7.47-7.36 (m, 2H), 6.96-6.92 (m, 2H), 6.85-6.47 (bs, 3H), 5.97 (bs, 1H), 3.77 (dd, J=10.6, 8.0 Hz, 1H), 3.50 (dd, J=10.6, 5.9 Hz, 1H), 3.11 (s, 3H), 2.91-2.86 (m, 1H), 2.73 (dd, J=13.0, 10.2 Hz, 1H), 2.62 (dd, J=13.0, 4.8 Hz, 1H); ¹³C NMR (150 MHz, MeOD) δ 174.49, 156.94, 138.64, 134.59, 131.07 (2C), 130.73 (2C), 128.27, 119.71 (2C), 115.52 (2C), 78.07, 63.25, 36.62, 34.61 ppm.

Preparative Example 36: Preparation of 2-(4-cyanobenzyl)-3-hydroxy-N-(4-hydroxyphenyl)-N-methylpropanamide

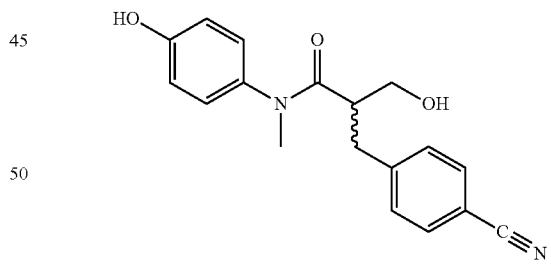

The target compound was prepared by the same manner as described in step 5 and step 6 except that 1-(bromomethyl)-4-thianobenzene was used instead of benzylbromide in step 4 of Preparative Example 1.

¹H NMR (600 MHz, MeOD) δ 7.65 (d, J=8.2 Hz, 2H), 7.21 (d, J=8.2 Hz, 2H), 6.86-6.57 (bs, 4H), 3.81-3.76 (m, 1H), 3.52 (dd, J=10.6, 6.0 Hz, 1H), 3.11 (s, 3H), 2.96-2.91 (m, 1H), 2.85 (dd, J=12.8, 10.1 Hz, 1H), 2.75 (dd, J=12.8, 4.7 Hz, 1H); ¹³C NMR (150 MHz, MeOD) δ 174.07, 157.03, 145.50, 134.47, 131.91 (2C), 129.84 (2C), 128.23, 118.36 (2C), 115.59 (2C), 109.88, 63.18, 47.14, 36.61, 35.23 ppm.

Preparative Example 37: Preparation of 3-hydroxy-N-(4-hydroxyphenyl)-N-methyl-2-(2-((phenylsulfonyl)methyl)benzyl)propanamide

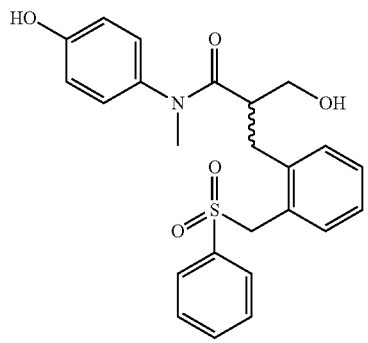 [SMILES: CN(C(=O)C(CO)Cc1ccccc1CS(=O)(=O)c1ccccc1)c1ccc(O)cc1]

The target compound was prepared by the same manner as described in step 5 and step 6 except that 1-(chloromethyl)-2-(phenylsulfonyl)benzene was used instead of benzylbromide in step 4 of Preparative Example 1.

$^1$H NMR (600 MHz, MeOD) δ 7.77-7.64 (m, 4H), 7.57-7.51 (m, 2H), 7.31-7.17 (m, 3H), 7.11 (dd, J=13.0, 6.2 Hz, 1H), 7.01 (dd, J=28.5, 7.6 Hz, 1H), 6.78-6.49 (m, 2H), 4.46 (d, J=14.2, 6.2 Hz, 1H), 4.29 (d, J=14.2 Hz, 1H), 3.70 (dd, J=10.5, 7.5 Hz, 1H), 3.45 (dd, J=10.6, 6.4 Hz, 1H), 3.04 (s, J=4.8 Hz, 3H), 2.82-2.76 (m, 1H), 2.66 (dd, J=13.8, 10.6 Hz, 1H), 2.58 (dd, J=13.8, 4.2 Hz, 1H); $^{13}$C NMR (150 MHz, MeOD) δ 174.42, 156.87, 139.94, 138.33, 134.46, 133.71, 132.47, 130.51, 128.85 (2C), 128.75 (2C), 128.26 (2C), 126.82, 126.29 (2C), 115.52 (2C), 63.23, 58.33, 46.82, 36.57, 31.63 ppm.

Preparative Example 38: Preparation of 2-(hydroxymethyl)-N-(4-hydroxyphenyl)-N-phenylpen-4-tinamide

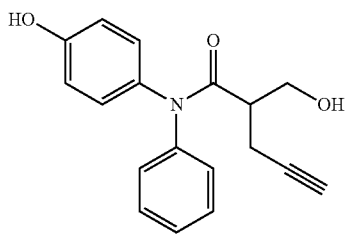 [SMILES: C#CCC(CO)C(=O)N(c1ccccc1)c1ccc(O)cc1]

The target compound was prepared by the same manner as described in Preparative Example 1 except that aniline was used instead of pyridine-3-amine in step 2 and 2-(bromomethyl)-1-chloro-4-(trifluoromethyl)benzene was used instead of benzylbromide in step 4.

$^1$H NMR (600 MHz, MeOD) δ 7.51-7.43 (m, 1H), 7.40-7.27 (m, 4H), 7.22 (t, J=7.2 Hz, 1H), 7.14 (d, J=8.5 Hz, 1H), 6.86 (d, J=8.6 Hz, 1H), 6.78 (d, J=8.5 Hz, 1H), 3.80 (dd, J=10.6, 7.7 Hz, 1H), 3.69-3.50 (m, 1H), 3.18-2.99 (m, 1H), 2.48 (dd, J=16.5, 9.1 Hz, 1H), 2.44 (d, J=16.7 Hz, 1H), 2.39-2.29 (m, 1H); $^{13}$C NMR (150 MHz, MeOD) δ 174.41, 157.25, 143.18, 133.97 (2C), 129.96 (2C), 128.60, 127.61, 126.53, 126.23, 115.80, 115.24, 80.96, 69.91, 62.72, 44.53, 18.14 ppm.

Preparative Example 39: Preparation of 3-hydroxy-N-(4-hydroxyphenyl)-N-isopropyl-2-methylpropanamide

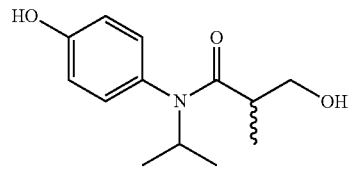 [SMILES: CC(CO)C(=O)N(c1ccc(O)cc1)C(C)C]

The target compound was prepared by the same manner as described in step 5 and step 6 except that 2-iodopropane was used instead of iodomethane in step 3 of reaction formula 4 of Preparative Example 4 and iodomethane was used instead of benzylbromode in step 4 of Preparative Example 1.

$^1$H NMR (600 MHz, MeOD) δ 7.06-7.00 (m, 2H), 6.89-6.85 (m, 2H), 4.94-4.91 (m, 1H), 3.71 (dd, J=10.5, 8.1 Hz, 1H), 3.35 (dd, J=10.5, 5.9 Hz, 1H), 2.52-2.45 (m, 1H), 1.05 (dd, J=9.3, 6.8 Hz, 6H), 0.94 (d, J=6.9 Hz, 3H); $^{13}$C NMR (150 MHz, MeOD) δ 175.88, 157.47, 131.60, 130.61, 129.06, 115.49, 115.17, 64.35, 45.97, 40.04, 19.86, 19.79, 13.23 ppm.

Preparative Example 40: Preparation of 2-(hydroxymethyl)-N-(4-hydroxyphenyl)-N-isopropyl-pent-4-enamide

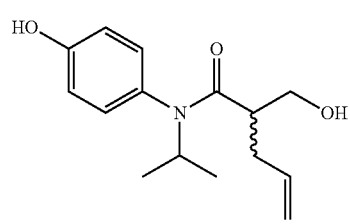 [SMILES: C=CCC(CO)C(=O)N(c1ccc(O)cc1)C(C)C]

The target compound was prepared by the same manner as described in step 5 and step 6 except that 2-iodopropane was used instead of iodomethane in step 3 of reaction formula 4 of Preparative Example 4 and 3-bromopro-1-pane was used instead of benzylbromode in step 4 of Preparative Example 1.

$^1$H NMR (600 MHz, MeOD) δ 7.05-7.02 (m, 1H), 6.98-6.96 (m, 1H), 6.88-6.84 (m, 2H), 5.66-5.59 (m, 1H), 5.02-4.97 (m, 2H), 4.95-4.91 (m, 1H), 3.70 (dd, J=10.6, 8.1 Hz, 1H), 3.43 (dd, J=10.6, 5.8 Hz, 1H), 2.56-2.52 (m, 1H), 2.25-2.19 (m, 1H), 2.12-2.06 (m, 1H), 1.07 (d, J=6.8 Hz, 3H), 1.02 (d, J=6.8 Hz, 3H); $^{13}$C NMR (150 MHz, MeOD) δ 174.36, 157.43, 135.35, 131.84, 131.24, 128.90, 115.71, 115.38, 114.95, 63.08, 46.15, 45.52, 33.57, 20.10, 19.72 ppm.

Preparative Example 41: Preparation of 2-(4-fluorobenzyl)-3-hydroxy-N-(4-hydroxyphenyl)-N-isopropylpropanamide

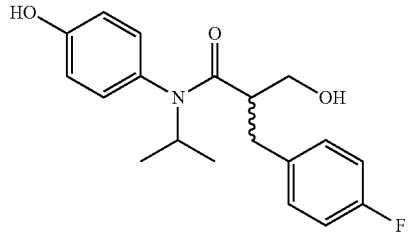 [SMILES: CC(C)N(C(=O)C(CO)Cc1ccc(F)cc1)c1ccc(O)cc1]

The target compound was prepared by the same manner as described in step 5 and step 6 except that 2-iodopropane was used instead of iodomethane in step 3 of reaction formula 4 of Preparative Example 4 and 1-bromo-4-fluorobenzene was used instead of benzylbromode in step 4 of Preparative Example 1.

$^1$H NMR (600 MHz, MeOD) δ 7.06-6.92 (m, 5H), 6.79 (dd, J=8.5, 2.8 Hz, 1H), 6.57 (dd, J=8.5, 2.8 Hz, 1H), 5.70 (dd, J=8.5, 2.6 Hz, 1H), 4.88-4.86 (m, 1H). 3.74 (dd, J=10.5, 7.5 Hz, 1H), 3.48 (dd, J=10.6, 5.8 Hz, 1H), 2.78-2.72 (m, 1H), 2.70-2.59 (m, 2H), 0.96-0.87 (m, 6H); $^{13}$C NMR (150 MHz, MeOD) δ 173.94, 162.54, 160.93, 157.27, 135.39, 131.65, 130.80, 130.66, 128.48, 115.16, 114.71, 114.56, 114.42, 63.35, 48.55, 46.00, 34.44, 19.82, 19.63 ppm.

Preparative Example 42: Preparation of 3-hydroxy-N-(4-hydroxyphenyl)-N-isopropyl-2-(4-(trifluoromethyl)benzyl)propanamide

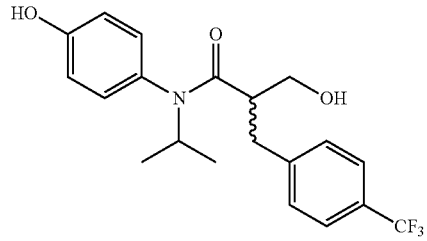 [SMILES: CC(C)N(C(=O)C(CO)Cc1ccc(C(F)(F)F)cc1)c1ccc(O)cc1]

The target compound was prepared by the same manner as described in step 5 and step 6 except that 2-iodopropane was used instead of iodomethane in step 3 of reaction formula 4 of Preparative Example 4 and 1-bromo-4-(trifluoromethyl)benzene was used instead of benzylbromode in step 4 of Preparative Example 1.

$^1$H NMR (600 MHz, MeOD) δ 7.59 (d, J=8.1 Hz, 2H), 7.23 (d, J=8.0 Hz, 2H), 6.95 (dd, J=8.5, 2.6 Hz, 1H), 6.79 (dd, J=8.5, 2.9 Hz, 1H), 6.51 (dd, J=8.5, 2.9 Hz, 1H), 5.57 (dd, J=8.5, 2.6 Hz, 1H), 4.89-4.85 (m, 1H), 3.79-3.75 (m, 1H), 3.53-3.50 (m, 1H), 2.88-2.83 (m, 1H), 2.76-2.72 (m, 1H), 2.72-2.66 (m, 1H), 0.93 (d, J=6.8 Hz, 3H), 0.88 (d, J=6.7 Hz, 3H); $^{13}$C NMR (150 MHz, MeOD) δ 173.62, 157.31, 144.26, 131.69, 130.49, 129.65 (2C), 128.55, 128.37, 128.34, 124.84, 124.81, 115.24, 114.66, 63.34, 48.37, 46.11, 35.06, 19.80, 19.58 ppm.

Preparative Example 43: Preparation of 2-(4-cyanobenzyl)-3-hydroxy-N-(4-hydroxyphenyl)-N-isopropylpropanamide

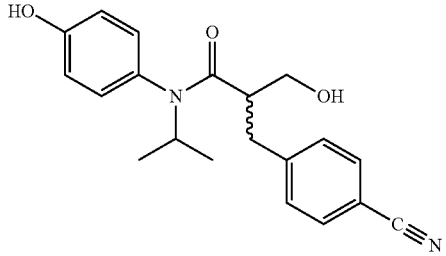 [SMILES: CC(C)N(C(=O)C(CO)Cc1ccc(C#N)cc1)c1ccc(O)cc1]

The target compound was prepared by the same manner as described in step 5 and step 6 except that 2-iodopropane was used instead of iodomethane in step 3 of reaction formula 4 of Preparative Example 4 and 4-bromobenzonitrile was used instead of benzylbromode in step 4 of Preparative Example 1.

$^1$H NMR (600 MHz, MeOD) δ 7.68-7.65 (m, 2H), 7.23 (d, J=8.2 Hz, 2H), 6.97 (dd, J=8.5, 2.6 Hz, 1H), 6.80 (dd, J=8.5, 2.9 Hz, 1H), 6.59 (dd, J=8.5, 2.9 Hz, 1H), 5.73 (dd, J=8.5, 2.6 Hz, 1H), 4.86 (dd, J=13.6, 6.8 Hz, 1H), 3.76 (dd, J=10.6, 7.5 Hz, 1H), 3.50 (dd, J=10.6, 6.3 Hz, 1H), 2.86 (dd, J=12.7, 10.4 Hz, 1H), 2.77-2.67 (m, 2H), 0.94 (d, J=6.8 Hz, 3H), 0.90 (d, J=6.7 Hz, 3H); $^{13}$C NMR (150 MHz, MeOD) δ 173.40, 157.40, 145.63, 131.85 (2C), 131.69, 130.50, 130.10 (2C), 128.37, 118.35, 115.31, 114.78, 109.87, 63.26, 48.09, 46.17, 35.28, 19.87, 19.59 ppm.

Preparative Example 44: Preparation of 2-(2-fluoro-6-(trifluoromethyl)benzyl)-3-hydroxy-N-(4-hydroxyphenyl)-N-isopropylpropanamide

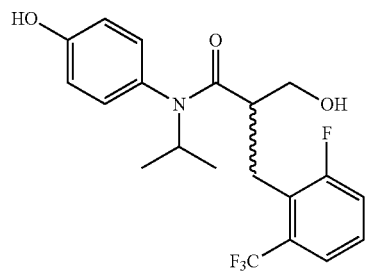 [SMILES: CC(C)N(C(=O)C(CO)Cc1c(F)cccc1C(F)(F)F)c1ccc(O)cc1]

The target compound was prepared by the same manner as described in step 5 and step 6 except that 2-iodopropane was used instead of iodomethane in step 3 of reaction formula 4 of Preparative Example 4 and 2-bromo-1-fluoro-3-(trifluoromethyl)benzene was used instead of benzylbromode in step 4 of Preparative Example 1.

$^1$H NMR (600 MHz, MeOD) δ 7.54-7.49 (m, 2H), 7.38-7.34 (m, 1H), 6.93 (dd, J=8.5, 2.6 Hz, 1H), 6.78 (dd, J=8.5, 2.9 Hz, 1H), 6.41 (dd, J=8.5, 2.9 Hz, 1H), 5.68 (dd, J=8.5, 2.6 Hz, 1H), 4.94-4.91 (m, 1H), 3.84 (dd, J=10.4, 9.1 Hz, 1H), 3.47 (dd, J=10.6, 5.5 Hz, 1H), 3.08 (dd, J=13.8, 9.7 Hz, 1H), 2.87-2.82 (m, 1H), 2.75 (d, J=14.0 Hz, 1H), 0.96 (dd, J=6.7, 5.4 Hz, 6H); $^{13}$C NMR (150 MHz, MeOD) δ 173.87, 162.86, 161.22, 157.10, 131.92, 130.11, 128.46, 128.39, 125.60, 121.81, 119.15, 118.99, 115.24, 114.57, 63.72, 46.14, 45.89, 24.99, 19.78, 19.51 ppm.

Preparative Example 45: Preparation of 2-(3-bromobenzyl)-3-hydroxy-N-(4-hydroxyphenyl)-N-isopropylamide

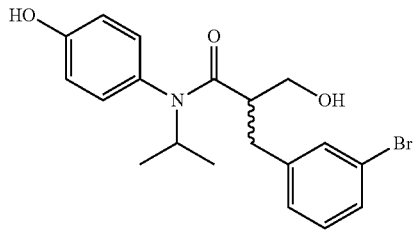 [SMILES: CC(C)N(C(=O)C(CO)Cc1cccc(Br)c1)c1ccc(O)cc1]

The target compound was prepared by the same manner as described in step 5 and step 6 except that 2-iodopropane was used instead of iodomethane in step 3 of reaction formula 4 of Preparative Example 4 and 1,3-dibromobenzene was used instead of benzylbromode in step 4 of Preparative Example 1.

$^1$H NMR (600 MHz, MeOD) δ 7.45 (dd, J=8.0, 0.9 Hz, 1H), 7.23-7.20 (m, 2H), 7.03 (d, J=7.7 Hz, 1H), 6.94 (dd, J=8.5, 2.6 Hz, 1H), 6.79 (dd, J=8.5, 2.9 Hz, 1H), 6.59 (dd, J=8.5, 2.9 Hz, 1H), 5.57 (dd, J=8.5, 2.6 Hz, 2H), 4.86-4.85 (m, 1H), 4.84-4.81 (m, 1H), 3.75 (dd, J=10.6, 7.4 Hz, 2H), 3.50 (dd, J=10.6, 5.9 Hz, 2H), 2.77-2.70 (m, 1H), 2.69-2.62 (m, 2H), 0.93 (d, J=6.8 Hz, 3H), 0.89 (d, J=6.7 Hz, 3H); $^{13}$C NMR (150 MHz, MeOD) δ 173.65, 157.30, 142.14, 132.02, 131.61, 130.77, 129.81, 129.09, 128.34, 127.95, 121.90, 115.17, 114.72, 63.41, 48.43, 46.03, 34.92, 19.93, 19.59 ppm.

Preparative Example 46: Preparation of 3-hydroxy-N-(4-hydroxyphenyl)-N-isopropyl-2-(4-nitrobenzyl)propanamide

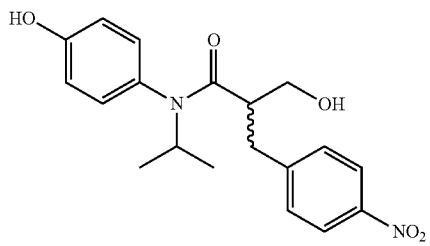 [SMILES: CC(C)N(C(=O)C(CO)Cc1ccc([N+](=O)[O-])cc1)c1ccc(O)cc1]

The target compound was prepared by the same manner as described in step 5 and step 6 except that 2-iodopropane was used instead of iodomethane in step 3 of reaction formula 4 of Preparative Example 4 and 1-bromo-4-nitrobenzene was used instead of benzylbromode in step 4 of Preparative Example 1.

$^1$H NMR (600 MHz, MeOD) δ 8.18 (d, J=8.7 Hz, 2H), 7.28 (d, J=8.7 Hz, 2H), 6.98 (dd, J=8.5, 2.6 Hz, 1H), 6.81 (dd, J=8.5, 2.9 Hz, 1H), 6.57 (dd, J=8.5, 2.9 Hz, 1H), 5.76 (dd, J=8.5, 2.6 Hz, 1H), 4.87-4.84 (m, 1H), 3.77 (dd, J=10.6, 7.5 Hz, 1H), 3.51 (dd, J=10.6, 6.3 Hz, 1H), 2.91 (dd, J=12.8, 10.4 Hz, 1H), 2.80 (dd, J=12.8, 4.5 Hz, 1H), 2.76-2.69 (m, 1H), 0.94 (d, J=6.8 Hz, 3H), 0.89 (d, J=6.7 Hz, 3H); $^{13}$C NMR (150 MHz, MeOD) δ 173.34, 157.42, 147.63, 146.76, 131.69, 130.48, 130.09 (2C), 128.37, 123.03 (2C), 115.35, 114.81, 63.25, 48.08, 46.22, 34.97, 19.88, 19.58 ppm.

Based on the above Preparative Examples 1-46, the compounds of Examples 1~49 were prepared by cyclization.

Example 1: Preparation of 5-phenyl-1-oxa-5-azaspiro[5,5]undeca-7,10-diene-4,9-dione

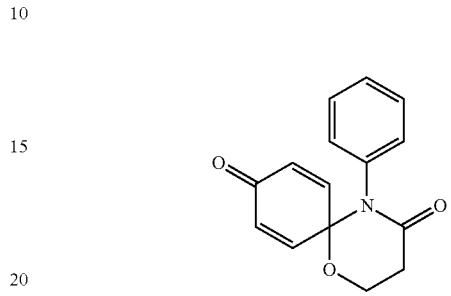

The target compound was obtained by cyclization performed by the same manner as described in Example 19 except that the compound of Preparative Example 14 was used instead of the compound of Preparative Example 1 as the starting material in Example 19.

$^1$H NMR (600 MHz, CDCl$_3$) δ 7.37-7.29 (m, 3H), 7.09-7.04 (m, 2H), 7.02-6.93 (m, 2H), 6.09 (d, J=10.2 Hz, 2H), 4.33 (t, J=6.0 Hz, 2H), 2.85 (t, J=6.0 Hz, 2H); $^{13}$C NMR (150 MHz, CDCl$_3$) δ 183.94, 167.19, 143.71 (2C), 136.32, 129.87 (2C), 129.81 (2C), 129.14, 129.09, 129.02, 83.07, 60.26, 32.82 ppm.

Example 2: Preparation of 3-methyl-5-phenyl-1-oxa-5-azaspiro[5,5]undeca-7,10-diene-4,9-dione

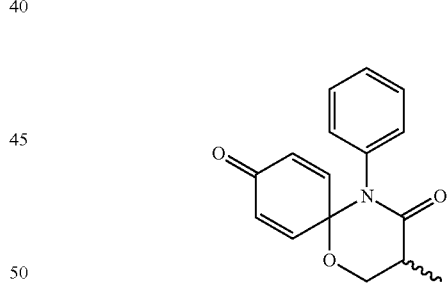

The target compound was obtained by cyclization performed by the same manner as described in Example 19 except that the compound of Preparative Example 5 was used instead of the compound of Preparative Example 1 as the starting material in Example 19.

$^1$H NMR (600 MHz, CDCl$_3$) δ 7.55 (d, J=8.0 Hz, 1H), 7.40-7.30 (m, 3H), 7.11-7.05 (m, 2H), 6.94 (dd, J=10.2, 3.2 Hz, 1H), 6.12 (dd, J=10.2, 2.0 Hz, 1H), 6.08 (dd, J=10.2, 2.0 Hz, 1H), 4.32 (dd, J=11.9, 5.5 Hz, 1H), 4.06 (dd, J=11.9, 7.8 Hz, 1H), 2.98-2.88 (m, 1H), 1.39 (d, J=7.2 Hz, 3H); $^{13}$C NMR (150 MHz, CDCl$_3$) δ 184.09, 171.21, 144.51, 143.52, 136.60, 130.05, 129.81, 129.79, 129.17, 129.11, 129.05, 120.02, 83.53, 66.14, 37.29, 13.72 ppm.

Example 3: Preparation of 3-allyl-5-phenyl-1-oxa-5-azaspiro[5,5]undeca-7,10-diene-4,9-dione

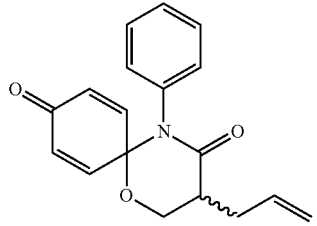 [SMILES: C=CCC1COC2(C=CC(=O)C=C2)N(c2ccccc2)C1=O]

The target compound was obtained by cyclization performed by the same manner as described in Example 19 except that the compound of Preparative Example 6 was used instead of the compound of Preparative Example 1 as the starting material in Example 19.

$^1$H NMR (600 MHz, CDCl$_3$) δ 7.34-7.29 (m, 3H), 7.06-7.03 (m, 2H), 7.01 (dd, J=10.2, 3.2 Hz, 1H), 6.95 (dd, J=10.2, 3.2 Hz, 1H), 6.12-6.03 (m, 2H), 5.91-5.80 (m, 1H), 5.23-5.14 (m, 2H), 4.29 (dd, J=12.2, 5.5 Hz, 1H), 4.13 (dd, J=12.2, 7.0 Hz, 1H), 2.89-2.81 (m, 1H), 2.75-2.69 (m, 1H), 2.57-2.50 (m, 1H); $^{13}$C NMR (150 MHz, CDCl$_3$) δ 183.84, 169.72, 143.89, 143.52, 136.34, 135.13, 134.44, 129.76, 129.64, 128.97, 128.87, 124.29, 119.91, 118.19, 117.60, 83.11, 63.33, 41.24, 33.09 ppm.

Example 4: Preparation of 3-(2-methyl-allyl)-5-phenyl-1-oxa-5-azaspiro[5,5]undeca-7,10-diene-4,9-dione

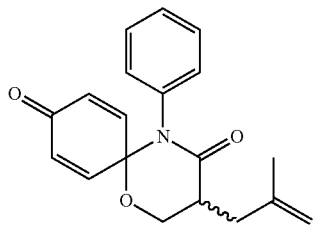 [SMILES: C=C(C)CC1COC2(C=CC(=O)C=C2)N(c2ccccc2)C1=O]

The target compound was obtained by cyclization performed by the same manner as described in Example 19 except that the compound of Preparative Example 15 was used instead of the compound of Preparative Example 1 as the starting material in Example 19.

1H NMR (600 MHz, CDCl$_3$) δ 7.32-7.29 (m, 3H), 7.06-7.02 (m, 2H), 7.01 (dd, J=10.0, 3.2 Hz, 1H), 6.97 (dd, J=10.0, 3.1 Hz, 1H), 6.11-6.05 (m, 2H), 4.86 (d, J=44.8 Hz, 2H), 4.25 (dd, J=12.2, 5.2 Hz, 1H), 4.08 (dd, J=12.2, 6.6 Hz, 1H), 2.95-2.88 (m, 1H), 2.78 (dd, J=14.1, 3.7 Hz, 1H), 2.41 (dd, J=14.0, 11.0 Hz, 1H), 1.79 (s, 3H); $^{13}$C NMR (150 MHz, CDCl$_3$) δ 183.95, 170.25, 143.97, 143.73, 141.82, 136.49, 129.90, 129.75, 129.06, 128.94, 113.59, 83.23, 77.25, 77.04, 76.83, 63.35, 39.85, 37.10, 21.92 ppm.

Example 5: Preparation of 3-(3-butenyl)-5-phenyl-1-oxa-5-azaspiro[5,5]undeca-7,10-diene-4,9-dione

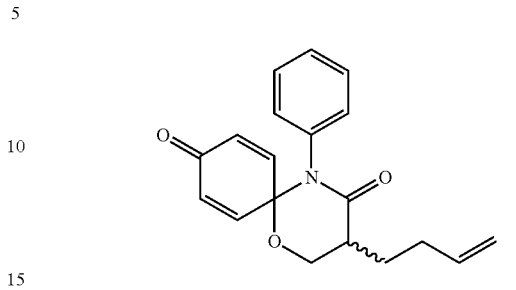

The target compound was obtained by cyclization performed by the same manner as described in Example 19 except that the compound of Preparative Example 16 was used instead of the compound of Preparative Example 1 as the starting material in Example 19.

$^1$H NMR (600 MHz, CDCl$_3$) δ 7.33-7.29 (m, 3H), 7.07-7.02 (m, 2H), 7.01 (dd, J=10.2, 3.2 Hz, 1H), 6.95 (dd, J=10.2, 3.2 Hz, 1H), 6.11-6.02 (m, 2H), 5.88-5.80 (m, 1H), 5.13-5.09 (m, 1H), 5.06-5.03 (m, 1H), 4.32 (dd, J=12.0, 5.3 Hz, 1H), 4.11 (dd, J=12.1, 6.9 Hz, 1H), 2.79 (m, 1H), 2.32-2.19 (m, 2H), 2.17-2.07 (m, 1H), 1.83-1.75 (m, 1H); $^{13}$C NMR (150 MHz, CDCl$_3$) δ 183.76, 170.25, 143.88, 143.47, 137.22, 136.31, 129.74 (2C), 129.55, 129.51, 128.87 (2C), 128.74, 115.60, 82.97, 63.78, 41.13, 30.94, 27.80 ppm.

Example 6: Preparation of 3-benzyl-5-phenyl-1-oxa-5-azaspiro[5,5]undeca-7,10-diene-4,9-dione

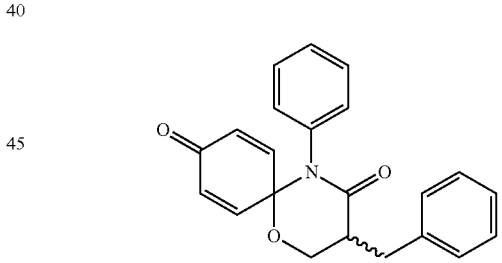

The target compound was obtained by cyclization performed by the same manner as described in Example 19 except that the compound of Preparative Example 3 was used instead of the compound of Preparative Example 1 as the starting material in Example 19.

$^1$H NMR (600 MHz, CDCl$_3$) δ 7.39-7.26 (m, 8H), 7.05-7.01 (m, 2H), 6.92 (dd, J=10.4, 3.2 Hz, 1H), 6.66 (dd, J=10.4, 3.2 Hz, 1H), 6.05-5.99 (m, 2H), 4.18 (dd, J=12.2, 5.2 Hz, 1H), 4.06 (dd, J=12.2, 6.4 Hz, 1H), 3.29 (dd, J=13.2, 3.5 Hz, 1H), 3.16-3.01 (m, 2H); $^{13}$C NMR (151 MHz, CDCl$_3$) δ 183.87, 169.67, 143.76, 143.57, 138.02, 136.42, 129.84, 129.72, 129.68, 129.40, 129.06, 128.97, 128.93, 128.90, 128.78, 128.67, 126.87, 120.08, 83.16, 63.10, 43.37, 34.94 ppm.

Example 7: Preparation of 3-(4-fluoro-benzyl)-5-phenyl-1-oxa-5-azaspiro[5,5]undeca-7,10-diene-4,9-dione

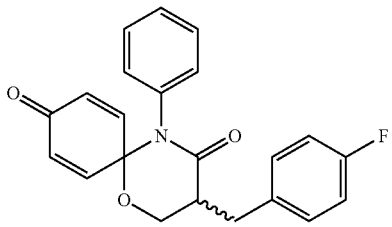 [SMILES: O=C1C=CC2(C=C1)OCC(Cc1ccc(F)cc1)C(=O)N2c1ccccc1]

The target compound was obtained by cyclization performed by the same manner as described in Example 19 except that the compound of Preparative Example 8 was used instead of the compound of Preparative Example 1 as the starting material in Example 19.

$^1$H NMR (600 MHz, CDCl$_3$) δ 7.34-7.29 (m, 3H), 7.27-7.21 (m, 2H), 7.08-6.97 (m, 4H), 6.92 (dd, J=10.3, 2.9 Hz, 1H), 6.73-6.68 (m, 1H), 6.04 (d, J=10.2 Hz, 2H), 4.18 (dd, J=12.2, 5.2 Hz, 1H), 4.04 (dd, J=12.2, 6.5 Hz, 1H), 3.25 (dd, J=13.7, 3.8 Hz, 1H), 3.11-3.05 (m, 1H), 3.04-2.98 (m, 1H); $^{13}$C NMR (150 MHz, CDCl$_3$) δ 183.65, 169.37, 162.46, 160.84, 143.51, 143.24, 136.16, 133.49, 130.72, 130.67, 129.66 (2C), 129.60, 128.93 (2C), 128.87, 115.42, 115.28, 83.05, 62.81, 43.28, 33.89 ppm.

Example 8: Preparation of 3-(4-chloro-benzyl)-5-phenyl-1-oxa-5-azaspiro[5,5]undeca-7,10-diene-4,9-dione

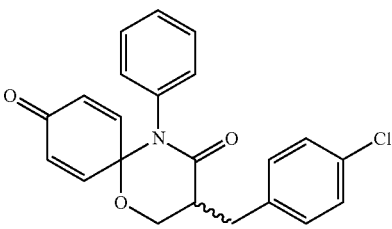 [SMILES: O=C1C=CC2(C=C1)OCC(Cc1ccc(Cl)cc1)C(=O)N2c1ccccc1]

The target compound was obtained by cyclization performed by the same manner as described in Example 19 except that the compound of Preparative Example 17 was used instead of the compound of Preparative Example 1 as the starting material in Example 19.

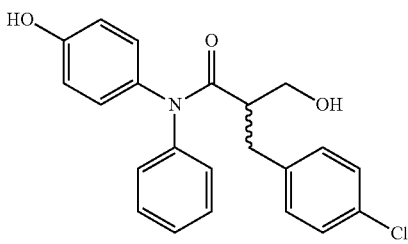 [SMILES: O=C(C(CO)Cc1ccc(Cl)cc1)N(c1ccccc1)c1ccc(O)cc1]

$^1$H NMR (600 MHz, CDCl$_3$) δ 7.38-7.29 (bs, 5H), 7.22 (d, J=7.8 Hz, 2H), 7.04-6.94 (bs, 2H), 6.92 (d, J=9.8 Hz, 1H), 6.73 (d, J=9.0 Hz, 1H), 6.05 (d, J=10.1 Hz, 2H), 4.18 (dd, J=12.2, 4.2 Hz, 1H), 4.02 (dd, J=11.8, 6.3 Hz, 1H), 3.25 (d, J=13.2 Hz, 1H), 3.08-2.97 (m, 2H); $^{13}$C NMR (150 MHz, CDCl$_3$) δ 183.86, 169.54, 143.70, 143.41, 136.55, 136.34, 132.80, 130.76 (2C), 129.90, 129.87 (2C), 129.84, 129.16 (2C), 129.11, 128.87 (2C), 83.30, 62.99, 43.39, 34.23 ppm.

Example 9: Preparation of 3-(3-bromo-benzyl)-5-phenyl-1-oxa-5-azaspiro[5,5]undeca-7,10-diene-4,9-dione

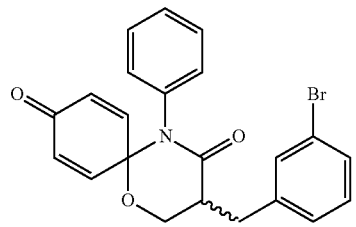 [SMILES: O=C1C=CC2(C=C1)OCC(Cc1cccc(Br)c1)C(=O)N2c1ccccc1]

The target compound was obtained by cyclization performed by the same manner as described in Example 19 except that the compound of Preparative Example 18 was used instead of the compound of Preparative Example 1 as the starting material in Example 19.

$^1$H NMR (600 MHz, CDCl$_3$) δ 7.44 (d, J=8.2 Hz, 1H), 7.44-7.40 (m, 1H), 7.33-7.29 (m, 3H), 7.24-7.19 (m, 2H), 7.04-7.01 (m, 2H), 6.93 (dd, J=10.4, 3.2 Hz, 1H), 6.69 (dd, J=10.4, 3.2 Hz, 1H), 4.19 (dd, J=12.3, 5.1 Hz, 1H), 4.03 (dd, J=12.3, 6.3 Hz, 1H), 3.25 (dd, J=12.7, 3.0 Hz, 1H), 3.09-2.99 (m, 2H); $^{13}$C NMR (150 MHz, CDCl$_3$) δ 183.81, 169.37, 143.62, 143.37, 140.47, 136.29, 132.28, 130.25, 130.06, 129.88 (2C), 129.85, 129.80, 129.11 (2C), 129.06, 128.06, 122.75, 83.25, 63.00, 43.21, 34.58 ppm.

Example 10: Preparation of 3-(4-bromo-benzyl)-5-phenyl-1-oxa-5-azaspiro[5,5]undeca-7,10-diene-4,9-dione

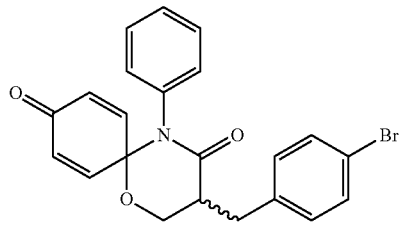 [SMILES: O=C1C=CC2(C=C1)OCC(Cc1ccc(Br)cc1)C(=O)N2c1ccccc1]

The target compound was obtained by cyclization performed by the same manner as described in Example 19 except that the compound of Preparative Example 9 was used instead of the compound of Preparative Example 1 as the starting material in Example 19.

$^1$H-NMR (600 MHz, CDCl$_3$) δ 7.54-7.49 (m, 1H), 7.47-7.43 (m, 1H), 7.42-7.35 (m, 5H), 7.31-7.26 (m, 2H), 7.14-7.06 (m, 2H), 6.72 (d, J=10.5 Hz 1H), 6.03 (d, J=10.3 Hz 1H), 4.21-4.13 (m, 1H), 4.07-3.96 (m, 2H), 3.08-2.99 (m, 2H), 2.87-2.78 (m, 1H) ppm.

Example 11: Preparation of 3-(4-trifluoromethyl-benzyl)-5-phenyl-1-oxa-5-azaspiro[5,5]undeca-7,10-diene-4,9-dione

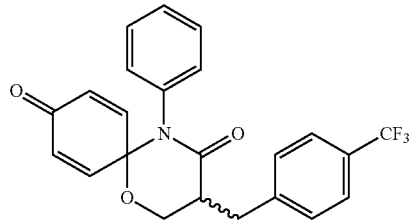 [SMILES: O=C1C=CC2(C=C1)OCC(Cc1ccc(C(F)(F)F)cc1)C(=O)N2c1ccccc1]

The target compound was obtained by cyclization performed by the same manner as described in Example 19 except that the compound of Preparative Example 7 was used instead of the compound of Preparative Example 1 as the starting material in Example 19.

$^1$H NMR (600 MHz, CDCl$_3$) δ 7.48 (d, J=7.3 Hz, 2H), 7.32 (bs, 3H), 7.16 (d, J=7.5 Hz, 2H), 7.02 (bs, 2H), 6.92 (d, J=10.4 Hz, 1H), 6.74 (d, J=10.0 Hz, 1H), 6.05 (d, J=10.1 Hz, 2H), 4.17 (d, J=11.0 Hz, 1H), 4.05-3.99 (m, 1H), 3.24 (d, J=12.2 Hz, 1H), 3.09-2.97 (m, 2H); $^{13}$C NMR (150 MHz, CDCl$_3$) δ 183.84, 169.49, 143.68, 143.38, 137.07, 136.63, 136.32, 131.82 (2C), 131.12 (2C), 129.89, 129.86 (2C), 129.84, 129.15 (2C), 129.10, 120.82, 83.29, 62.98, 43.33, 34.27 ppm.

Example 12: Preparation of 3-(4-nitro-benzyl)-5-phenyl-1-oxa-5-azaspiro[5,5]undeca-7,10-diene-4,9-dione

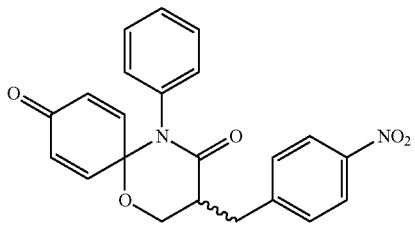 [SMILES: O=C1C=CC2(C=C1)OCC(Cc1ccc([N+](=O)[O-])cc1)C(=O)N2c1ccccc1]

The target compound was obtained by cyclization performed by the same manner as described in Example 19 except that the compound of Preparative Example 19 was used instead of the compound of Preparative Example 1 as the starting material in Example 19.

$^1$H NMR (600 MHz, CDCl$_3$) δ 8.22 (d, J=8.4 Hz, 2H), 7.47 (d, J=8.3 Hz, 2H), 7.40-7.29 (m, 3H), 7.02 (d, J=3.4 Hz, 2H), 6.93 (d, J=8.3 Hz, 1H), 6.79 (d, J=9.7 Hz, 1H), 6.07 (d, J=10.1 Hz, 2H), 4.21 (dd, J=12.1, 5.0 Hz, 1H), 4.02 (dd, J=12.1, 6.8 Hz, 1H), 3.41 (dd, J=13.6, 3.9 Hz, 1H), 3.17 (dd, J=13.4, 9.3 Hz, 1H), 3.14-3.07 (m, 1H); $^{13}$C NMR (151 MHz, CDCl$_3$) δ 183.73, 169.13, 146.05, 143.50, 143.05, 136.16, 130.24 (2C), 130.07, 130.03, 129.94, 129.84 (2C), 129.25, 129.24, 129.09, 123.97 (2C), 83.44, 63.00, 43.30, 34.65 ppm.

Example 13: Preparation of 3-(2-((phenylsulfonyl)methyl)-benzyl)-5-phenyl-1-oxa-5-azaspiro[5,5]undeca-7,10-diene-4,9-dione

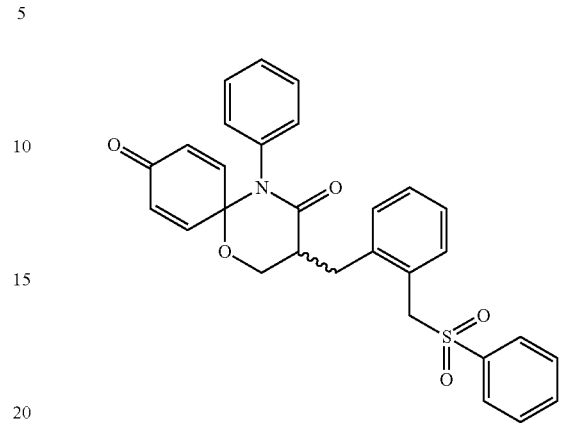

The target compound was obtained by cyclization performed by the same manner as described in Example 19 except that the compound of Preparative Example 20 was used instead of the compound of Preparative Example 1 as the starting material in Example 19.

$^1$H NMR (600 MHz, CDCl$_3$) δ 7.78 (d, J=7.0 Hz, 2H), 7.63 (t, J=6.5 Hz, 1H), 7.50 (d, J=7.4 Hz, 2H), 7.41-7.27 (m, 5H), 7.25-7.16 (m, 2H), 7.05 (s, 2H), 6.98 (d, J=10.1 Hz, 1H), 6.91 (d, J=10.0 Hz, 1H), 6.10-6.06 (m, 2H), 4.53 (s, 2H), 4.20 (d, J=11.9 Hz, 1H), 4.03 (d, J=11.5 Hz, 1H), 3.31 (d, J=12.4 Hz, 1H), 3.04-2.92 (m, 2H); $^{13}$C NMR (150 MHz, CDCl$_3$) δ 183.88, 169.82, 143.87, 143.35, 138.89, 138.63, 136.32, 133.88, 132.93, 130.58, 129.95 (3C), 129.85, 129.31, 129.14 (2C), 129.10 (2C), 128.54 (2C), 127.20 (2C), 126.82, 83.37, 62.91, 59.33, 43.46, 31.61 ppm.

Example 14: Preparation of 3-(3,5-ditrifluoromethyl-benzyl)-5-phenyl-1-oxa-5-azaspiro[5,5]undeca-7,10-diene-4,9-dione

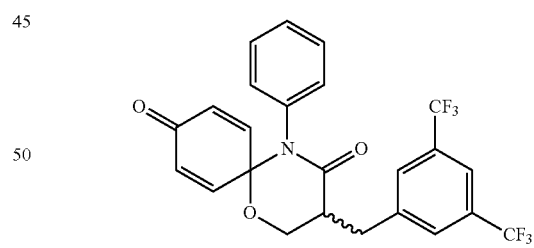

The target compound was obtained by cyclization performed by the same manner as described in Example 19 except that the compound of Preparative Example 21 was used instead of the compound of Preparative Example 1 as the starting material in Example 19.

$^1$H NMR (600 MHz, CDCl$_3$) δ 7.82 (s, 1H), 7.76 (s, 2H), 7.36-7.29 (m, 3H), 7.05-6.98 (m, 2H), 6.94 (dd, J=10.0, 3.1 Hz, 1H), 6.74 (dd, J=10.0, 2.8 Hz, 1H), 6.07 (t, J=10.3 Hz, 2H), 4.23 (dd, J=12.3, 5.1 Hz, 1H), 4.03 (dd, J=12.2, 6.7 Hz, 1H), 3.43 (dd, J=14.0, 4.3 Hz, 1H), 3.21 (dd, J=14.0, 8.8 Hz, 1H), 3.15-3.07 (m, 1H); $^{13}$C NMR (150 MHz, CDCl$_3$) δ 183.68, 168.93, 143.36, 142.95, 140.91, 136.08, 132.38, 132.16, 131.94, 131.72, 130.05, 129.81, 129.48, 129.46, 129.23, 129.21, 125.92, 124.11, 122.30, 121.03, 83.43, 62.93, 43.23, 34.55 ppm.

Example 15: Preparation of 3-(3,5-dimethyl-benzyl)-5-phenyl-1-oxa-5-azaspiro[5,5]undeca-7,10-diene-4,9-dione

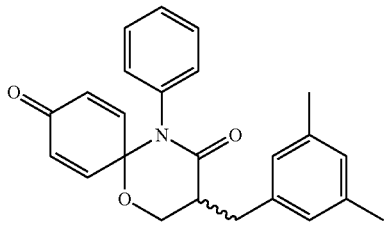 [SMILES: Cc1cc(C)cc(CC2COC3(C=CC(=O)C=C3)N(c3ccccc3)C2=O)c1]

The target compound was obtained by cyclization performed by the same manner as described in Example 19 except that the compound of Preparative Example 22 was used instead of the compound of Preparative Example 1 as the starting material in Example 19.

$^1$H NMR (600 MHz, CDCl$_3$) δ 7.34 (s, 3H), 7.05 (d, J=1.6 Hz, 2H), 6.98-6.86 (m, 4H), 6.75 (d, J=10.3 Hz, 1H), 6.06 (d, J=9.9 Hz, 2H), 4.19 (d, J=12.2 Hz, 1H), 4.10-4.05 (m, 1H), 3.25 (d, J=11.4 Hz, 1H), 3.07-2.98 (m, 2H), 2.34 (s, 6H); $^{13}$C NMR (150 MHz, CDCl$_3$) δ 183.94, 169.63, 143.89, 143.77, 138.25, 137.94, 136.52, 129.92 (2C), 129.74, 129.70, 129.09 (2C), 129.00, 128.47 (2C), 127.19 (2C), 83.20, 63.12, 43.45, 34.79, 21.29 (2C) ppm.

Example 16: Preparation of 3-(2-nitro-4-trifluoromethyl-benzyl)-5-phenyl-1-oxa-5-azaspiro[5,5]undeca-7,10-diene-4,9-dione

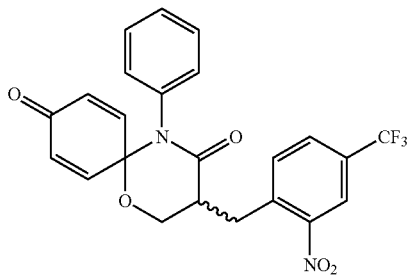 [SMILES: O=C1C=CC2(C=C1)OCC(Cc1ccc(C(F)(F)F)cc1[N+](=O)[O-])C(=O)N2c1ccccc1]

The target compound was obtained by cyclization performed by the same manner as described in Example 19 except that the compound of Preparative Example 23 was used instead of the compound of Preparative Example 1 as the starting material in Example 19.

$^1$H NMR (600 MHz, CDCl$_3$) δ 8.30 (d, J=0.9 Hz, 1H), 7.82 (dd, J=8.1, 1.5 Hz, 1H), 7.77 (d, J=8.1 Hz, 1H), 7.37-7.31 (m, 3H), 7.09 (dd, J=10.3, 3.2 Hz, 1H), 7.06-70.2 (m, 2H), 6.94 (d, J=3.2 Hz, 1H), 6.15 (dd, J=10.3, 2.0 Hz, 1H), 6.09 (dd, J=10.2, 2.0 Hz, 1H), 4.43 (dd, J=12.1, 5.1 Hz, 1H), 4.21 (dd, J=12.1, 6.9 Hz, 1H), 3.74 (dd, J=13.5, 8.0 Hz, 1H), 3.26 (dd, J=13.5, 5.9 Hz, 1H), 3.23-3.13 (m, 1H); $^{13}$C NMR (150 MHz, CDCl$_3$) δ 183.78, 169.20, 149.09, 143.51, 143.22, 138.41, 136.00, 134.36, 130.79, 130.57, 130.07, 130.05, 129.90, 129.61, 129.58, 129.20, 129.17, 122.46, 122.44, 83.53, 64.10, 43.41, 32.16 ppm.

Example 17: Preparation of 3-(2-fluoro-6-trifluoromethyl-benzyl)-5-phenyl-1-oxa-5-azaspiro[5,5]undeca-7,10-diene-4,9-dione

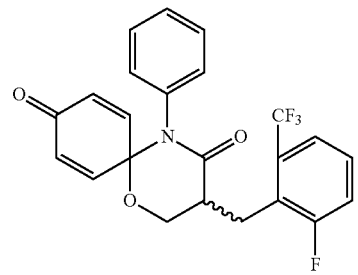 [SMILES: O=C1C=CC2(C=C1)OCC(Cc1c(F)cccc1C(F)(F)F)C(=O)N2c1ccccc1]

The target compound was obtained by cyclization performed by the same manner as described in Example 19 except that the compound of Preparative Example 24 was used instead of the compound of Preparative Example 1 as the starting material in Example 19.

$^1$H NMR (600 MHz, CDCl$_3$) δ 7.48 (d, J=7.8 Hz, 1H), 7.35 (m, 1H), 7.31-7.26 (m, 4H), 7.11-7.03 (m, 3H), 6.95 (dd, J=10.2, 3.2 Hz, 1H), 6.10 (dd, J=10.2, 2.0 Hz, 1H), 6.06 (dd, J=10.2, 2.0 Hz, 1H), 4.15 (m, 2H), 3.74 (m, 1H), 3.22-3.15 (m, 1H), 3.07 (m, 1H); $^{13}$C NMR (150 MHz, CDCl$_3$) δ 183.96, 168.85, 161.22, 143.79, 136.30, 130.09 (2C), 129.88 (2C), 129.04 (3C), 129.00, 128.65, 128.59, 124.70, 122.19, 119.23, 119.07, 83.44, 63.97, 42.36, 25.26 ppm.

Example 18: Preparation of 3-(2-chloro-5-trifluoromethyl-benzyl)-5-phenyl-1-oxa-5-azaspiro[5,5]undeca-7,10-diene-4,9-dione

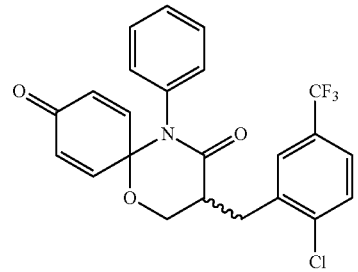 [SMILES: O=C1C=CC2(C=C1)OCC(Cc1cc(C(F)(F)F)ccc1Cl)C(=O)N2c1ccccc1]

The target compound was obtained by cyclization performed by the same manner as described in Example 19 except that the compound of Preparative Example 25 was used instead of the compound of Preparative Example 1 as the starting material in Example 19.

$^1$H NMR (600 MHz, CDCl$_3$) δ 7.65 (d, J=1.7 Hz, 1H), 7.56 (d, J=8.4 Hz, 1H), 7.53-7.49 (m, 1H), 7.37-7.31 (m, 3H), 7.08-7.05 (m, 2H), 6.94 (dd, J=10.3, 3.2 Hz, 1H), 6.89 (dd, J=10.4, 3.2 Hz, 1H), 6.12-6.07 (m, 2H), 4.23 (dd, J=12.2, 5.0 Hz, 1H), 4.13 (dd, J=12.2, 6.9 Hz, 1H), 3.62 (dd, J=12.7, 3.7 Hz, 1H), 3.24-3.15 (m, 2H); $^{13}$C NMR (150 MHz, CDCl$_3$) δ 183.95, 169.35, 143.91, 143.30, 138.37, 137.55, 136.36, 130.53, 130.09, 130.09, 130.06 (2C), 129.29 (2C), 129.14, 128.39, 125.34, 124.87, 120.38, 83.56, 63.37, 42.67, 32.21 ppm.

Example 19: Preparation of 3-benzyl-5-(pyridine-3-yl)-1-oxa-5-azaspiro[5,5]undeca-7,10-diene-4,9-dione

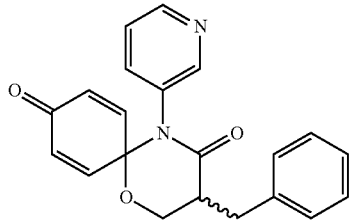 [SMILES: O=C1C=CC2(C=C1)OCC(Cc1ccccc1)C(=O)N2c1cccnc1]

The compound prepared in Preparative Example 1 (0.010 g, 0.028 mmol) was dissolved in anhydrous hexafluoroisopropanol (1 mL), to which potassium carbonate (0.008 g, 0.057 mmol) was slowly added under a stream of argon at 0° C. The mixture was stirred at the same temperature as the above for 30 minutes, to which PIFA (phenyliodinebis(trifluoroacetate)) (0.012 g, 0.043 mmol) dissolved in anhydrous hexafluoroisopropanol was slowly added at the same temperature. After stirring the mixture at the same temperature for 1 hour, the temperature was raised slowly to room temperature with stirring. After confirming by TLC that the substrate (the compound prepared in Preparative Example 1) was completely consumed, the mixture was quenched with water and diluted with ethyl acetate, followed by stirring until the water layer and the organic layer became clear. The organic layer was separated and washed with saturated brine. The organic phase was dried over sodium sulfate, followed by concentration in vacuo. The crude product was purified by silica gel column chromatography (flash column chromatography) using EtOAc:Hex (3:7) as a moving phase to give the target compound (0.018 g, 76%).

$^1$H NMR (600 Hz, CDCl$_3$): δ 8.61-8.55 (m, 1H), 8.46-8.42 (bs, ½ H), 7.5 (d, J=7.9 Hz, ½ H), 7.35-7.22 (m, 3H), 7.17-7.14 (m, ½ H), 7.11-7.01 (m, ½ H), 7.01-6.97 (m, 2H), 6.87-6.83 (m, ½ H), 6.77-6.69 (m, 1H), 6.66-6.62 (m, ½ H), 6.39-6.33 (m, 2H), 6.11-6.07 (m, ½ H), 4.11-4.06 (m, 1H), 3.84-3.75 (m, 1H), 3.66-3.89 (m, 1H), 2.84-2.78 (m, 1H), 2.60-2.55 (m, 1H); $^{13}$C NMR (125 MHz, CDCl$_3$): 183.91, 175.06, 151.89, 150.20, 141.85, 140.69, 138.83, 138.31, 130.94, 130.59, 129.52 (2C), 129.28, 128.73 (2C), 128.42, 127.03, 86.04, 64.40, 49.05, 35.84 ppm.

HRMS (ESI): calcd. For C$_{21}$H$_{19}$N$_2$O$_3$ [M+H]$^+$ 347.1396; found 347.1380.

Example 20: Preparation of 3-methyl-5-(pyridine-3-yl)-1-oxa-5-azaspiro[5,5]undeca-7,10-diene-4,9-dione

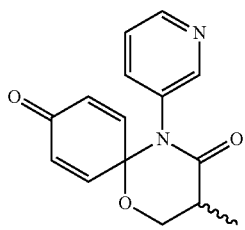

The target compound was obtained by cyclization performed by the same manner as described in Example 19 except that the compound of Preparative Example 2 was used instead of the compound of Preparative Example 1 as the starting material in Example 19.

$^1$H NMR (600 Hz, CDCl$_3$): δ 8.55-8.52 (m, 1H), 8.45-8.31 (m, 1H), 7.46-7.32 (m, 1H), 7.29-7.27 (m, 1H), 7.15-7.02 (m, 2H), 6.92-6.79 (m, 2H), 4.33-4.25 (m, 1H), 4.09-4.031 (m, 1H), 2.96-2.85 (m, 1H), 1.38 (d, J=1.68 Hz, 3H); 183.45, 171.37, 150.98, 149.76, 143.67, 142.50 (2C), 137.73, 130.27, 130.20, 123.87, 83.78, 65.91, 37.27, 13.39 ppm.

HRMS (ESI): calcd. For C$_{15}$H$_{15}$N$_2$O$_3$ [M+H]$^+$ 271.1083; found 271.1079.

Example 21: Preparation of 3-hydroxy-2-methyl-N-(4-oxocyclohexa-2,5-diethyl)-N-(pyridine-3-yl)propanamide

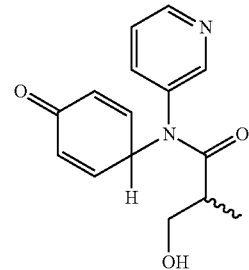 [SMILES: CC(CO)C(=O)N(c1cccnc1)C1C=CC(=O)C=C1]

The compound of Example 21 was obtained by the same manner as described in Example 20 as a by-product.

$^1$H NMR (600 Hz, CDCl$_3$): δ 8.63 (q, J=7.5, 3.9 Hz, 1H), 8.49 (d, J=7.4 Hz, 1H), 7.59 (d, J=7.2 Hz, 1H), 7.42-7.36 (m, 1H), 6.85-6.74 (m, 2H), 6.33 (d, J=8.2 Hz, 2H), 4.25-4.18 (m, 1H), 3.59-3.67 (m, 1H), 3.48-3.36 (m, 1H), 2.28-2.36 (m, 1H), 0.88 (d, J=1.68 Hz, 3H); $^{13}$C NMR (150 Hz, CDCl$_3$): 183.92, 176.66, 152.06, 151.14, 150.51, 141.94, 140.57, 131.59, 130.10, 124.198, 123.86, 69.91, 65.10, 41.12, 13.86 ppm.

Example 22: Preparation of 3-methyl-8-fluoro-5-phenyl-1-oxa-5-azaspiro[5,5]undeca-7,10-diene-4,9-dione

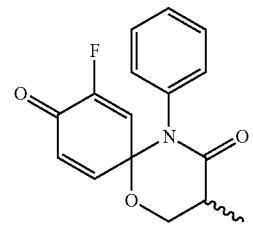 [SMILES: CC1COC2(C=CC(=O)C(F)=C2)N(c2ccccc2)C1=O]

The target compound was obtained by cyclization performed by the same manner as described in Example 19 except that the compound of Preparative Example 27 was used instead of the compound of Preparative Example 1 as the starting material in Example 19.

$^1$H NMR (600 MHz, CDCl$_3$) δ 7.52-7.37 (m, 4H), 7.11-7.04 (m, 2H), 6.64 (dd, J=11.9, 2.9 Hz, 1H), 6.12-6.06 (m,

1H), 4.25-4.18 (m, 1H), 4.13 (dd, J=14.8, 7.8 Hz, 1H), 3.07-2.96 (m, 1H), 1.38 (d, J=7.3 Hz, 3H); $^{13}$C NMR (150 MHz, CDCl$_3$) δ 175.63, 168.68, 155.16, 145.24, 142.82, 129.91, 129.26, 129.02, 128.95, 128.28 (2C), 118.94, 82.95, 64.95, 43.35, 13.94 ppm.

Example 23: Preparation of 3-allyl-8-fluoro-5-phenyl-1-oxa-5-azaspiro[5,5]undeca-7,10-diene-4,9-dione

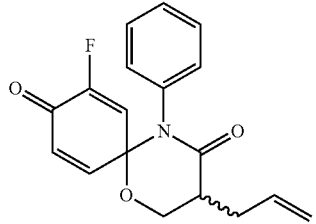

The target compound was obtained by cyclization performed by the same manner as described in Example 19 except that the compound of Preparative Example 28 was used instead of the compound of Preparative Example 1 as the starting material in Example 19.

$^1$H NMR (600 MHz, CDCl$_3$) δ 7.38-7.27 (m, 4H), 7.04-7.01 (m, 2H), 6.98 (dd, J=10.1, 3.4 Hz, 1H), 6.94 (dd, J=10.2, 3.1 Hz, 1H), 5.94-5.78 (m, 1H), 5.22-5.11 (m, 2H), 3.78-3.76 (m, 1H), 3.54 (dd, J=10.2, 5.5 Hz, 1H), 3.04-2.89 (m, 1H), 2.37-2.27 (m, 1H), 2.18-2.15 (m, 1H); $^{13}$C NMR (150 MHz, CDCl$_3$) δ 176.93, 168.69, 155.36, 144.59, 135.86, 135.34, 131.12, 130.59, 129.92, 129.89, 129.36, 128.04 (2C), 116.57, 116.56, 64.53, 46.49, 35.14 ppm.

Example 24: Preparation of 3-benzyl-8-fluoro-5-phenyl-1-oxa-5-azaspiro[5,5]undeca-7,10-diene-4,9-dione

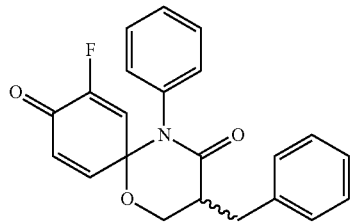 [SMILES: O=C1C=CC2(C=C1F)OCC(Cc1ccccc1)C(=O)N2c1ccccc1]

The target compound was obtained by cyclization performed by the same manner as described in Example 19 except that the compound of Preparative Example 13 was used instead of the compound of Preparative Example 1 as the starting material in Example 19.

$^1$H NMR (600 MHz, CDCl$_3$) δ 7.44-7.36 (m, 6H), 7.10-7.06 (m, 3H), 6.67 (d, J=9.4 Hz, 1H), 6.53 (d, J=12.0 Hz, 1H), 6.14-6.03 (m, 2H), 4.16 (dd, J=12.0, 5.4 Hz, 1H), 4.08 (dd, J=12.1, 5.8 Hz, 1H), 3.36-3.32 (m, 1H), 3.18-3.07 (m, 2H); $^{13}$C NMR (151 MHz, CDCl$_3$) δ 176.78, 168.72, 155.38, 143.74, 143.62, 138.08, 136.32, 127.89, 129.70, 129.48, 129.16, 129.04, 128.94, 128.80, 128.64, 126.84, 120.16, 118.72, 82.38, 63.08, 43.42, 34.96 ppm.

Example 25: Preparation of 3,8-dimethyl-5-phenyl-1-oxa-5-azaspiro[5,5]undeca-7,10-diene-4,9-dione

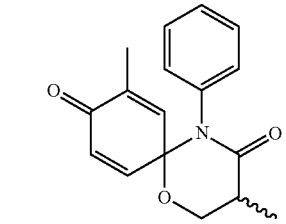 [SMILES: CC1=CC2(C=CC1=O)OCC(C)C(=O)N2c1ccccc1]

The target compound was obtained by cyclization performed by the same manner as described in Example 19 except that the compound of Preparative Example 12 was used instead of the compound of Preparative Example 1 as the starting material in Example 19.

$^1$H NMR (600 Hz, CDCl$_3$): δ 7.33-7.26 (m, 3H), 7.05-7.00 (m, 2.5H), 6.91-6.86 (m, ½ H), 6.82-6.79 (s, ½H), 6.71-6.66 (s, ½H), 6.10-6.01 (m, 1H), 4.32-4.25 (m, 1H), 4.06-3.99 (m, 1H), 2.93-2.84 (m, 1H), 1.82-1.74 (dd, J=0.8, 4 Hz, 3H), 1.40-1.33 (m, 3H); $^{13}$C NMR (150 Hz, CDCl$_3$): δ 184.99, 172.47, 144.29, 143.29, 140.25, 139.22, 137.03, 137.00, 130.23, 129.98, 129.19, 129.07, 84.40, 66.20, 37.43, 15.57, 13.85 ppm.

Example 26: Preparation of 3-allyl-8-methyl-5-phenyl-1-oxa-5-azaspiro[5,5]undeca-7,10-diene-4,9-dione

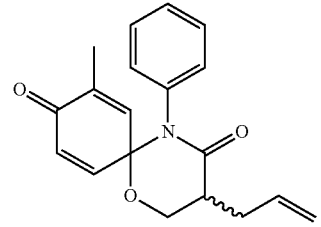 [SMILES: C=CCC1COC2(C=CC(=O)C(C)=C2)N(c2ccccc2)C1=O]

The target compound was obtained by cyclization performed by the same manner as described in Example 19 except that the compound of Preparative Example 11 was used instead of the compound of Preparative Example 1 as the starting material in Example 19.

$^1$H NMR (600 MHz, CDCl$_3$): δ 7.34-7.28 (m, 3H), 7.05-7.01 (m, 2H), 6.99 (dd, J=10.1, 3.2 Hz, 1H), 6.71 (dd, J=3.1, 1.5 Hz, 1H), 6.07 (t, J=6.7 Hz, 1H), 5.87-5.82 (m, 1H), 5.23-5.15 (m, 2H), 4.28 (dd, J=12.1, 5.5 Hz, 1H), 4.15-4.09 (m, 1H), 2.85 (dtt, J=12.5, 11.1, 5.6 Hz, 1H), 2.75-2.69 (m, 1H), 2.52 (dt, J=14.2, 8.6 Hz, 1H), 1.77 (d, J=1.5 Hz, 3H); $^{13}$C NMR (150 Hz, CDCl$_3$): δ 184.88, 170.09, 143.39, 139.75, 137.00, 136.87, 134.88, 130.08 (2C), 129.98, 129.14 (2C), 129.03, 118.40, 84.115, 63.56, 41.52, 33.38, 15.53 ppm.

Example 27: Preparation of 3-(2-methyl-allyl)-8-methyl-5-phenyl-1-oxa-5-azaspiro[5,5]undeca-7,10-diene-4,9-dione

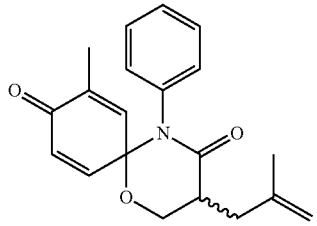 [SMILES: C=C(C)CC1COC2(C=CC(=O)C(C)=C2)N(c2ccccc2)C1=O]

The target compound was obtained by cyclization performed by the same manner as described in Example 19 except that the compound of Preparative Example 29 was used instead of the compound of Preparative Example 1 as the starting material in Example 19.

$^1$H NMR (600 MHz, CDCl$_3$): δ 7.34-7.28 (m, 3H), 7.05-7.01 (m, 2H), 6.99 (dd, J=10.1, 3.2 Hz, 1H), 6.71 (dd, J=3.1, 1.5 Hz, 1H), 6.07 (t, J=6.7 Hz, 1H), 5.87-5.82 (m, 1H), 5.23-5.15 (m, 2H), 4.28 (dd, J=12.1, 5.5 Hz, 1H), 4.15-4.09 (m, 1H), 2.85 (dtt, J=12.5, 11.1, 5.6 Hz, 1H), 2.75-2.69 (m, 1H), 2.52 (dt, J=14.2, 8.6 Hz, 1H), 1.77 (d, J=1.5 Hz, 3H); $^{13}$C NMR (150 Hz, CDCl$_3$): δ 184.88, 170.09, 143.39, 139.75, 137.00, 136.87, 134.88, 130.08 (2C), 129.98, 129.14 (2C), 129.03, 118.40, 84.115, 63.56, 41.52, 33.38, 15.53 ppm.

Example 28: Preparation of 3-benzyl-8-methyl-5-phenyl-1-oxa-5-azaspiro[5,5]undeca-7,10-diene-4,9-dione

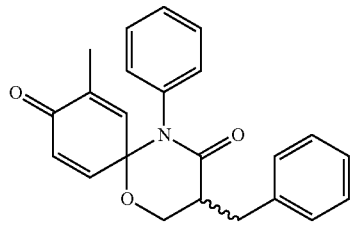 [SMILES: CC1=CC2(C=CC1=O)OCC(Cc1ccccc1)C(=O)N2c1ccccc1]

The target compound was obtained by cyclization performed by the same manner as described in Example 19 except that the compound of Preparative Example 10 was used instead of the compound of Preparative Example 1 as the starting material in Example 19.

$^1$H NMR (600 Hz, CDCl$_3$): δ 7.39-7.26 (m, 9H), 7.04-6.96 (s, 1H), 6.69-6.62 (d, J=3 Hz, 2H), 6.3-5.97 (d, J=2.5 Hz, 1H), 4.20-4.10 (m 1H), 4.08-4.02 (m 1H), 3.31-3.25 (d, J=2.8 Hz 1H), 3.13-3.00 (m, 2H), 1.61-1.53 (s, 3H); $^{13}$C NMR (150 Hz, CDCl$_3$): δ 184.86, 170.05, 143.38, 139.53, 138.35, 136.97, 136.87, 130.08 (2C), 129.98, 129.64 (2C), 129.15 (2C), 129.07, 128.90 (2C), 127.07, 84.09, 63.21, 43.56, 35.13, 15.50 ppm.

Example 29: Preparation of 3,5-dimethyl-1-oxa-5-azaspiro[5,5]undeca-7,10-diene-4,9-dione

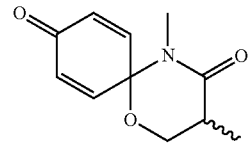

The target compound was obtained by cyclization performed by the same manner as described in Example 19 except that the compound of Preparative Example 30 was used instead of the compound of Preparative Example 1 as the starting material in Example 19.

$^1$H NMR (600 MHz, CDCl$_3$) δ 6.88-6.84 (m, 1H), 6.76-6.74 (m, 1H), 6.37-6.35 (m, 2H), 4.16 (dd, J=11.8, 5.3 Hz, 1H), 3.87 (dd, J=11.7, 7.6 Hz, 1H), 2.79 (s, 3H), 2.77-2.71 (m, 1H), 1.30 (d, J=7.2 Hz, 3H); $^{13}$C NMR (150 MHz, CDCl$_3$) δ 183.98, 170.84, 144.54, 143.50, 130.58, 130.50, 82.31, 65.72, 36.89, 28.43, 13.46 ppm.

Example 30: Preparation of 3-allyl-5-methyl-1-oxa-5-azaspiro[5,5]undeca-7,10-diene-4,9-dione

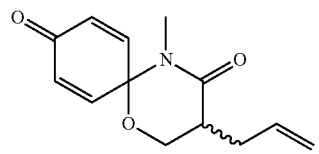 [SMILES: C=CCC1COC2(C=CC(=O)C=C2)N(C)C1=O]

The target compound was obtained by cyclization performed by the same manner as described in Example 19 except that the compound of Preparative Example 31 was used instead of the compound of Preparative Example 1 as the starting material in Example 19.

$^1$H NMR (600 MHz, CDCl$_3$) δ 6.83-6.77 (m, 2H), 6.36 (d, J=10.0, 1.8 Hz, 2H), 5.85-5.78 (m, 1H), 5.18-5.13 (m, 2H), 4.14 (dd, J=12.0, 5.0 Hz, 1H), 3.97 (dd, J=12.0, 6.5 Hz, 1H), 2.79 (s, 3H), 2.72-2.65 (m, 2H), 2.45-2.38 (m, 1H); $^{13}$C NMR (150 MHz, CDCl$_3$) δ 183.95, 169.58, 144.06, 143.79, 134.71, 130.63, 130.59, 118.05, 82.12, 63.08, 41.25, 33.04, 28.47.

Example 31: Preparation of 3-(3-butenyl)-5-methyl-1-oxa-5-azaspiro[5,5]undeca-7,10-diene-4,9-dione

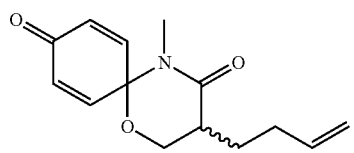 [SMILES: C=CCCC1COC2(C=CC(=O)C=C2)N(C)C1=O]

The target compound was obtained by cyclization performed by the same manner as described in Example 19 except that the compound of Preparative Example 32 was used instead of the compound of Preparative Example 1 as the starting material in Example 19.

¹H NMR (600 MHz, CDCl₃) δ 6.81-6.75 (m, 2H), 6.37-6.32 (m, 2H), 5.85-5.78 (m, 1H), 5.11-5.01 (m, 2H), 4.16 (dd, J=11.9, 4.9 Hz, 1H), 3.94 (dd, J=11.9, 6.4 Hz, 1H), 2.77 (s, 3H), 2.62-2.58 (m, 1H), 2.27-2.13 (m, 2H), 2.08-2.02 (m, 1H), 1.71-1.65 (m, 1H); ¹³C NMR (150 MHz, CDCl₃) δ 183.96, 170.22, 144.08, 143.88, 137.38, 130.58 (2C), 115.69, 82.06, 63.57, 41.19, 31.14, 28.45, 27.86 ppm.

Example 32: Preparation of 3-(2-methyl-allyl)-5-methyl-1-oxa-5-azaspiro[5,5]undeca-7,10-diene-4,9-dione

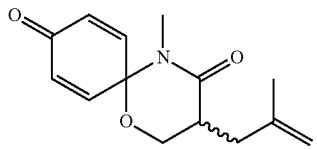 [SMILES: C=C(C)CC1COC2(C=CC(=O)C=C2)N(C)C1=O]

The target compound was obtained by cyclization performed by the same manner as described in Example 19 except that the compound of Preparative Example 33 was used instead of the compound of Preparative Example 1 as the starting material in Example 19.

¹H NMR (600 MHz, CDCl₃) δ 6.81-6.77 (m, 2H), 6.37-6.33 (m, 2H), 4.86 (s, 1H), 4.77 (s, 1H), 4.09 (dd, J=11.9, 4.8 Hz, 1H), 3.92-3.88 (m, 1H), 2.78 (s, 3H), 2.75-2.69 (m, 2H), 2.32-2.26 (m, 1H), 1.77 (s, 3H); ¹³C NMR (150 MHz, CDCl₃) δ 183.96, 170.05, 143.96, 143.92, 141.86, 130.61 (2C), 113.45, 82.11, 62.95, 39.63, 36.99, 21.84 ppm.

Example 33: Preparation of 3-benzyl-5-methyl-1-oxa-5-azaspiro[5,5]undeca-7,10-diene-4,9-dione

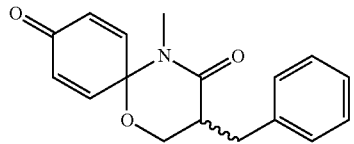 [SMILES: CN1C(=O)C(Cc2ccccc2)COC12C=CC(=O)C=C2]

The target compound was obtained by cyclization performed by the same manner as described in Example 19 except that the compound of Preparative Example 4 was used instead of the compound of Preparative Example 1 as the starting material in Example 19.

¹H NMR (600 MHz, CDCl₃) δ 7.36-7.32 (m, 2H), 7.27-7.24 (m, 3H), 6.80-6.77 (m, 1H), 6.63-6.60 (m, 1H), 6.36-6.32 (m, 2H), 4.01 (dd, J=12.0, 4.6 Hz, 1H), 3.88 (dd, J=12.0, 5.7 Hz, 1H), 3.33 (dd, J=13.3, 3.5 Hz, 1H), 2.91 (dd, J=13.3, 10.4 Hz, 1H), 2.89-2.83 (m, 1H), 2.81 (s, 3H); ¹³C NMR (150 MHz, CDCl₃) δ 183.94, 169.63, 143.94, 143.74, 138.23, 130.63, 130.61, 129.16 (2C), 128.70 (2C), 126.77, 82.12, 62.69, 43.52, 34.95, 28.54 ppm.

Example 34: Preparation of 3-(4-fluoro-benzyl)-5-methyl-1-oxa-5-azaspiro[5,5]undeca-7,10-diene-4,9-dione

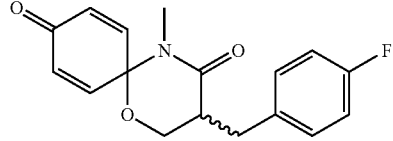 [SMILES: CN1C(=O)C(Cc2ccc(F)cc2)COC12C=CC(=O)C=C2]

The target compound was obtained by cyclization performed by the same manner as described in Example 19 except that the compound of Preparative Example 34 was used instead of the compound of Preparative Example 1 as the starting material in Example 19.

¹H NMR (600 MHz, CDCl₃) δ 7.22-7.19 (m, 2H), 7.04-7.00 (m, 2H), 6.80-6.76 (m, 1H), 6.64-6.61 (m, 1H), 6.35-6.32 (m, 2H), 4.01 (dd, J=12.0, 4.7 Hz, 1H), 3.85 (dd, J=12.0, 5.9 Hz, 1H), 3.27 (dd, J=13.8, 3.9 Hz, 1H), 2.89 (dd, J=13.8, 10.1 Hz, 1H), 2.83-2.80 (m, 1H), 2.79 (s, 3H); ¹³C NMR (150 MHz, CDCl₃) δ 183.87, 169.39, 160.93, 143.79, 143.64, 133.88, 133.86, 130.69, 130.65, 130.64, 115.59, 115.45, 82.14, 62.56, 43.54, 34.07, 28.53 ppm.

Example 35: Preparation of 3-(4-bromo-benzyl)-5-methyl-1-oxa-5-azaspiro[5,5]undeca-7,10-diene-4,9-dione

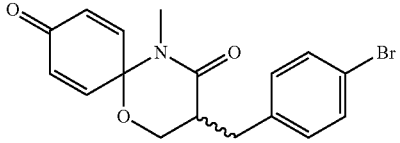

The target compound was obtained by cyclization performed by the same manner as described in Example 19 except that the compound of Preparative Example 35 was used instead of the compound of Preparative Example 1 as the starting material in Example 19.

¹H NMR (600 MHz, CDCl₃) δ 7.45 (d, J=8.3 Hz, 2H), 7.12 (d, J=8.3 Hz, 2H), 6.77 (dd, J=10.3, 3.1 Hz, 1H), 6.63 (dd, J=10.3, 3.1 Hz, 1H), 6.34 (d, J=10.4 Hz, 2H), 4.00 (dd, J=12.0, 4.6 Hz, 1H), 3.84 (dd, J=12.0, 5.8 Hz, 1H), 3.25 (dd, J=13.5, 3.7 Hz, 1H), 2.87 (dd, J=13.5, 10.2 Hz, 1H), 2.83-2.81 (m, 1H), 2.79 (s, 3H); ¹³C NMR (150 MHz, CDCl₃) δ 183.84, 169.26, 143.72, 143.62, 137.23, 131.78 (2C), 130.89 (2C), 130.72, 130.68, 120.67, 82.16, 62.54, 43.34, 34.27, 28.55 ppm.

Example 36: Preparation of 3-(4-cyano-benzyl)-5-methyl-1-oxa-5-azaspiro[5,5]undeca-7,10-diene-4,9-dione

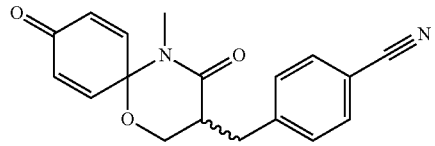 [SMILES: CN1C(=O)C(Cc2ccc(C#N)cc2)COC12C=CC(=O)C=C2]

The target compound was obtained by cyclization performed by the same manner as described in Example 19 except that the compound of Preparative Example 36 was used instead of the compound of Preparative Example 1 as the starting material in Example 19.

¹H NMR (600 MHz, CDCl₃) δ 7.64 (d, J=8.2 Hz, 2H), 7.37 (d, J=8.2 Hz, 2H), 6.79-6.76 (m, 1H), 6.66-6.61 (m, 1H), 6.37-6.34 (m, 2H), 4.03 (dd, J=12.1, 4.7 Hz, 1H), 3.83 (dd, J=12.1, 6.1 Hz, 1H), 3.36 (dd, J=13.8, 4.3 Hz, 1H), 2.97 (dd, J=13.8, 9.9 Hz, 1H), 2.89-2.85 (m, 1H), 2.80 (s, 3H); ¹³C NMR (150 MHz, CDCl₃) δ 183.74, 168.89, 144.02, 143.42 (2C), 132.49 (2C), 130.84, 130.81, 129.97 (2C), 118.67, 110.83, 82.23, 62.55, 43.16, 34.93 ppm.

Example 37: Preparation of 3-(2-(phenylsulfonylmethyl)-benzyl)-5-methyl-1-oxa-5-azaspiro[5,5]undeca-7,10-diene-4,9-dione

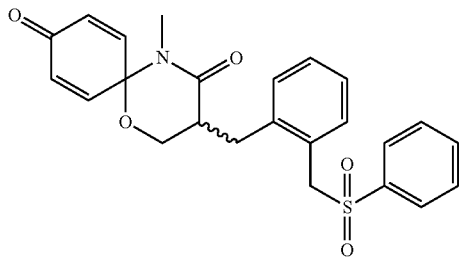 [SMILES: CN1C(=O)C(Cc2ccccc2CS(=O)(=O)c2ccccc2)COC12C=CC(=O)C=C2]

The target compound was obtained by cyclization performed by the same manner as described in Example 19 except that the compound of Preparative Example 37 was used instead of the compound of Preparative Example 1 as the starting material in Example 19.

¹H NMR (600 MHz, CDCl₃) δ 7.80-7.78 (m, 2H), 7.65 (t, J=7.5 Hz, 1H), 7.52 (t, J=7.8 Hz, 2H), 7.31 (t, J=7.5, 1.4 Hz, 1H), 7.23 (d, J=7.5 Hz, 1H), 7.21-7.15 (m, 2H), 6.79 (dd, J=10.0, 3.2 Hz, 1H), 6.73 (dd, J=10.0, 3.2 Hz, 1H), 6.37-6.33 (m, 2H), 4.53 (s, 2H), 4.01 (dd, J=12.1, 4.2 Hz, 1H), 3.82 (dd, J=12.1, 4.9 Hz, 1H), 3.25 (dd, J=14.3, 3.6 Hz, 1H), 2.84 (dd, J=14.2, 10.7 Hz, 1H), 2.79 (s, 3H), 2.78-2.77 (m, 1H); ¹³C NMR (150 MHz, CDCl₃) δ 183.88, 169.47, 144.12, 143.26, 138.99, 138.64, 133.89, 132.82, 130.81, 130.70, 130.46, 129.30, 129.13 (2C), 128.53 (2C), 127.12, 126.79, 82.21, 62.39, 59.27, 43.38, 31.54 ppm.

Example 38: Preparation of 3-(2-propynyl)-5-phenyl-1-oxa-5-azaspiro[5,5]undeca-7,10-diene-4,9-dione

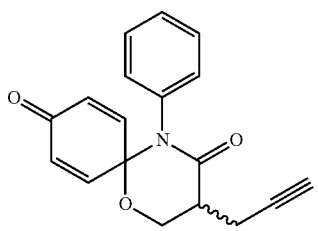 [SMILES: C#CCC1COC2(C=CC(=O)C=C2)N(c2ccccc2)C1=O]

The target compound was obtained by cyclization performed by the same manner as described in Example 19 except that the compound of Preparative Example 38 was used instead of the compound of Preparative Example 1 as the starting material in Example 19.

¹H-NMR (600 MHz, CDCl₃) δ 7.30-7.33 (m, 3H), 7.02-7.05 (m, 2H), 7.00 (dd, J=2.1, 10.2 Hz 1H), 6.96 (dd, J=2.6, 10.8 Hz 1H), 6.09 (dd, J=3.2, 10.1 Hz 1H), 6.06 (dd, J=2.7, 10.6 Hz 1H), 5.82-5.89 (m, 1H), 5.16-5.21 (m, 2H), 4.27-4.30 (m, 1H), 4.12-4.15 (m, 1H), 2.87-2.83 (m, 1H), 2.70-2.74 (m, 1H), 2.50-2.55 (m, 1H) ppm.

Example 39: Preparation of 3-((1-(4-methoxyphenyl)-1H-1,2,3-triazol-4-yl)methyl)-5-phenyl-1-oxa-5-azaspiro[5,5]undeca-7,10-diene-4,9-dione

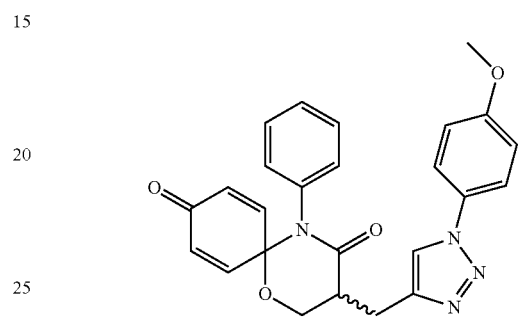

The target compound was obtained according to reaction formula B below by using the compound of Example 38 as a starting material.

Reaction Formula B

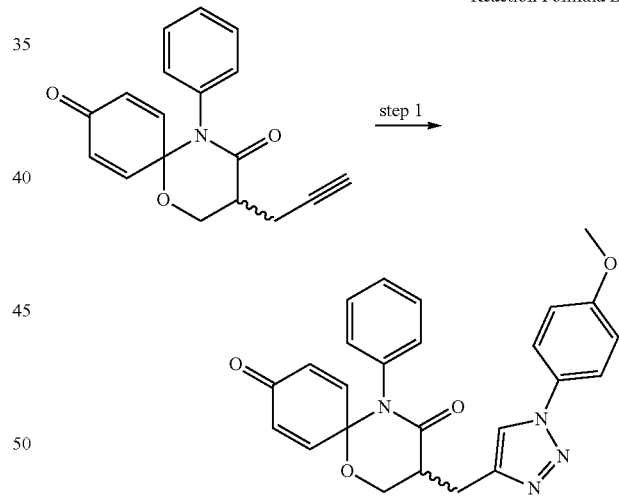

Step 1: Preparation of 3-((1-(4-methoxyphenyl)-1H-1,2,3-triazol-4-yl)methyl)-5-phenyl-1-oxa-5-azaspiro[5,5]undeca-7,10-diene-4,9-dione The compound of Example 38 (1 mmol) was dissolved in the mixed solvent comprising tetrahydrofuran and distilled water at the ratio of 1:1 at 5° C., to which 1-azido-4-methoxybenzene (1.5 mmol) and copper sulfate pentahydrate (CuSO4.5H₂O) (2 mmol) were added. Thereafter, sodium ascorbate (1 mmol) was added thereto and the temperature was raised slowly to room temperature with stirring. After confirming by TLC that the starting material was completely consumed, the mixture was extracted with ethyl acetate. The organic layer was washed with brine, and dried over sodium sulfate. The solvent was removed under reduced pressure. The crude product was purified by silica gel column chromatography (flash column chromatography) to give the target compound.

$^1$H NMR (600 MHz, CDCl$_3$) δ 7.80 (s, 1H), 7.64 (d, J=9.0 Hz, 2H), 7.32-7.28 (m, 3H), 7.19 (dd, J=10.3, 3.2 Hz, 1H), 7.04 (d, J=9.0 Hz, 2H), 6.98 (dd, J=7.7, 1.5 Hz, 2H), 6.84 (dd, J=10.2, 3.2 Hz, 1H), 6.12 (dd, J=10.3, 2.0 Hz, 1H), 6.03 (dd, J=10.2, 2.0 Hz, 1H), 4.67 (dd, J=12.2, 9.7 Hz, 1H), 4.40 (dd, J=12.2, 6.6 Hz, 1H), 3.90 (s, 3H), 3.44 (dd, J=15.0, 6.9 Hz, 1H), 3.40-3.31 (m, 1H), 3.18 (dd, J=15.0, 3.7 Hz, 1H); $^{13}$C NMR (150 MHz, CDCl$_3$) δ 184.02, 169.59, 159.83, 144.78, 142.96, 136.47, 130.44, 129.83, 129.80 (3C), 129.07 (2C), 128.97 (2C), 122.02 (2C), 121.11, 114.80 (2C), 83.43, 63.74, 55.65, 41.54, 31.94 ppm.

Example 40: Preparation of 3-((1-benzyl-1H-1,2,3-triazol-4-yl)methyl)-5-phenyl-1-oxa-5-azaspiro[5,5]undeca-7,10-diene-4,9-dione

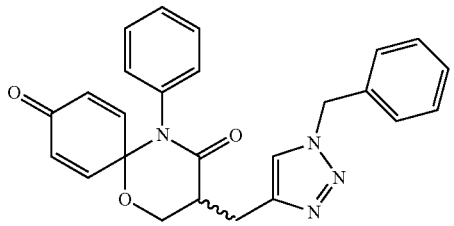 [SMILES: O=C1C=CC2(C=C1)OCC(Cc1cn(Cc3ccccc3)nn1)C(=O)N2c1ccccc1]

The target compound was obtained by the same manner as described in Example 39 except that 1-azido-4-benzylbenzene was used instead of 1-azido-4-methoxybenzene in step 1 of reaction formula B.

$^1$H NMR (600 MHz, CDCl$_3$) δ 7.44-7.36 (m, 4H), 7.35-7.30 (m, 3H), 7.25 (t, J=7.4 Hz, 2H), 6.92 (dd, J=10.3, 3.2 Hz, 1H), 6.83 (d, J=7.3 Hz, 2H), 6.78 (dd, J=10.2, 3.2 Hz, 1H), 6.06 (dd, J=10.3, 2.0 Hz, 1H), 5.99 (dd, J=10.2, 2.0 Hz, 1H), 5.59 (d, J=14.8 Hz, 1H), 5.46 (d, J=14.8 Hz, 1H), 4.49 (dd, J=12.1, 9.8 Hz, 1H), 4.33 (dd, J=12.2, 6.7 Hz, 1H), 3.38 (dd, J=15.0, 6.5 Hz, 1H), 3.30-3.21 (m, 1H), 3.06 (dd, J=15.0, 3.7 Hz, 1H); $^{13}$C NMR (150 MHz, CDCl$_3$) δ 183.99, 177.33, 169.45, 144.71, 142.85, 136.39, 134.79, 130.50, 129.73, 129.67 (3C), 129.18 (2C), 129.04 (2C), 128.90, 128.86, 128.06 (2C), 83.27, 63.60, 54.20, 41.29, 23.61 ppm.

Example 41: Preparation of 3-methyl-5-isopropyl-1-oxa-5-azaspiro[5,5]undeca-7,10-diene-4,9-dione

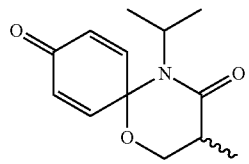

The target compound was obtained by cyclization performed by the same manner as described in Example 19 except that the compound of Preparative Example 39 was used instead of the compound of Preparative Example 1 as the starting material in Example 19.

$^1$H NMR (600 MHz, CDCl$_3$) δ 6.92-6.89 (m, 1H), 6.82-6.79 (m, 1H), 6.36-6.34 (m, 2H), 4.09 (dd, J=11.7, 5.3 Hz, 1H), 3.80 (dd, J=11.7, 7.6 Hz, 1H), 3.09-3.05 (m, 1H), 2.69-2.063 (m, 1H), 1.41 (d, J=6.8 Hz, 3H), 1.39 (d, 3H), 1.26 (s, 3H); $^{13}$C NMR (150 MHz, CDCl$_3$) δ 184.21, 170.45, 144.99, 144.01, 130.32, 130.22, 82.89, 65.41, 49.63, 37.77, 20.53, 20.45, 13.36 ppm.

Example 42: Preparation of 3-allyl-5-isopropyl-1-oxa-5-azaspiro[5,5]undeca-7,10-diene-4,9-dione

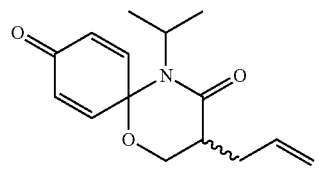 [SMILES: C=CCC1COC2(C=CC(=O)C=C2)N(C(C)C)C1=O]

The target compound was obtained by cyclization performed by the same manner as described in Example 19 except that the compound of Preparative Example 40 was used instead of the compound of Preparative Example 1 as the starting material in Example 19.

$^1$H NMR (600 MHz, CDCl$_3$) δ 6.88-6.80 (m, 2H), 6.36-6.34 (m, 2H), 5.84-5.76 (m, 1H), 5.16-5.11 (m, 2H), 4.06 (dd, J=11.9, 5.1 Hz, 1H), 3.90 (dd, J=11.9, 6.7 Hz, 1H), 3.09-3.05k (m, 1H), 2.65-2.59 (m, 2H), 2.46-2.41 (m, 1H), 1.42 (d, J=6.8 Hz, 3H), 1.38 (d, J=6.8 Hz, 3H); $^{13}$C NMR (150 MHz, CDCl$_3$) δ 184.18, 169.11, 144.63, 144.21, 134.78, 130.34 (2C), 117.92, 82.68, 62.80, 49.75, 42.01, 33.00, 20.48, 20.46 ppm.

Example 43: Preparation of 3-(4-fluoro-benzyl)-5-isopropyl-1-oxa-5-azaspiro[5,5]undeca-7,10-diene-4,9-dione

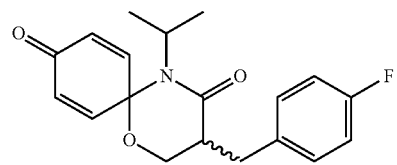 [SMILES: CC(C)N1C(=O)C(Cc2ccc(F)cc2)COC12C=CC(=O)C=C2]

The target compound was obtained by cyclization performed by the same manner as described in Example 19 except that the compound of Preparative Example 41 was used instead of the compound of Preparative Example 1 as the starting material in Example 19.

$^1$H NMR (600 MHz, CDCl$_3$) δ 7.21 (dd, J=8.4, 5.4 Hz, 2H), 7.02 (t, J=8.6 Hz, 2H), 6.82 (dd, J=10.0, 3.1 Hz, 1H), 6.59 (dd, J=10.0, 3.1 Hz, 1H), 6.35-6.30 (m, 2H), 3.97 (dd, J=12.0, 4.9 Hz, 1H), 3.80 (dd, J=12.0, 6.2 Hz, 1H), 3.19 (dd, J=13.9, 4.1 Hz, 1H), 3.08-3.04 (m, 1H), 2.97 (dd, J=13.9, 9.4 Hz, 1H), 2.78-2.75 (m, 1H), 1.43 (d, J=6.8 Hz, 3H), 1.39 (d, J=6.8 Hz, 3H); $^{13}$C NMR (150 MHz, CDCl$_3$) δ 184.08, 168.87, 162.54, 144.14 (2C), 133.97, 130.79, 130.74, 130.45, 130.40, 115.49, 115.35, 82.68, 62.37, 49.80, 44.23, 34.05, 20.46 (2C) ppm.

Example 44: Preparation of 3-(4-trifluoromethyl-benzyl)-5-isopropyl-1-oxa-5-azaspiro[5,5]undeca-7,10-diene-4,9-dione

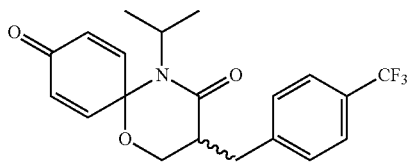 [SMILES: CC(C)N1C(=O)C(Cc2ccc(C(F)(F)F)cc2)COC12C=CC(=O)C=C2]

The target compound was obtained by cyclization performed by the same manner as described in Example 19 except that the compound of Preparative Example 42 was used instead of the compound of Preparative Example 1 as the starting material in Example 19.

$^1$H NMR (600 MHz, CDCl$_3$) δ 7.59 (d, J=8.1 Hz, 2H), 7.37 (d, J=8.0 Hz, 2H), 6.82 (dd, J=10.0, 3.1 Hz, 1H), 6.59 (dd, J=10.0, 3.1 Hz, 1H), 6.35-6.31 (m, 2H), 3.97 (dd, J=12.0, 4.8 Hz, 1H), 3.79 (dd, J=12.0, 6.1 Hz, 1H), 3.32-3.28 (m, 1H), 3.08-3.01 (m, 2H), 2.83-2.79 (m, 1H), 1.43 (d, J=6.8 Hz, 3H), 1.40 (d, J=6.8 Hz, 3H); $^{13}$C NMR (150 MHz, CDCl$_3$) δ 184.00, 168.58, 143.98 (2C), 142.62, 130.51, 130.47, 129.62 (2C), 129.23, 129.02, 125.55, 125.52, 82.72, 62.32, 49.85, 44.06, 34.67, 20.45, 20.42 ppm.

Example 45: Preparation of 3-(4-cyano-benzyl)-5-isopropyl-1-oxa-5-azaspiro[5,5]undeca-7,10-diene-4,9-dione

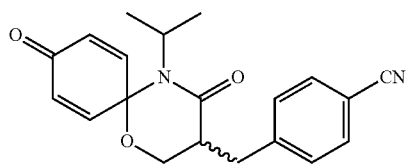 [SMILES: CC(C)N1C(=O)C(Cc2ccc(C#N)cc2)COC12C=CC(=O)C=C2]

The target compound was obtained by cyclization performed by the same manner as described in Example 19 except that the compound of Preparative Example 43 was used instead of the compound of Preparative Example 1 as the starting material in Example 19.

$^1$H NMR (600 MHz, CDCl$_3$) δ 7.62 (d, J=8.2 Hz, 2H), 7.36 (d, J=8.2 Hz, 2H), 6.83-6.80 (m, 1H), 6.60-6.57 (m, 1H), 6.35-6.31 (m, 2H), 3.98 (dd, J=12.0, 4.9 Hz, 1H), 3.76 (dd, J=12.0, 6.2 Hz, 1H), 3.27 (dd, J=13.8, 4.4 Hz, 1H), 3.09-3.00 (m, 2H), 2.83-2.79 (m, 1H), 1.42 (d, J=6.8 Hz, 3H), 1.38 (d, J=6.8 Hz, 3H); $^{13}$C NMR (150 MHz, CDCl$_3$) δ 183.94, 168.30, 144.17, 143.88, 143.79, 132.38 (2C), 130.60, 130.53, 130.10 (2C), 118.72, 110.74, 82.74, 62.32, 49.88, 43.89, 34.97, 20.45, 20.39 ppm.

Example 46: Preparation of 3-(2-fluoro-6-trifluoromethyl-benzyl)-5-isopropyl-1-oxa-5-azaspiro[5,5]undeca-7,10-diene-4,9-dione

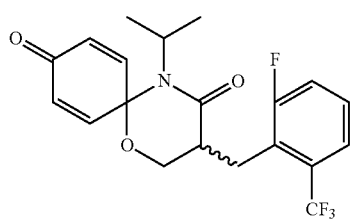 [SMILES: CC(C)N1C(=O)C(Cc2c(F)cccc2C(F)(F)F)COC12C=CC(=O)C=C2]

The target compound was obtained by cyclization performed by the same manner as described in Example 19 except that the compound of Preparative Example 44 was used instead of the compound of Preparative Example 1 as the starting material in Example 19.

$^1$H NMR (600 MHz, CDCl$_3$) δ 7.50 (d, J=7.9 Hz, 1H), 7.38 (dd, J=13.5, 8.0 Hz, 1H), 7.27 (d, J=8.9 Hz, 1H), 6.92 (dd, J=10.1, 3.1 Hz, 1H), 6.85 (dd, J=10.1, 3.1 Hz, 1H), 6.39-6.34 (m, 2H), 3.98 (dd, J=11.8, 4.2 Hz, 1H), 3.90 (dd, J=11.8, 5.4 Hz, 1H), 3.64 (dd, J=13.5, 6.0 Hz, 1H), 3.10-3.06 (m, 1H), 2.99-2.92 (m, 2H), 1.39 (dd, J=6.8, 2.9 Hz, 6H); $^{13}$C NMR (150 MHz, CDCl$_3$) δ 184.20, 168.02, 161.17, 144.51, 144.13, 130.43 (2C), 128.51, 128.45, 125.11, 122.13, 119.09, 118.94, 82.77, 63.34, 49.78, 43.01, 25.24, 20.36, 20.21 ppm.

Example 47: Preparation of 3-((1-phenyl-1H-1,2,3-triazol-4-yl)methyl)-5-phenyl-1-oxa-5-azaspiro[5,5]undeca-7,10-diene-4,9-dione

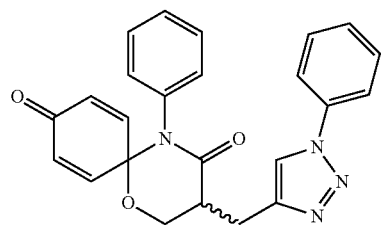 [SMILES: O=C1C=CC2(C=C1)OCC(Cc1cn(-c3ccccc3)nn1)C(=O)N2c1ccccc1]

The target compound was obtained by the same manner as described in Example 39 except that 4-azido-1,1'biphenyl was used instead of 1-azido-4-methoxybenzene in step 1 of reaction formula B.

$^1$H NMR (600 MHz, CDCl$_3$) δ 7.89 (s, 1H), 7.74 (dd, J=8.6, 1.1 Hz, 2H), 7.55 (t, J=7.9 Hz, 2H), 7.49-7.45 (m, 1H), 7.33-7.26 (m, 3H), 7.18 (dd, J=10.3, 3.2 Hz, 1H), 7.00-6.97 (m, 2H), 6.84 (dd, J=10.2, 3.2 Hz, 1H), 6.12 (dd, J=10.3, 2.0 Hz, 1H), 6.03 (dd, J=10.2, 2.0 Hz, 1H), 4.65 (dd, J=12.2, 9.6 Hz, 1H), 4.40 (dd, J=12.2, 6.6 Hz, 1H), 3.45 (dd, J=15.0, 6.9 Hz, 1H), 3.41-3.31 (m, 1H), 3.19 (dd, J=15.0, 3.8 Hz, 1H); $^{13}$C NMR (150 MHz, CDCl$_3$) δ 184.02, 169.61, 144.74, 142.93, 136.97, 136.43, 129.84, 129.81 (4C), 129.08 (3C), 128.99, 128.80 (2C), 121.00, 120.40 (2C), 83.44, 63.71, 41.55, 23.65 ppm.

Example 48: Preparation of 3-(3-bromobenzyl)-5-isopropyl-1-oxa-5-azaspiro[5,5]undeca-7,10-diene-4,9-dione

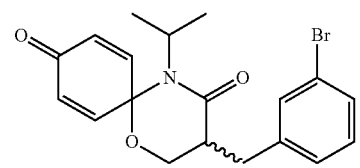 [SMILES: CC(C)N1C(=O)C(Cc2cccc(Br)c2)COC12C=CC(=O)C=C2]

The target compound was obtained by cyclization performed by the same manner as described in Example 19 except that the compound of Preparative Example 45 was used instead of the compound of Preparative Example 1 as the starting material in Example 19.

$^1$H NMR (600 MHz, CDCl$_3$) δ 7.42-7.38 (m, 2H), 7.21-7.15 (m, 2H), 6.81 (dd, J=10.1, 3.2 Hz, 1H), 6.57 (dd, J=10.1, 3.1 Hz, 1H), 6.34-6.30 (m, 2H), 3.97 (dd, J=12.0, 5.0

Hz, 1H), 3.80 (dd, J=12.0, 6.2 Hz, 1H), 3.18 (dd, J=13.8, 4.2 Hz, 1H), 3.07-2.95 (m, 1H), 2.97 (dd, J=13.8, 9.3 Hz, 1H), 2.80-2.76 (m, 1H), 1.41 (dd, J=15.3, 6.8 Hz, 6H); $^{13}$C NMR (150 MHz, CDCl$_3$) δ 184.06, 168.62, 144.11, 144.07, 140.73, 132.26, 130.46, 130.42, 130.15, 129.87, 127.96, 122.65, 82.69, 62.39, 49.87, 43.96, 34.48, 20.50, 20.45 ppm.

Example 49: Preparation of 5-isopropyl-3-(4-nitrobenzyl)-1-oxa-5-azaspiro[5,5]undeca-7,10-diene-4,9-dione

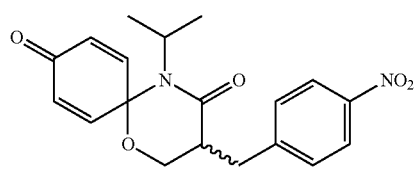 [SMILES: CC(C)N1C(=O)C(Cc2ccc([N+](=O)[O-])cc2)COC12C=CC(=O)C=C2]

The target compound was obtained by cyclization performed by the same manner as described in Example 19 except that the compound of Preparative Example 46 was used instead of the compound of Preparative Example 1 as the starting material in Example 19.

$^1$H NMR (600 MHz, CDCl$_3$) δ 8.21-8.17 (m, 2H), 7.42 (d, J=8.7 Hz, 2H), 6.83-6.80 (m, 1H), 6.64-6.60 (m, 1H), 6.36-6.31 (m, 2H), 3.99 (dd, J=12.0, 4.9 Hz, 1H), 3.78 (dd, J=12.0, 6.3 Hz, 1H), 3.32 (dd, J=13.9, 4.5 Hz, 1H), 3.11-3.05 (m, 2H), 2.86-2.82 (m, 1H), 1.42 (d, J=6.8 Hz, 3H), 1.39 (d, J=6.8 Hz, 3H); $^{13}$C NMR (150 MHz, CDCl$_3$) δ 183.92, 168.21, 146.92, 146.33, 143.88, 143.72, 130.63, 130.56, 130.14 (2C), 123.83 (2C), 82.78, 62.31, 49.91, 43.91, 34.65, 20.47, 20.39 ppm.

The chemical structures of the compounds prepared in Examples 1-49 are shown in Table 2 below.

TABLE 2

| Example | Chemical Structure |
|---|---|
| 1 | |
| 2 | |
| 3 | |
| 4 | 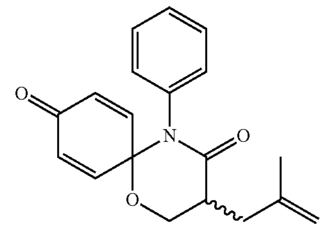 [SMILES: C=C(C)CC1COC2(C=CC(=O)C=C2)N(c2ccccc2)C1=O] |
| 5 | 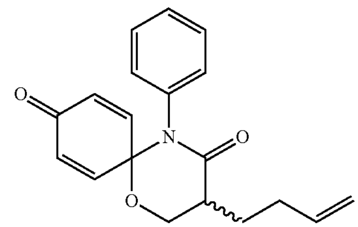 [SMILES: C=CCCC1COC2(C=CC(=O)C=C2)N(c2ccccc2)C1=O] |
| 6 | 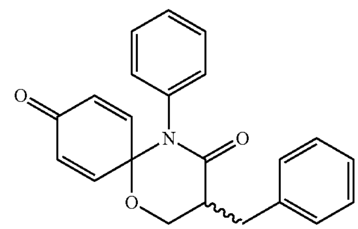 |
| 7 | 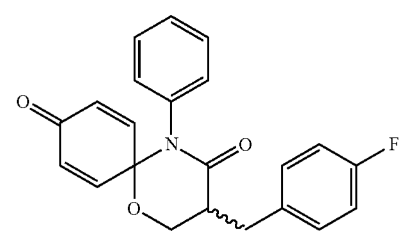 [SMILES: O=C1C=CC2(C=C1)OCC(Cc1ccc(F)cc1)C(=O)N2c1ccccc1] |
| 8 | 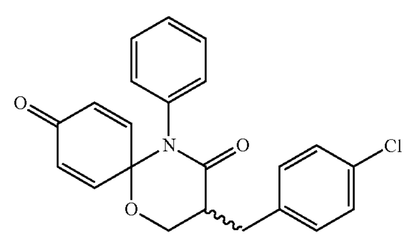 |
| 9 | 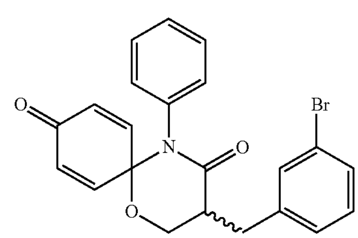 |

TABLE 2-continued
| Example | Chemical Structure |
|---|---|
| 10 | 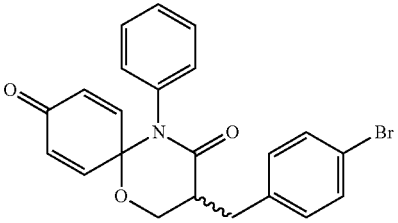 [SMILES: O=C1C=CC2(C=C1)OCC(Cc1ccc(Br)cc1)C(=O)N2c1ccccc1] |
| 11 | 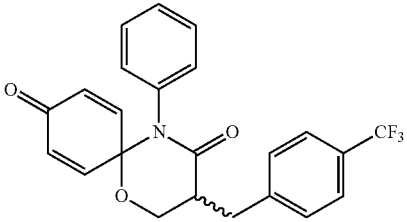 [SMILES: O=C1C=CC2(C=C1)OCC(Cc1ccc(C(F)(F)F)cc1)C(=O)N2c1ccccc1] |
| 12 | 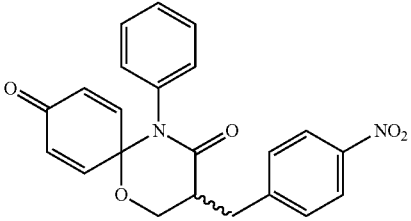 [SMILES: O=C1C=CC2(C=C1)OCC(Cc1ccc([N+](=O)[O-])cc1)C(=O)N2c1ccccc1] |
| 13 | 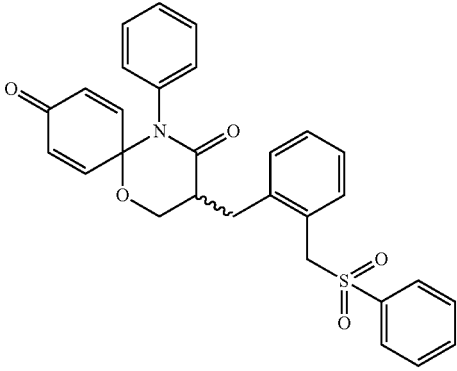 [SMILES: O=C1C=CC2(C=C1)OCC(Cc1ccccc1CS(=O)(=O)c1ccccc1)C(=O)N2c1ccccc1] |
| 14 | 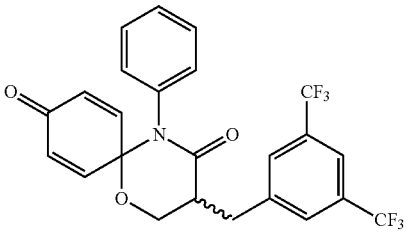 |
| 15 | 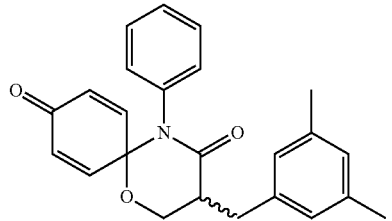 [SMILES: Cc1cc(C)cc(CC2COC3(C=CC(=O)C=C3)N(c3ccccc3)C2=O)c1] |
| 16 | 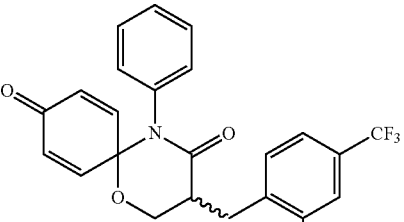 |
| 17 | 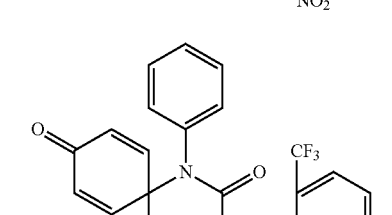 |
| 18 | 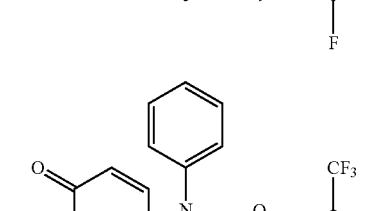 |
| 19 | 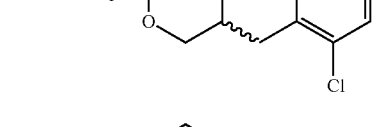 |
| 20 | 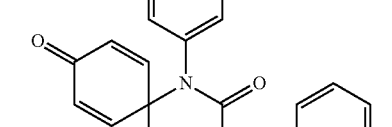 |
| 21 | 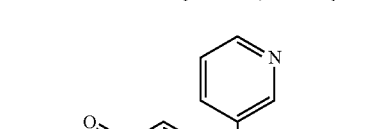 |

TABLE 2-continued
| Example | Chemical Structure |
|---|---|
| 22 | 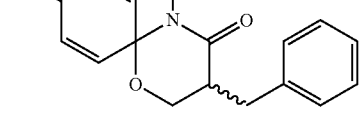 |
| 23 | 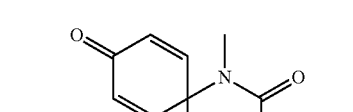 |
| 24 | 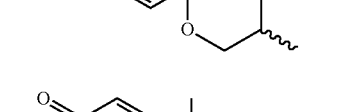 |
| 25 | 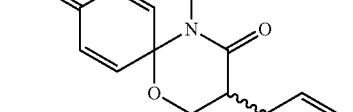 |
| 26 | 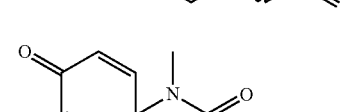 |
| 27 | 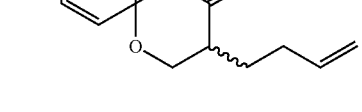 |
| 28 | 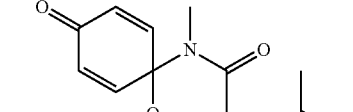 |
| 29 | 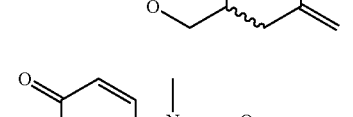 |
| 30 | 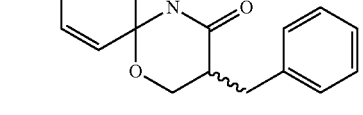 |
| 31 | 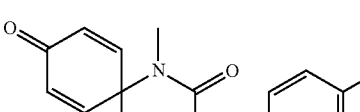 |
| 32 | 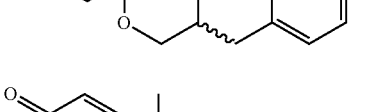 |
| 33 | 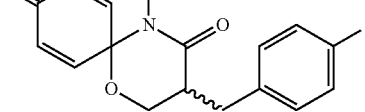 |
| 34 | 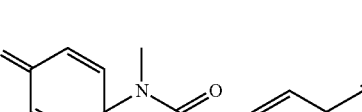 |
| 35 | 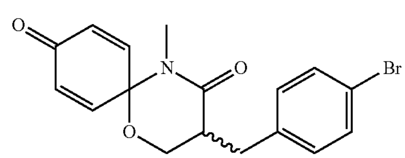 [SMILES: CN1C(=O)C(Cc2ccc(Br)cc2)COC12C=CC(=O)C=C2] |
| 36 | 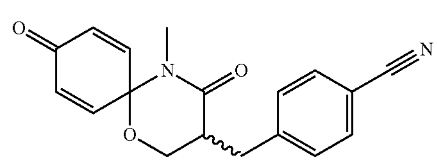 [SMILES: CN1C(=O)C(Cc2ccc(C#N)cc2)COC12C=CC(=O)C=C2] |

TABLE 2-continued

| Example | Chemical Structure |
|---|---|
| 37 | 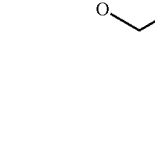 |
| 38 | 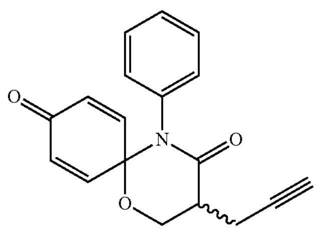 [SMILES: C#CCC1COC2(C=CC(=O)C=C2)N(c2ccccc2)C1=O] |
| 39 | 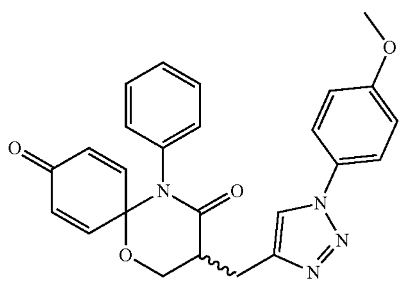 [SMILES: COc1ccc(-n2cc(CC3COC4(C=CC(=O)C=C4)N(c4ccccc4)C3=O)nn2)cc1] |
| 40 | 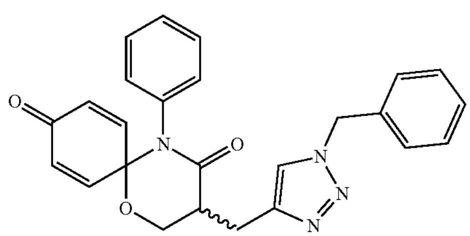 [SMILES: O=C1C=CC2(C=C1)OCC(Cc1cn(Cc3ccccc3)nn1)C(=O)N2c1ccccc1] |
| 41 | 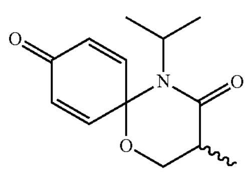 [SMILES: CC1COC2(C=CC(=O)C=C2)N(C(C)C)C1=O] |
| 42 | 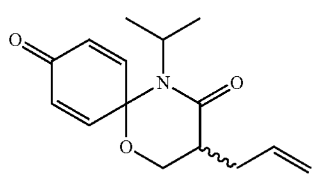 [SMILES: C=CCC1COC2(C=CC(=O)C=C2)N(C(C)C)C1=O] |
| 43 | 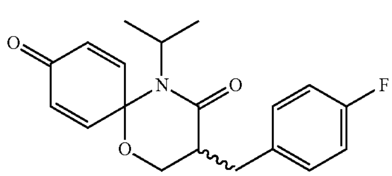 [SMILES: CC(C)N1C(=O)C(Cc2ccc(F)cc2)COC12C=CC(=O)C=C2] |

TABLE 2-continued

| Example | Chemical Structure |
|---|---|
| 44 | 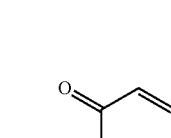 |
| 45 | 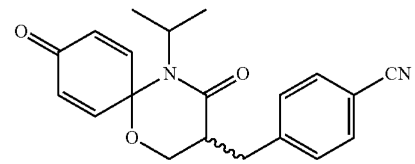 [SMILES: CC(C)N1C(=O)C(Cc2ccc(C#N)cc2)COC12C=CC(=O)C=C2] |
| 46 | 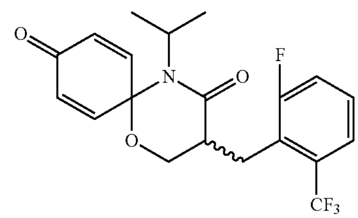 |
| 47 | 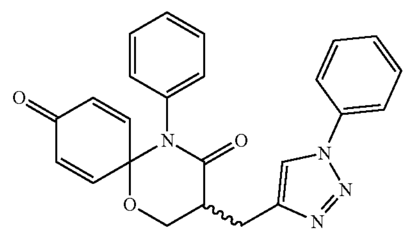 [SMILES: O=C1C=CC2(C=C1)OCC(Cc1cn(-c3ccccc3)nn1)C(=O)N2c1ccccc1] |
| 48 | 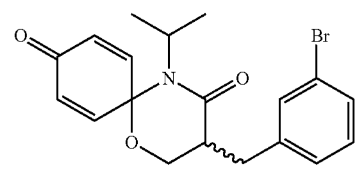 [SMILES: CC(C)N1C(=O)C(Cc2cccc(Br)c2)COC12C=CC(=O)C=C2] |
| 49 | 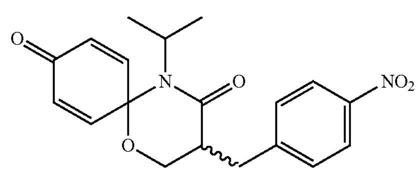 [SMILES: CC(C)N1C(=O)C(Cc2ccc([N+](=O)[O-])cc2)COC12C=CC(=O)C=C2] |

Experimental Example 1: Evaluation of Nerve Cell Line Protective Activity

The following experiment was performed to evaluate the nerve cell line protective activity of the compound represented by formula 1 or formula 1' of the present invention (novel spiroquinone derivative compound).

Figure 9:
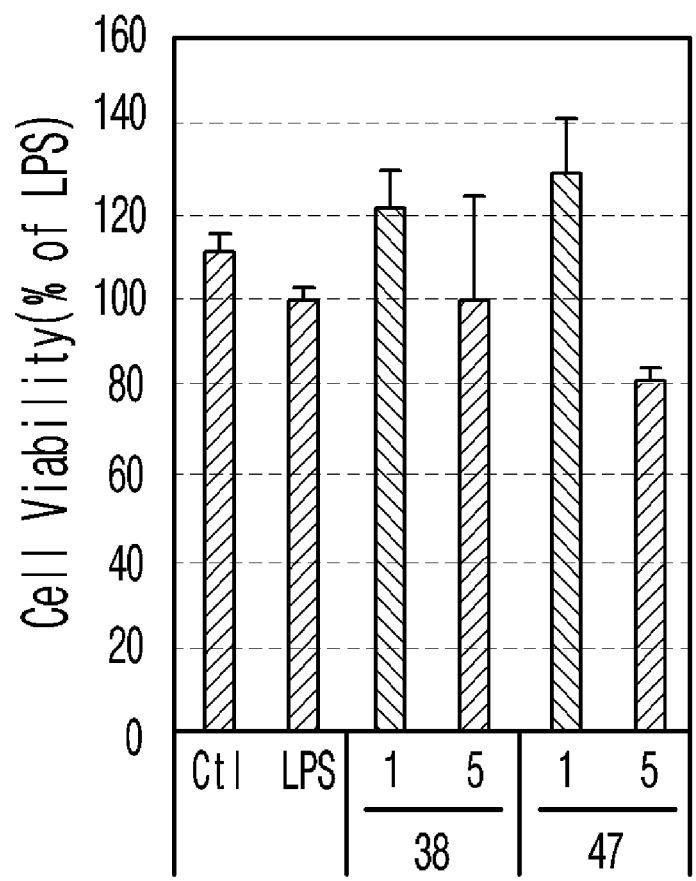
FIG. 9 is a graph illustrating the cell viability rate (%) of the neuronal cell line (murine microglial BV-2 cells) treated with a neurotoxicant (LPS) according to the different concentrations (1 μM and 5 μM) of the example 38 and 47 compound.

Particularly, mouse microglial BV2 cells were cultured in Dulbecco's modified Eagle's medium (DMEM; Hyclone) supplemented with 10% heat-inactivated fetal bovine serum (Hyclone, USA) in a 5% $CO_2$ incubator with 95% humidity at 37° C. To induce cell damage, LPS (lipid polysaccharide) was used as a toxic substance. To investigate the cell protective activity in the cell damage model, 6-shogaol was used as for the positive control. When the cell confluence reached 70%~80%, the cells were treated with the compound of the present invention at different concentrations of 0.01 µM, 0.1 µM and 1 µM, or 1 µM, 5 µM and 10 µM in serum-free condition. 30 minutes later, a toxic substance (100 mg/mL of LPS) was treated to the cells. All the chemicals treated were dissolved in dimethylsulfoxide (DMSO) before the treatment and the final DMSO concentration was 0.2%. 24 hours later, MTT assay was performed in BV2 cells and the results are shown in FIG. 2 and FIG. 4 and FIG. 9 (Con: DMSO treated group (not treated with the compound of the invention and LPS), LPS: LPS treated group (treated with the compound of the invention)).

As shown in FIG. 2, the cell survival rate of the LPS treated nerve cell line (murine microglial BV-2 cells) was significantly increased by the compound of the example of the present invention dose-dependently.

As shown in FIG. 4 and FIG. 9, the cell survival rate of the LPS treated nerve cell line (murine microglial BV-2 cells) was significantly increased by the compound of the example of the present invention dose-dependently.

Therefore, the compound represented by formula 1 or formula 1' of the present invention can protect the nerve cell line excellently so that it can be effectively used as an active ingredient of a pharmaceutical composition for the prevention or treatment of neurological disease.

Experimental Example 2: Quantitative Evaluation of Nitrite Generation

The following experiment was performed to quantify the nitrite generated in the nerve cell line by the compound represented by formula 1 or formula 1' of the present invention (the novel spiroquinone derivative compound).

Particularly, in order to quantify the nitrite generation in the LPS treated nerve cell line, nitrite generated from nitric oxide secreted therein was quantified. With the quantified nitrite, the inhibition of microglial activation and the neuron protection effect thereby were examined. The nerve cell line (BV2) was treated with LPS (100 mg/mL), and then treated with the compound of the present invention at different concentrations of 0.01 µM, 0.1 µM and 1 µM, or 1 µM, 5 µM and 10 µM (Con: DMSO treated group (not treated with the compound of the invention and LPS), LPS: LPS treated group (treated with the compound of the invention)). The results are shown in FIGS. 1, 3 and 8.

Figure 3:
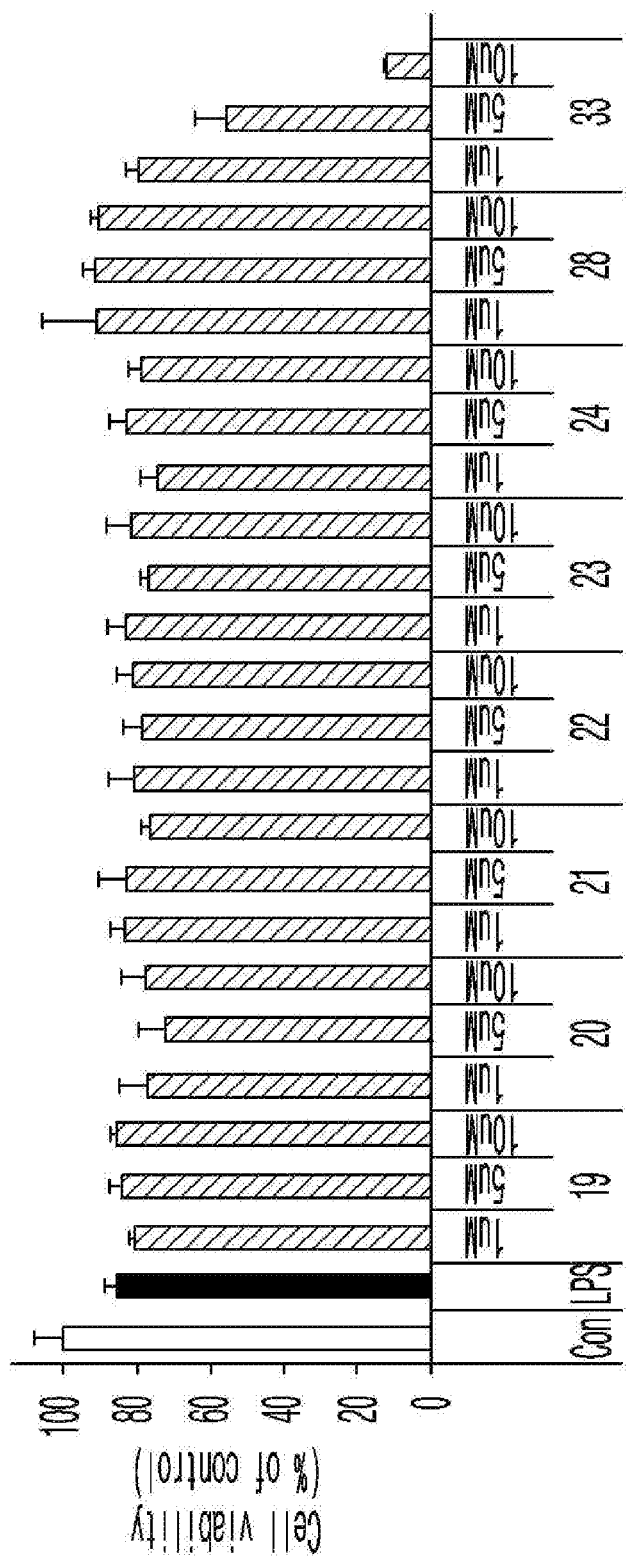
FIG. 3 is a graph illustrating the nitrite generation from the comparison of nitric oxide measured in the neuronal cell line (murine microglial BV-2 cells) treated with a neurotoxicant (LPS) according to the different concentrations (1 μM, 5 μM, and 10 μM) of the compound of the present invention.
Figure 5:
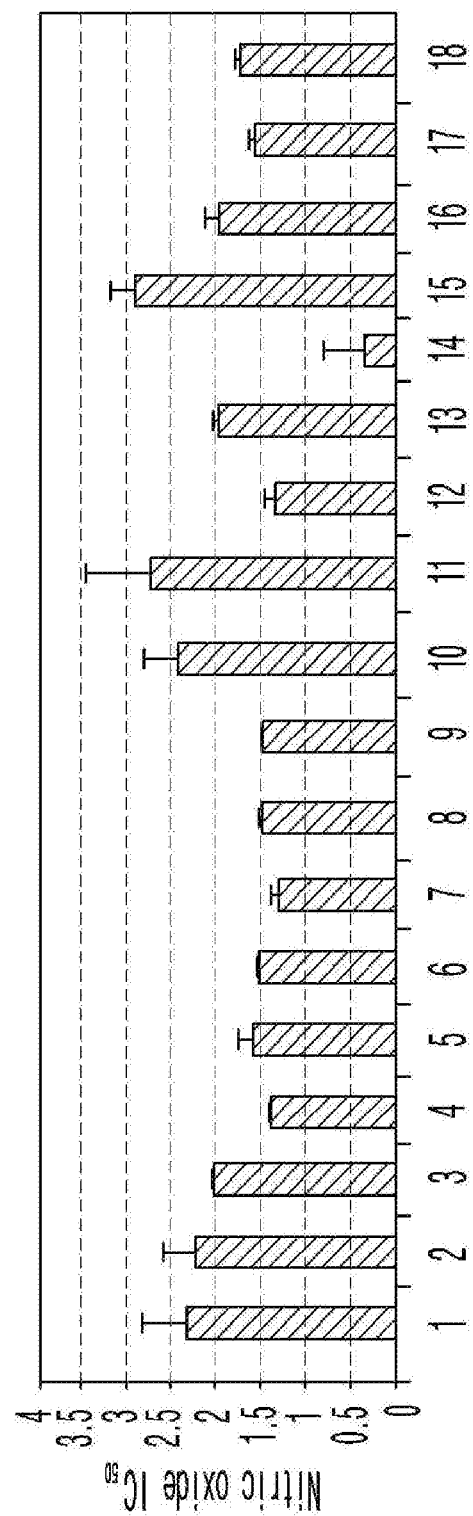
FIG. 5 is a graph illustrating the $IC_{50}$ value calculated from the detection results of the nitric oxide generation measured by concentration gradient of the compound of the present invention (horizontal axis: example number, longitudinal axis: $IC_{50}$ (μM)).

Further, $IC_{50}$ was calculated from the quantification of nitric oxide measured by concentration gradient in FIGS. 1 and 3, and the results are shown in FIG. 5.

Figure 8:
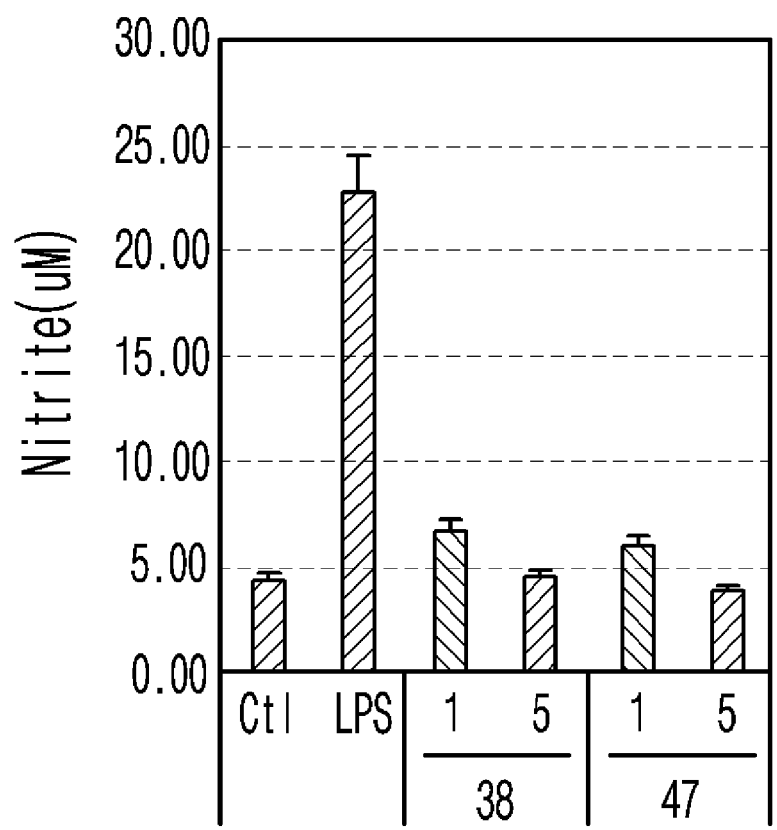
FIG. 8 is a graph illustrating the nitrite generation from the comparison of nitric oxide measured in the neuronal cell line (murine microglial BV-2 cells) treated with a neurotoxicant (LPS) according to the different concentrations (1 μM and 5 μM) of the example 38 and 47 compound.

As shown in FIGS. 1 and 8, the compound of the example of the present invention significantly inhibited the generation of nitrite in the LPS treated nerve cell line (murine microglial BV-2 cells) dose-dependently (0.01, 0.1, and 1 µM).

As shown in FIG. 3, the compound of the example of the present invention significantly inhibited the generation of nitric oxide in the LPS treated nerve cell line (murine microglial BV-2 cells) dose-dependently (1, 5, and 10 µM).

As shown in FIG. 5, all the compounds of the examples of the invention exhibited excellent inhibitory effect at the level of micromole based on the $IC_{50}$ of the compound of the invention for nitric oxide. In particular, the compound of example 14 showed as excellent nitric oxide inhibitory effect as about up to 0.3 µM, indicating excellent nerve cell protection effect.

Inflammatory response in the central nervous system plays a key role in degenerative brain diseases and the inflammatory response mediated by the over-activation of microglial cells induces the death of neurons. Therefore, the inhibition of the microglial activation can be a pharmacological target for the treatment of degenerative brain diseases. Considering that the studies on the relationship between the microglial activation and the diseases like Parkinson's disease and Alzheimer's disease confirmed the microglial activation is induced by the treatment of LPS and then iNOS (nitric oxide synthase) is expressed to secret nitric oxide (NO), the compound represented by formula 1 or formula 1' (the novel spiroquinone derivative compound) of the present invention which displays excellent protective effect on nerve cells can be effectively used as an active ingredient of a pharmaceutical composition for the prevention or treatment of neurological disease.

Experimental Example 3: Evaluation of Acetylcholine Esterase Inhibition Activity The following experiment was performed to evaluate the acetylcholine esterase inhibition activity of the compound represented by formula 1 or formula 1' of the present invention.

Particularly, a quantitative kit (ACh quantification colorimetric assay kit from BioVision) was prepared in order to quantify acetylcholine esterase (eeAChE, EC 3.1.1.7) and acetylcholine chloride (ACh) of Electrophorus electricus and acetylcholine. To measure the enzyme inhibition activity of the compound of the example of the invention, the following experiment was performed based on the standardized method of the manufacturer of the Ach kit (Draczkowski, P. et al. Bba-Gen Subjects 1860, 967-974, doi: 10.1016/j.bbagen.2015.11.006 (2016)).

First, acetylcholine esterase (eeAChE, EC 3.1.1.7) was dissolved in 20 µM Tris-HCL buffer at the concentration of 5 µM. Acetylcholine chloride was dissolved in 20 mM Tris-HCL buffer, resulting in the preparation of a Tris-HCL aqueous solution containing 10 µM acetylcholine chloride. The compound of the example was prepared in different concentrations of 10 µM and 30 µM. The prepared acetylcholine chloride solution and the compound solution were mixed in 20 µM acetylcholine esterase. 20 minutes and 30 minutes after mixing, the color change of the quantitative kit was measured at 570 nm in order to evaluate the inhibitory effect of the compound particularly to inhibit acetylcholine esterase that decomposes acetylcholine into choline.

Figure 6:
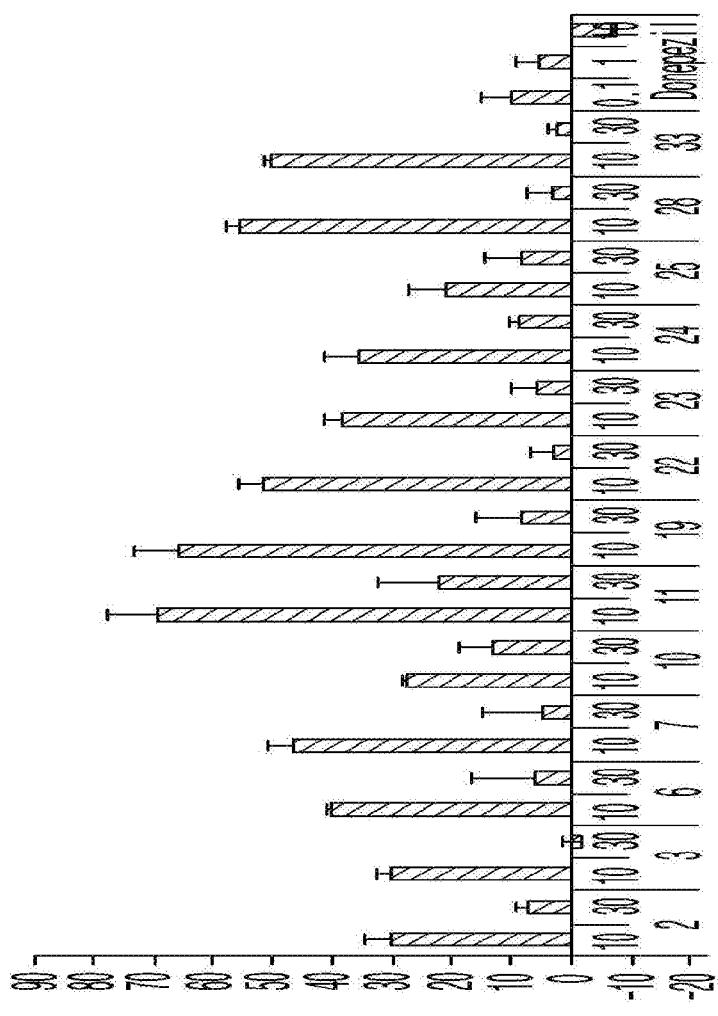
FIG. 6 is a graph illustrating the acetylcholine esterase residual activity (%) after the treatment of the compound of the present invention at two different concentrations of 10 μM and 30 μM.

All the experiments were repeated at least twice, from which the mean values and the standard deviations were calculated. The results are shown in Table 3 and FIG. 6.

TABLE 3

| | Residual activity of acetylcholine esterase (%) | |
| --- | --- | --- |
| Example | 10 µM | 30 µM |
| 2 | 29.73 | 7.03 |
| 3 | 30.32 | −2.03 |
| 6 | 40.19 | 6.07 |
| 7 | 46.73 | 4.74 |
| 10 | 27.26 | 12.95 |
| 11 | 69.43 | 22.06 |
| 19 | 66.08 | 8.07 |
| 22 | 51.63 | 2.47 |
| 23 | 38.07 | 5.64 |
| 24 | 35.63 | 8.89 |
| 25 | 20.92 | 8.15 |
| 28 | 55.43 | 3.08 |
| 33 | 50.53 | 2.08 |

As shown in Table 3, all the compounds of the examples of the invention inhibited acetylcholine esterase activity significantly.

Therefore, the compound of the present invention, the stereoisomer thereof or the pharmaceutically acceptable salt thereof can be effectively used as an active ingredient of a pharmaceutical composition for the prevention or treatment of acetylcholine esterase related disease such as neurological disease due to the excellent acetylcholine esterase inhibitory activity of the compound.

Experimental Example 4: Evaluation of Enzyme Inhibition Activity Selectivity

The following experiment was performed in order to evaluate the selectivity of the enzyme inhibition activity of the compound of the present invention represented by formula 1 or formula 1'.

The selectivity of the compound of the present invention to 369 kinase panels (Reaction Biology Corp) was investigated. Using the radio-labeled ATP ([$\gamma$-$^{33}$P] ATP), the extent of the substitution of the substrate with $^{33}$P-phosphorylated substrate was measured, by which the changes in kinase activity were investigated. At this time, 30 µM of the compound of the example, 10 µM of ATP and 10 µM of substrate were used. As for the control, staurosporine was used in a 10-dose IC$_{50}$ mode with 4-fold step dilution starting at 20 or 100 µM. The example compounds were tested in a 10-dose IC$_{50}$ mode with 3 or 4-fold continuous dilution starting at 10, 20 or 100 µM. Curve fitting of the control compound with enzyme activity of less than 65% was performed at the highest concentration of the compound. DMSO concentration was regulated. Based on the raw data, the enzyme activity for the DMSO control group was calculated. Among the calculated inhibitory activity of the compound of the example against 369 enzymes, the enzymes affected significantly and the inhibitory activities (%) against the enzymes are shown in Table 4.

TABLE 4

| Kinase | Residual enzyme activity (%) (Values calculated to DMSO control) | |
|---|---|---|
| | 1st | 2nd |
| JNK 1 | 36.03 | 35.58 |
| CDK/cyclin O | 43.80 | 42.33 |
| DAPK 1 | 45.43 | 45.32 |
| PKCa | 46.47 | 44.81 |
| CKD 1/cyclin B | 46.54 | 45.38 |
| MST3/STK24 | 58.19 | 57.62 |
| TLK 1 | 58.62 | 57.28 |
| JNK 2 | 58.79 | 57.84 |
| RIPK 5 | 59.94 | 58.59 |
| CDK3/cyclin E | 60.20 | 58.48 |
| PKN 2/PRK 2 | 64.75 | 62.16 |
| Haspin | 66.80 | 66.06 |
| STK25/YSK1 | 66.95 | 66.88 |
| ARK5/NUAK1 | 70.84 | 70.70 |
| PKCb 2 | 71.17 | 67.73 |
| JNK 3 | 73.42 | 70.58 |

As shown in Table 4, the compound of the present invention displayed a significant enzyme inhibition activity on JNK1, CDK2/cyclin O, DAPK1, PKCa, CDK1/cyclin B, MST3/STK24, TLK1, JNK2, RIPK5, CDK3/cyclin E, PKN2/PRK2, Haspin, STK25/YSK1, ARK5/NUAK1, PKCb2, and JNK3. Therefore, the compound of the present invention can be effectively used as an active ingredient of a pharmaceutical composition for the prevention or treatment of the diseases relating to JNK1, CDK2/cyclin O, DAPK1, PKCa, CDK1/cyclin B, MST3/STK24, TLK1, JNK2, RIMS, CDK3/cyclin E, PKN2/PRK2, Haspin, STK25/YSK1, ARK5/NUAK1, PKCb2, and JNK3.

Experimental Example 5: Animal Model Experiment

The following experiment was performed to investigate the neuroprotective effect of the compound of the present invention in an animal model.

Particularly, Y-maze test was performed with an animal model (mice) to evaluate the effect of the compound of the present invention. The spatial recognition ability of the mouse was evaluated. A Y-type maze in the size of 20 cm (length)×5 cm (width)×10 cm (height) was prepared. The floor and the walls of the maze were made of dark opaque polyvinyl plastic, and the three arms of the maze were named A, B and C (the arms were arranged symmetrically at the angle of 120° to each other). The mice were immersed in the Y-maze for 2 minutes, followed by the 8-minute observation to record the number of times completely entered each arm (from the nose to the tail). When the mouse was continuously entered three different arms, one point was given to each arm. If the entry was not made serially, the point was not given. The alternation behavior was defined as three consecutive inputs to three different arms of the maze. The spatial recognition ability was calculated according to the following formula.

$$\text{Spontaneous Alternation Behavior Ratio (\%)}= [(N_{alternation\ number})/(N_{total\ number\ of\ entry}-2)]\times 100$$

($N_{alternation\ number}$ is the number of times the alternation movement is observed (1 point) and $N_{total\ number\ of\ entry}$ is the total number of arm entry)

Particularly, sequence (for example, ABCCAB, etc) and the number of arm entry were recorded manually for 8 minutes for each mouse. Real alternation was accepted only three consecutive selections (that is, includes ABC, CAB, or BCA but not BAB).

One hour before the experiment, the mouse was administered with donepezil (5 mg/kg, p.o.), 10% Tween 80 solution and the compound of the example of the present invention (10 mg/kg, p.o.). Scopolamine (1 mg/kg, i.p.) was administered to induce memory impairment 30 minutes before the experiment.

Figure 7:
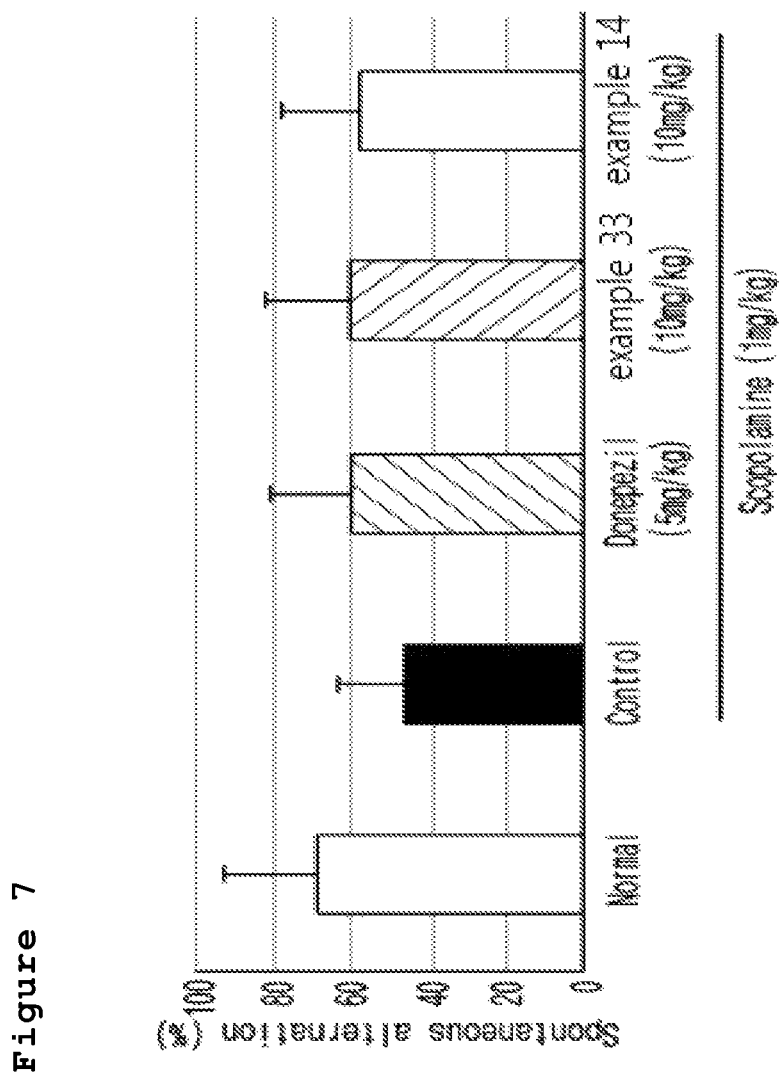
FIG. 7 is a graph illustrating the ratio (%) of spontaneous alternation behavior by memory damage induced by scopolamine (1 mg/kg, i.p.) in the test mouse after the treatment of donepezil (5 mg/kg, p.o.), 10% Tween 80 solution, and the compound of the present invention (10 mg/kg, p.o.).

The results of the spontaneous alternation behavior ratio (%) obtained from the experiment above are shown in FIG. 7.

As shown in FIG. 7, after the memory impairment was induced, the spatial recognition function of the mouse was significantly reduced. In the meantime, when the compound of the example of the present invention was treated to the mouse, the memory impairment of the mouse was recovered to the similar level to the control group treated with donepezil.

Therefore, as confirmed in the animal model test, the compound of the example of the present invention can be effectively used for the pharmaceutical composition for the prevention or treatment of neurological disease, preferably cerebral nervous system disease and central nervous system disease, due to the neuroprotective activity of the compound.

INDUSTRIAL APPLICABILITY

The novel spiroquinone derivative compound of the present invention, the stereoisomer thereof or the pharmaceutically acceptable salt thereof is not only excellent in inhibiting the microglial activation and the activities of acetylcholine esterase, JNK1, JNK2, and JNK3 but also displays the significant enzyme activity suppressive effect on the neurological disease related enzyme group including RIPK5, CDK3/cyclin E, PKN2/PRK2, Haspin, STK25/YSK1, ARK5/NUAK1, PKCb2, CDK2/cyclin O, DAPK1, PKCa, CDK1/cyclin B, MST3/STK24, and TLK1, in addition to the cell death suppressive effect. Therefore, the novel spiroquinone derivative compound of the present invention, the stereoisomer thereof or the pharmaceutically acceptable salt thereof can be effectively used as an active ingredient of a pharmaceutical composition for the prevention or treatment of neurological disease or as an active ingredient of a health functional food for the prevention or improvement of neurological disease.

The invention claimed is:

1. A compound represented by formula 1 or formula 1' below, a stereoisomer thereof, or a pharmaceutically acceptable salt thereof:

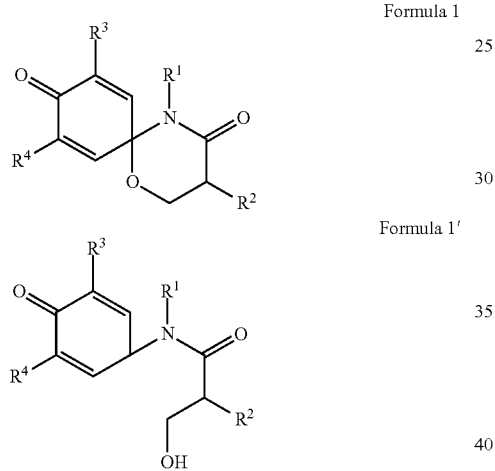

Formula 1

Formula 1' wherein, $R^1$ is nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from N, O or S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from N, O, or S, or nonsubstituted or substituted 5-10 membered heteroaryl containing one or two heteroatoms selected from N, O, or S, wherein, the substituted alkyl, alkenyl, cycloalkyl, heterocycloalkyl, arylalkyl, aryl, heteroarylalkyl, or heteroaryl is independently substituted with one or more substituents selected from substituted or nonsubstituted $C_{6-10}$arylsulfonyl, substituted or nonsubstituted $C_{6-10}$arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from N, O or S, substituted or nonsubstituted 5-10 membered heteroarylsulfonyl $C_{1-5}$ alkyl containing one or more heteroatoms selected from N, O or S, substituted or nonsubstituted 5-10 membered heteroaryl containing one or more heteroatoms selected from N, O or S, substituted or nonsubstituted 5-10 membered heteroaryl $C_{1-5}$ alkyl containing one or more heteroatoms selected from N, O or S, substituted or nonsubstituted $C_{1-6}$ straight or branched alkyl, $C_{1-6}$ straight or branched alkoxy, hydroxy, halogen, amino, nitro, or cyano, wherein, the substituted $C_{6-10}$arylsulfonyl, $C_{6-10}$arylsulfonyl $C_{1-5}$ alkyl, $C_{6-10}$aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from $C_{1-6}$ straight or branched alkyl, $C_{1-6}$ straight or branched alkoxy, hydroxy, halogen, amino, nitro, or cyano;

$R^2$ is hydrogen, nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$ cycloalkyl, nonsubstituted or substituted $C_{3-10}$ heterocycloalkyl containing one or more heteroatoms selected from N, O or S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from N, O, or S, or nonsubstituted or substituted 5-10 membered heteroaryl containing one or more heteroatoms selected from N, O, or S, wherein, the substituted alkyl, alkenyl, cycloalkyl, heterocycloalkyl, arylalkyl, aryl, heteroarylalkyl, or heteroaryl is independently substituted with one or more substituents selected from substituted or nonsubstituted $C_{6-10}$arylsulfonyl, substituted or nonsubstituted $C_{6-10}$arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from N, O or S, substituted or nonsubstituted 5-10 membered heteroarylsulfonyl $C_{1-5}$ alkyl containing one or more heteroatoms selected from N, O or S, substituted or nonsubstituted 5-10 membered heteroaryl containing one or more heteroatoms selected from N, O or S, substituted or nonsubstituted 5-10 membered heteroaryl $C_{1-5}$ alkyl containing one or more heteroatoms selected from N, O or S, substituted or nonsubstituted $C_{1-6}$ straight or branched alkyl, $C_{1-6}$ straight or branched alkoxy, hydroxy, halogen, amino, nitro, or cyano, wherein, the substituted $C_{6-10}$ arylsulfonyl, $C_{6-10}$ arylsulfonyl $C_{1-5}$ alkyl, $C_{6-10}$ aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from $C_{1-6}$ straight or branched alkyl, $C_{1-6}$ straight or branched alkoxy, hydroxy, halogen, amino, nitro, or cyano; and $R^3$ and $R^4$ are the same or different, and are independently hydrogen, nonsubstituted or substituted $C_{1-6}$ straight or branched alkyl, nonsubstituted or substituted $C_{1-6}$ straight or branched alkoxy, hydroxy, halogen, amino, nitro, or cyano, wherein, the substituted alkyl or alkoxy is independently substituted with one or more substituents selected from hydroxy, halogen, amino, nitro, or cyano.

2. The compound, the stereoisomer thereof, or the pharmaceutically acceptable salt thereof according to claim 1, wherein the $R^1$ is nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$cycloalkyl, nonsubstituted or substituted $C_{3-10}$heterocycloalkyl containing one or more heteroatoms selected from N, O or S, nonsubstituted or substituted $C_{6-10}$ aryl, or nonsubstituted or substituted 5-10 membered heteroaryl containing one or two heteroatoms selected from N, O, or S, wherein, the substituted alkyl, alkenyl, cycloalkyl, heterocycloalkyl, aryl, or heteroaryl is independently substituted with one or more substituents selected from $C_{1-6}$ straight or branched alkyl, $C_{1-6}$ straight or branched alkoxy, hydroxy, halogen, amino, nitro, or cyano.

3. The compound, the stereoisomer thereof, or the pharmaceutically acceptable salt thereof according to claim 1, wherein the $R^2$ is hydrogen, nonsubstituted or substituted $C_{1-6}$ straight or branched alkyl, nonsubstituted or substituted $C_{1-6}$ straight or branched unsaturated alkyl containing one or more double bonds or triple bonds, nonsubstituted or substituted $C_{3-10}$cycloalkyl, nonsubstituted or substituted $C_{3-10}$heterocycloalkyl containing one or more heteroatoms selected from N, O or S, nonsubstituted or substituted $C_{6-10}$ aryl $C_{1-3}$ alkyl, nonsubstituted or substituted $C_{6-10}$ aryl, nonsubstituted or substituted 5-10 membered heteroaryl $C_{1-3}$ alkyl containing one or more heteroatoms selected from N, O, or S, or nonsubstituted or substituted 5-10 membered heteroaryl containing one or more heteroatoms selected from N, O, or S, wherein, the substituted alkyl, alkenyl, cycloalkyl, heterocycloalkyl, arylalkyl, aryl, heteroarylalkyl, or heteroaryl is independently substituted with one or more substituents selected from substituted or nonsubstituted phenylsulfonyl, substituted or nonsubstituted phenylsulfonyl $C_{1-5}$ alkyl, substituted or nonsubstituted phenyl, substituted or nonsubstituted phenyl $C_{1-6}$ alkyl, substituted or nonsubstituted 5-10 membered heteroarylsulfonyl containing one or more heteroatoms selected from N, O or S, substituted or nonsubstituted 5-10 membered heteroarylsulfonyl $C_{1-5}$ alkyl containing one or more heteroatoms selected from N, O or S, substituted or nonsubstituted 5-10 membered heteroaryl containing one or more heteroatoms selected from N, O or S, substituted or nonsubstituted 5-10 membered heteroaryl $C_{1-6}$ alkyl containing one or more heteroatoms selected from N, O or S, substituted or nonsubstituted $C_{1-6}$ straight or branched alkyl, $C_{1-6}$ straight or branched alkoxy, hydroxy, halogen, amino, nitro, or cyano, wherein, the substituted phenylsulfonyl, phenylsulfonyl $C_{1-5}$ alkyl, phenyl, phenyl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from $C_{1-6}$ straight or branched alkyl, $C_{1-6}$ straight or branched alkoxy, hydroxy, halogen, amino, nitro, or cyano.

4. The compound, the stereoisomer thereof, or the pharmaceutically acceptable salt thereof according to claim 1, wherein the $R^1$ is

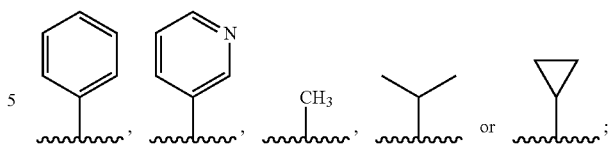

and $R^2$ is

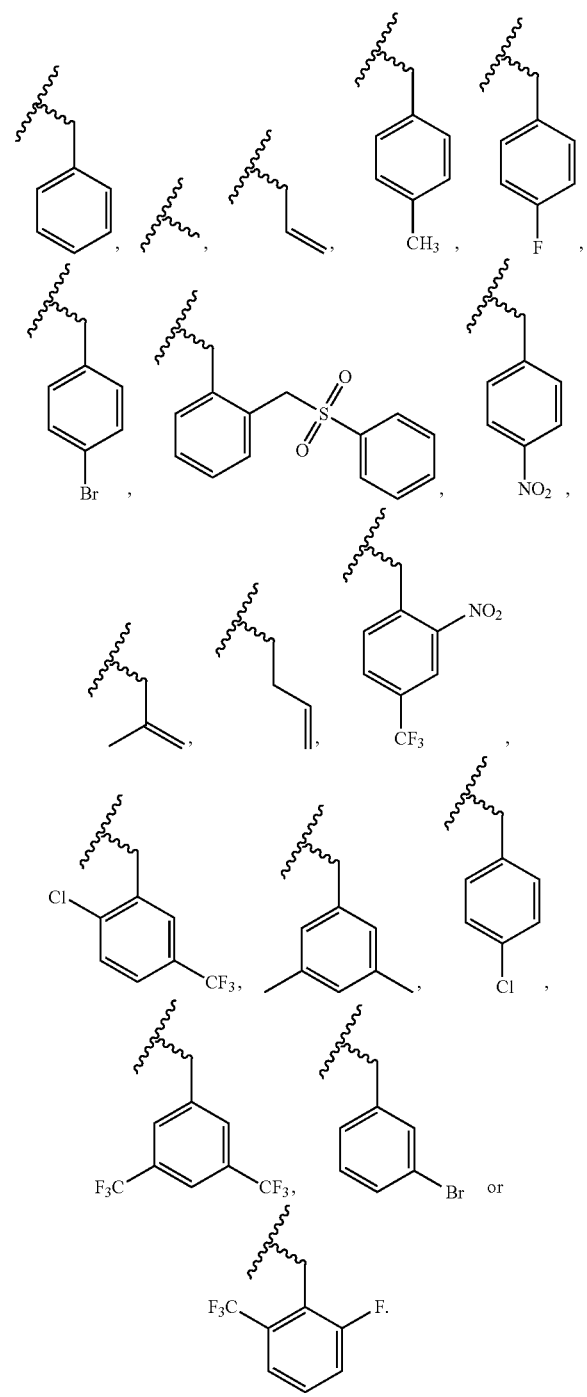

5. The compound, the stereoisomer thereof, or the pharmaceutically acceptable salt thereof according to claim 1, wherein the compound represented by formula 1 is selected from the following compounds:
(1) 5-phenyl-1-oxa-5-azaspiro[5,5]undeca-7,10-diene-4,9-dione;
(2) 3-methyl-5-phenyl-1-oxa-5-azaspiro[5,5]undeca-7,10-diene-4,9-dione;
(3) 3-allyl-5-phenyl-1-oxa-5-azaspiro[5,5]undeca-7,10-diene-4,9-dione;
(4) 3-(2-methyl-allyl)-5-phenyl-1-oxa-5-azaspiro[5,5]undeca-7,10-diene-4,9-dione;
(5) 3-(3-butenyl)-5-phenyl-1-oxa-5-azaspiro[5,5]undeca-7,10-diene-4,9-dione;
(6) 3-benzyl-5-phenyl-1-oxa-5-azaspiro[5,5]undeca-7,10-diene-4,9-dione;
(7) 3-(4-fluoro-benzyl)-5-phenyl-1-oxa-5-azaspiro[5,5]undeca-7,10-diene-4,9-dione;
(8) 3-(4-chloro-benzyl)-5-phenyl-1-oxa-5-azaspiro[5,5]undeca-7,10-diene-4,9-dione;
(9) 3-(3-bromo-benzyl)-5-phenyl-1-oxa-5-azaspiro[5,5]undeca-7,10-diene-4,9-dione;
(10) 3-(4-bromo-benzyl)-5-phenyl-1-oxa-5-azaspiro[5,5]undeca-7,10-diene-4,9-dione;
(11) 3-(4-trifluoromethyl-benzyl)-5-phenyl-1-oxa-5-azaspiro[5,5]undeca-7,10-diene-4,9-dione;
(12) 3-(4-nitro-benzyl)-5-phenyl-1-oxa-5-azaspiro[5,5]undeca-7,10-diene-4,9-dione;
(13) 3-(2-(phenylsulfonylmethyl)-benzyl)-5-phenyl-1-oxa-5-azaspiro[5,5]undeca-7,10-diene-4,9-dione;
(14) 3-(3,5-ditrifluoromethyl-benzyl)-5-phenyl-1-oxa-5-azaspiro[5,5]undeca-7,10-diene-4,9-dione;
(15) 3-(3,5-dimethyl-benzyl)-5-phenyl-1-oxa-5-azaspiro[5,5]undeca-7,10-diene-4,9-dione;
(16) 3-(2-nitro-4-trifluoromethyl-benzyl)-5-phenyl-1-oxa-5-azaspiro[5,5]undeca-7,10-diene-4,9-dione;
(17) 3-(2-fluoro-6-trifluoromethyl-benzyl)-5-phenyl-1-oxa-5-azaspiro[5,5]undeca-7,10-diene-4,9-dione;
(18) 3-(2-chloro-5-trifluoromethyl-benzyl)-5-phenyl-1-oxa-5-azaspiro[5,5]undeca-7,10-diene-4,9-dione;
(19) 3-benzyl-5-(pyridine-3-yl)-1-oxa-5-azaspiro[5,5]undeca-7,10-diene-4,9-dione;
(20) 3-methyl-5-(pyridine-3-yl)-1-oxa-5-azaspiro[5,5]undeca-7,10-diene-4,9-dione;
(21) 3-methyl-8-fluoro-5-phenyl-1-oxa-5-azaspiro[5,5]undeca-7,10-diene-4,9-dione;
(22) 3-allyl-8-fluoro-5-phenyl-1-oxa-5-azaspiro[5,5]undeca-7,10-diene-4,9-dione;
(23) 3-benzyl-8-fluoro-5-phenyl-1-oxa-5-azaspiro[5,5]undeca-7,10-diene-4,9-dione;
(24) 3,8-dimethyl-5-phenyl-1-oxa-5-azaspiro[5,5]undeca-7,10-diene-4,9-dione;
(25) 3-allyl-8-methyl-5-phenyl-1-oxa-5-azaspiro[5,5]undeca-7,10-diene-4,9-dione;
(26) 3-(2-methyl-allyl)-8-methyl-5-phenyl-1-oxa-5-azaspiro[5,5]undeca-7,10-diene-4,9-dione;
(27) 3-benzyl-8-methyl-5-phenyl-1-oxa-5-azaspiro[5,5]undeca-7,10-diene-4,9-dione;
(28) 3,5-dimethyl-1-oxa-5-azaspiro[5,5]undeca-7,10-diene-4,9-dione;
(29) 3-allyl-5-methyl-1-oxa-5-azaspiro[5,5]undeca-7,10-diene-4,9-dione;
(30) 3-(3-butenyl)-5-methyl-1-oxa-5-azaspiro[5,5]undeca-7,10-diene-4,9-dione;
(31) 3-(2-methyl-allyl)-5-methyl-1-oxa-5-azaspiro[5,5]undeca-7,10-diene-4,9-dione;
(32) 3-benzyl-5-methyl-1-oxa-5-azaspiro[5,5]undeca-7,10-diene-4,9-dione;
(33) 3-(4-fluoro-benzyl)-5-methyl-1-oxa-5-azaspiro[5,5]undeca-7,10-diene-4,9-dione;
(34) 3-(4-bromo-benzyl)-5-methyl-1-oxa-5-azaspiro[5,5]undeca-7,10-diene-4,9-dione;
(35) 3-(4-cyano-benzyl)-5-methyl-1-oxa-5-azaspiro[5,5]undeca-7,10-diene-4,9-dione;
(36) 3-(2-(phenylsulfonylmethyl)-benzyl)-5-methyl-1-oxa-5-azaspiro[5,5]undeca-7,10-diene-4,9-dione;
(37) 3-allyl-5-phenyl-1-oxa-5-azaspiro[5,5]undeca-7,10-diene-4,9-dione;
(38) 3-((1-(4-methoxyphenyl)-1H-1,2,3-triazol-4-yl)methyl)-5-phenyl-1-oxa-5-azaspiro[5,5]undeca-7,10-diene-4,9-dione;
(39) 3-((1-benzyl-1H-1,2,3-triazol-4-yl)methyl)-5-phenyl-1-oxa-5-azaspiro[5,5]undeca-7,10-diene-4,9-dione;
(40) 3-methyl-5-isopropyl-1-oxa-5-azaspiro[5,5]undeca-7,10-diene-4,9-dione;
(41) 3-allyl-5-isopropyl-1-oxa-5-azaspiro[5,5]undeca-7,10-diene-4,9-dione;
(42) 3-(4-fluoro-benzyl)-5-isopropyl-1-oxa-5-azaspiro[5,5]undeca-7,10-diene-4,9-dione;
(43) 3-(4-trifluoromethyl-benzyl)-5-isopropyl-1-oxa-5-azaspiro[5,5]undeca-7,10-diene-4,9-dione;
(44) 3-(4-cyano-benzyl)-5-isopropyl-1-oxa-5-azaspiro[5,5]undeca-7,10-diene-4,9-dione;
(45) 3-(2-fluoro-6-trifluoromethyl-benzyl)-5-isopropyl-1-oxa-5-azaspiro[5,5]undeca-7,10-diene-4,9-dione;
(46) 3-((1-phenyl-1H-1,2,3-triazol-4-yl)methyl)-5-phenyl-1-oxa-5-azaspiro[5,5]undeca-7,10-diene-4,9-dione;
(47) 3-(3-bromobenzyl)-5-isopropyl-1-oxa-5-azaspiro[5,5]undeca-7,10-diene-4,9-dione; or
(48) 5-isopropyl-3-(4-nitrobenzyl)-1-oxa-5-azaspiro[5,5]undeca-7,10-diene-4,9-dione.

6. The compound, the stereoisomer thereof, or the pharmaceutically acceptable salt thereof according to claim 1, wherein the compound represented by formula 1' is (1) 3-hydroxy-2-methyl-N-(4-oxocyclohexa-2,5-diethyl)-N-(pyridine-3-yl)propanamide.

7. A preparation method of the compound represented by formula 1 of claim 1 comprising the step of preparing the compound represented by formula 1 from the compound represented by formula 2 (step 1), as shown in reaction formula 1 below,

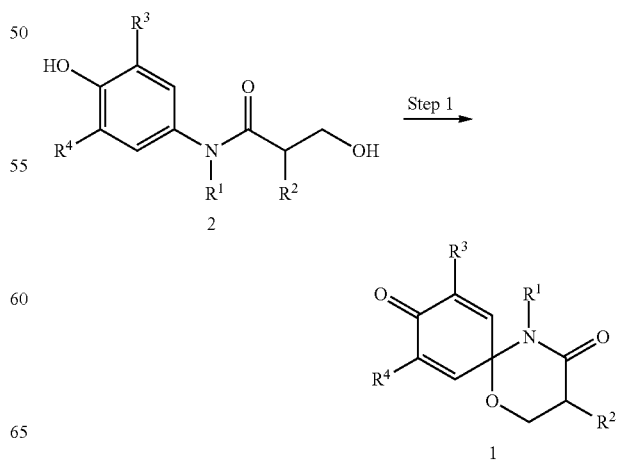

Reaction Formula 1 wherein $R^1$, $R^2$, $R^3$, and $R^4$ are as defined in formula 1 of claim 1, and step 1 comprises an oxidative cyclization reaction.

8. The preparation method according to claim 7, wherein the step 1 is composed of the following substeps, as shown in reaction formula 1':

preparing the compound represented by formula 1" from the compound represented by formula 2' (step 2); and preparing the compound represented by formula 1 from the compound represented by formula 1" (step 3).

Reaction Formula 1'

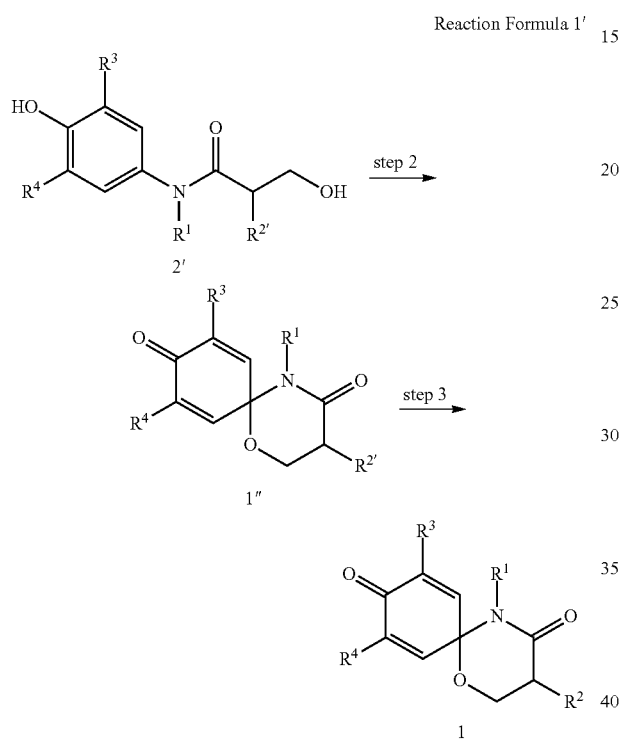

wherein step 2 comprises an oxidative cyclization reaction;

step 3 comprises exposing compound 1" to an azide reagent to produce compound 1;

$R^1$ is

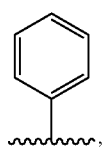

$R^3$ and $R^4$ are hydrogen;

$R^{2'}$ is $C_{3-5}$ straight or branched alkynyl containing one terminal triple bond; and $R^2$ is

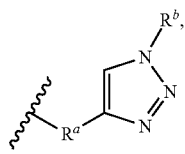

wherein, $R^a$ is $C_{1-3}$ straight or branched alkylene, $R^b$ is hydrogen, substituted or nonsubstituted $C_{6-10}$ arylsulfonyl, substituted or nonsubstituted $C_{6-10}$ arylsulfonyl $C_{1-5}$ alkyl, substituted or nonsubstituted $C_{6-10}$ aryl, substituted or nonsubstituted $C_{6-10}$ aryl $C_{1-5}$ alkyl, substituted or nonsubstituted 5-10 membered heteroarylsulfonyl containing one or more heteroatoms selected from N, O or S, substituted or nonsubstituted 5-10 membered heteroarylsulfonyl $C_{1-5}$ alkyl containing one or more heteroatoms selected from N, O or S, substituted or nonsubstituted 5-10 membered heteroaryl containing one or more heteroatoms selected from N, O or S, substituted or nonsubstituted 5-10 membered heteroaryl $C_{1-5}$ alkyl containing one or more heteroatoms selected from N, O or S, substituted or nonsubstituted $C_{1-6}$ straight or branched alkyl, $C_{1-6}$ straight or branched alkoxy, hydroxy, halogen, amino, nitro, or cyano, wherein, the substituted $C_{6-10}$ arylsulfonyl, $C_{6-10}$ arylsulfonyl $C_{1-5}$ alkyl, $C_{6-10}$ aryl, $C_{6-10}$ aryl $C_{1-5}$ alkyl, 5-10 membered heteroarylsulfonyl, 5-10 membered heteroarylsulfonyl $C_{1-5}$ alkyl, 5-10 membered heteroaryl, 5-10 membered heteroaryl $C_{1-5}$ alkyl, or $C_{1-6}$ straight or branched alkyl is independently substituted with one or more substituents selected from $C_{1-6}$ straight or branched alkyl, $C_{1-6}$ straight or branched alkoxy, hydroxy, halogen, amino, nitro, or cyano.

9. A method of treating memory impairment in a subject having a neurological disease, comprising administering to the subject an effective amount of the compound represented by formula 1, the stereoisomer thereof, or the pharmaceutically acceptable salt thereof of claim 1 as an active ingredient, wherein the neurological disease is Alzheimer's disease, dementia, or mild cognitive impairment.

10. The method of treating neurological disease according to claim 9, wherein the compound treats neurological disease by suppressing the over-activation of microglial cells.

11. The method of treating neurological disease according to claim 9, wherein the compound treats neurological disease by suppressing the activity of acetylcholine esterase.

12. The method of treating neurological disease according to claim 9, wherein the compound treats neurological disease by suppressing the activity of JNK1, CDK2/cyclin O, DAPK1, PKCa, CDK1/cyclin B, MST3/STK24, TLK1, JNK2, RIPK5, CDK3/cyclin E, PKN2/PRK2, Haspin, STK25/YSK1, ARK5/NUAK1, PKCb2, or JNK3.

13. The compound, the stereoisomer thereof, or the pharmaceutically acceptable salt thereof according to claim 1, wherein $R^1$ is nonsubstituted or substituted 5-10 membered heteroaryl containing one heteroatom selected from N, O, or S, wherein, the substituted 5-10 heteroaryl is independently substituted with one or more substituents selected from $C_{1-6}$ straight or branched alkyl, $C_{1-6}$ straight or branched alkoxy, hydroxy, halogen, amino, nitro, or cyano.

* * * * *